US012385029B2

(12) United States Patent
Romney et al.

(10) Patent No.: US 12,385,029 B2
(45) **Date of Patent: *Aug. 12, 2025**

(54) ENGINEERED SYNTHASE FOR PRODUCTION OF TRYPTOPHAN DERIVATIVES AND INTRANSIGENT SUBSTRATES

(71) Applicant: California Institute of Technology, Pasadena, CA (US)

(72) Inventors: David K. Romney, Pasadena, CA (US); Javier Murciano Calles, Ubeda Jaen (ES); Jori E. Wehrmuller, Hohenrain (CH)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/530,082

(22) Filed: Dec. 5, 2023

(65) Prior Publication Data

US 2024/0175002 A1 May 30, 2024

Related U.S. Application Data

(60) Continuation of application No. 17/724,390, filed on Apr. 19, 2022, now Pat. No. 11,873,518, which is a division of application No. 15/685,839, filed on Aug. 24, 2017, now Pat. No. 11,332,729.

(60) Provisional application No. 62/507,383, filed on May 17, 2017, provisional application No. 62/462,193, filed on Feb. 22, 2017, provisional application No. 62/379,039, filed on Aug. 24, 2016.

(51) Int. Cl.

| | |
|---|---|
| ***C12N 9/88*** | (2006.01) |
| ***C07D 209/20*** | (2006.01) |
| ***C07K 4/00*** | (2006.01) |
| ***C12N 15/82*** | (2006.01) |
| ***C12P 13/22*** | (2006.01) |

(52) U.S. Cl.

CPC ............. *C12N 9/88* (2013.01); *C07D 209/20* (2013.01); *C12P 13/227* (2013.01); *C12Y 402/0102* (2013.01)

(58) Field of Classification Search

CPC ..... C12N 9/88; C12N 15/82; C12Y 402/0102

See application file for complete search history.

(56) References Cited

U.S. PATENT DOCUMENTS

| | | | |
|---|---|---|---|
| 5,374,543 | A | 12/1994 | Murdock |
| 6,441,274 | B1 | 8/2002 | Cahoon et al. |
| 6,605,709 | B1 | 8/2003 | Breton |
| 10,513,719 | B2 | 12/2019 | Buller et al. |
| 11,332,729 | B2 | 5/2022 | Romney et al. |
| 2004/0029129 | A1 | 2/2004 | Wang et al. |
| 2016/0298152 | A1 | 10/2016 | Buller et al. |

FOREIGN PATENT DOCUMENTS

| | | |
|---|---|---|
| JP | 2008237075 A | 10/2008 |
| WO | 9534657 A2 | 12/1995 |

OTHER PUBLICATIONS

"RecName: Full=Tryptophan Synthase Beta Chain 1", GeneSeq Database, Accession No. Q9V1G8, 2001, 2 pages.

"Tryptophan Synthase Beta Chain from *Pyrococcus* Sp. (Strain NA2); EC=4.2.1.20", Database UniProt, EBI Accession No. Uniprot: F4HJI6 Database Accession No. F4HJI6, Jun. 28, 2011, 1 page.

U.S. Appl. No. 15/685,839 , "Final Office Action", Apr. 7, 2021, 10 pages.

U.S. Appl. No. 15/685,839 , "Final Office Action", Oct. 20, 2020, 11 pages.

U.S. Appl. No. 15/685,839 , "Non-Final Office Action", Aug. 30, 2021, 10 pages.

U.S. Appl. No. 15/685,839 , "Non-Final Office Action", Mar. 9, 2020, 10 pages.

U.S. Appl. No. 15/685,839 , "Notice of Allowance", Jan. 20, 2022, 9 pages.

U.S. Appl. No. 17/724,390 , "Notice of Allowability", Oct. 18, 2023, 4 pages.

U.S. Appl. No. 17/724,390 , "Notice of Allowance", Sep. 7, 2023, 7 pages.

Buller et al., "Directed Evolution of the Tryptophan Synthase β-Subunit for Stand-Alone Function Recapitulates Allosteric Activation", Proceedings of the National Academy of Sciences, vol. 112, No. 47, Nov. 24, 2015, pp. 14599-14604.

Deckert et al., Uniprot Database, Accession No. 066923, May 2005, 3 pages.

EP17844448.5 , "Extended European Search Report", Jun. 26, 2020, 13 pages.

EP17844448.5 , "Office Action", Sep. 7, 2023, 6 pages.

EP17844448.5 , "Partial Supplementary European Search Report", Jan. 30, 2020, 15 pages.

Herger et al., "Synthesis of β-Branched Tryptophan Analogs Using an Engineered Subunit of Tryptophan Synthase", Journal of the American Chemical Society, vol. 138, No. 27, Jul. 13, 2016, pp. 8388-8391.

Murciano-Calles et al., "A Panel of TrpB Biocatalysts Derived from Tryptophan Synthase through the Transfer of Mutations that Mimic Allosteric Activation", Angewandte Chemie International Edition in English, vol. 55, No. 38, Sep. 12, 2016, pp. 11577-11581.

PCT/US2017/048494 , "International Preliminary Report on Patentability", Mar. 7, 2019, 8 pages.

PCT/US2017/048494 , "International Search Report and Written Opinion", Dec. 27, 2017, 7 pages.

(Continued)

*Primary Examiner* — Maryam Monshipouri

(74) *Attorney, Agent, or Firm* — Kilpatrick Townsend & Stockton LLP

(57) ABSTRACT

This disclosure relates to modified tryptophan synthase and more particularly to modified beta-subunits of tryptophan synthase. The disclosure further relates to cells expressing such modified subunits and methods of producing non-canonical amino acids.

8 Claims, 11 Drawing Sheets

Specification includes a Sequence Listing.

(56) References Cited

OTHER PUBLICATIONS

Romney et al., “Unlocking Reactivity of TrpB: A General Biocatalytic Platform for Synthesis of Tryptophan Analogues”, Journal of the American Chemical Society, vol. 139, No. 31, Aug. 9, 2017, pp. 10769-10776.
EP17844448.5 , “Office Action”, Jan. 17, 2025, 4 pages.

```
             MUTATIONS                                           VG
SEQ ID NO:2 Pyrococcus furiosus      -------------MWFGEFGGQYVPETLIEPLKELEKAYKRFKDDEEFNRQLNYYLKTWA 47
SEQ ID NO:4 Archaeoglobus fulgidus   MRCWLENLSGGRKMKFGEFGGRFVPEVLIPPLEELEKAYDRFKDDEEFKARLEYYLKSYA 60
SEQ ID NO:6 Thermotoga maritima      -----------MKGYFGPYGGQYVPEILMPALEELEAAYEEIMKDESFWKEFNDLLRDYA 49
SEQ ID NO:8 Escherichia coli         -------MTTLLNPYFGEFGGMYVPQILMPALRQLEEAFVSAQKDPEFQAQFNDLLKNYA 53
                                         ** :** :**: *:  *.:** *:    .* .*  .::  *: :*

   MUTATIONS                                     V                          L        G
Pyrococcus furiosus         GRPTPLYYAKRLTEKIGGAKIYLKREDLVHGGAHKTNNAIGQALLAKFMGKTRLIAETGA 107
Archaeoglobus fulgidus      GRPTPLYFAENLSREL-GVKIYLKREDLLHGGAHKINNTIGQALLAKFMGKKRVIAETGA 119
Thermotoga maritima         GRPTPLYFARRLSEKY-GARIYLKREDLLHTGAHKINNAIGQVLLAKKMGKTRIIAETGA 108
Escherichia coli            GRPTALTKCQNITAGT-NTTLYLKREDLLHGGAHKTNQVLGQALLAKRMGKTEIIAETGA 112
                            **** *  ...::     . :*******:* **** *:.:**.**** ***..:******

   MUTATIONS                                               L                          D
Pyrococcus furiosus         GQHGVATAMAGALLGMKVDIYMGAEDVERQKMNVFRMKLLGANVIPVNSGSRTLKDAINE 167
Archaeoglobus fulgidus      GQHGVATAMAAALLGLEAEIYMGAEDYERQKMNVFRMELLGAKVTAVESGSRTLKDAINE 179
Thermotoga maritima         GQHGVATATAAALFGMECVIYMGEEDTIRQKPNVERMKLLGAKVVPVKSGSRTLKDAINE 168
Escherichia coli            GQHGVASALASALLGLKCRIYMGAKDVERQSPNVFRMRLMGAEVIPVHSGSATLKDACNE 172
                            ******:* *.**:*::  **** :*  **. ** **.*:**:*  *.*** ***** **

   MUTATIONS                               F  A                         P
Pyrococcus furiosus         ALRDWVATFEYTHYLIGSVVGPHPYPTIVRDFQSVIGREAKAQILEAEGQLPDVIVACVG 227
Archaeoglobus fulgidus      ALRDWVESFEHTHYLIGSVVGPHPFPTIVRDFQAVIGKEARRQIIEAEGGMPDAIIACVG 239
Thermotoga maritima         ALRDWITNLQTTYYVIGSVVGPHPYPIIVRNFQKVIGEETKKQILEKEGRLPDYIVACVG 228
Escherichia coli            ALRDWSGSYETAHYMLGTAAGPHPYPTIVREFQRMIGEETKAQILEREGRLPDAVIACVG 232
                            *****   . : ::*::*:..****:* ***:** :**.*:: **:* ** :** ::****

   MUTATIONS                                                              S
Pyrococcus furiosus         GGSNAMGIFYPFVNDKKVKLVGVEAGGKGLESGKHSASLNAGQVGVFHGMLSYFLQDEEG 287
Archaeoglobus fulgidus      GGSNAMGIFHPFLND-DVRLIGVEAGGEGIESGRHSASLTAGSKGVLHGMLSYFLQDEEG 298
Thermotoga maritima         GGSNAAGIFYPFIDS-GVKLIGVEAGGEGLETGKHAASLLKGKIGYLHGSKTFVLQDDWG 287
Escherichia coli            GGSNAIGMFADFINETNVGLIGVEPGGHGIETGEHGAPLKHGRVGIYFGMKAPMMQTEDG 292
                            ***** *:*  *::.  * *:*** **.*:*:*.*.* *  *  *  .*  : .:* : *
```

FIG. 2

```
MUTATIONS                                    S                                                                    A
Pyrococcus furiosus      QIKPTHSIAPGLDYPGVGPEHAYLKKIQRAEYVTVTDEEALKAFHELSRTEGIIPALESA 347
Archaeoglobus fulgidus   MMLDTHSVSAGLDYPGVGPEHAYLKETGRCEYVTVNDEEALRAFKTLSKLEGIIPALESA 358
Thermotoga maritima      QVQVTHSVSAGLDYSGVGPEHAYWRETGKVLYDAVTDEEALDAFIELSRLEGIIPALESS 347
Escherichia coli         QIEESYSISAGLDFPSVGPQHAYLNSTGRADYVSITDDEALEAFKTLCLHEGIIPALESS 352
                          ::**: .****:  .*  *****    *  :   .::**  **  **.**********:

                                                                                    A
MUTATIONS
Pyrococcus furiosus      HAVAYAMKLAKE-MSRDEIIIVNLSGRGDKDLDIVLKVSGNV----- 388
Archaeoglobus fulgidus   HAIAYAMKMAEE-MQRDDVLVVNLSGRGDKDKDMDIVRRLA------ 397
Thermotoga maritima      HALALYLKKIN----IKGKVVVVNLSGRGDKDLESVLNHPYVRERIR 389
Escherichia coli         HALAHALKMMRENPDKEQLIVVNLSGRGDKDIFTVHDILKARGEI-  397
                         **:    :  :  : ::::***********:         *
```

FIG. 2 (continued)

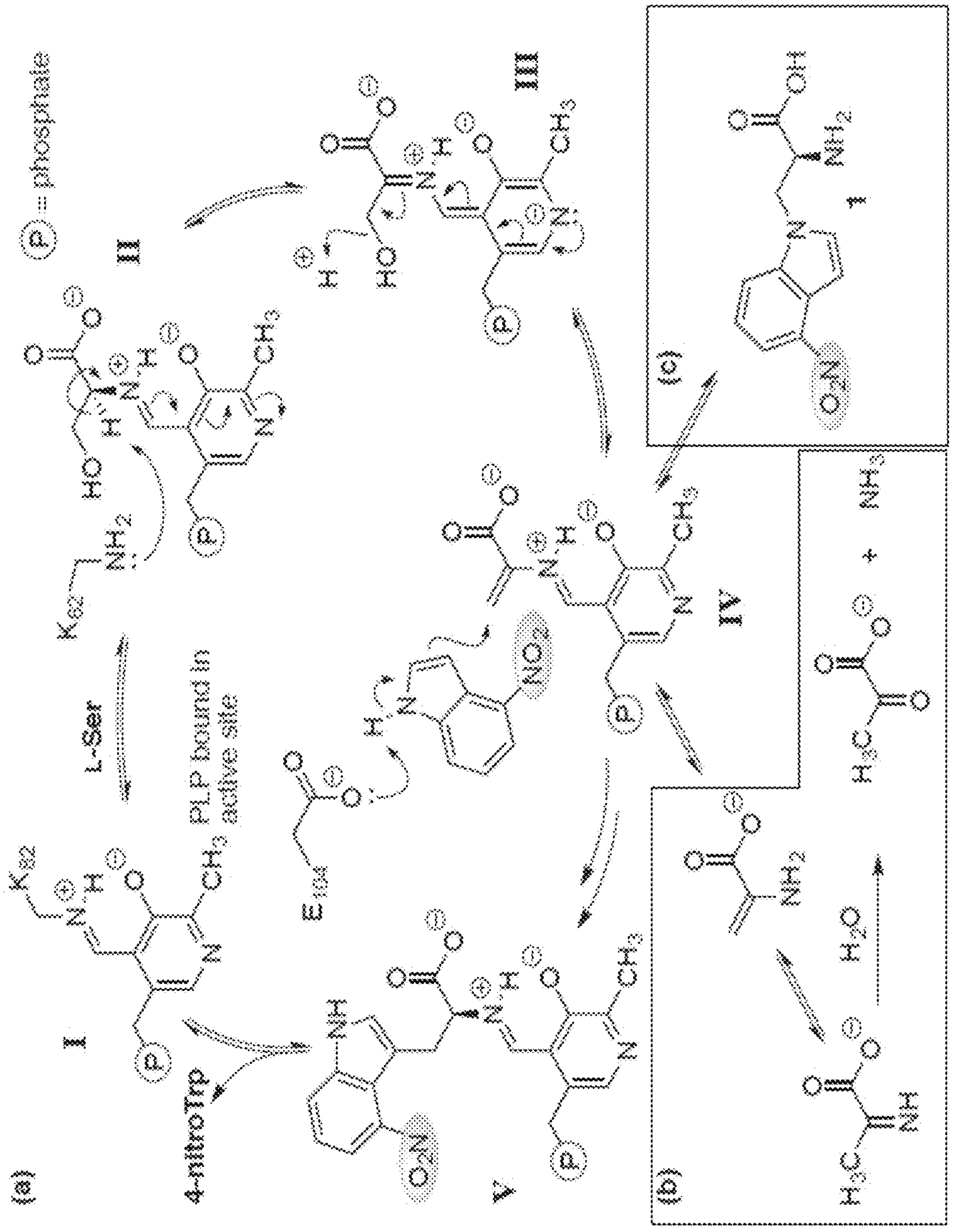
FIG. 4A-C

SEQUENCE LISTING

```
Sequence total quantity: 26
SEQ ID NO: 1            moltype = DNA  length = 1191
FEATURE                 Location/Qualifiers
source                  1..1191
                        mol_type = other DNA
                        organism = Pyrococcus furiosus
CDS                     1..1191
                        protein_id = 2
                        transl_table = 1
                        translation = MWFGEFGGQYVPETLIEPLKELEKAYKRFKDDEEFNRQLNYYLKTW
                         AGRPTPLYYAKRLTEKIGGAKIYLKREDLVHGGAHKTNNAIGQALLAKFMGKTRLIAET
                         GAGQHGVATAMAGALLGMKVDIYMGAEDVERQKMNVFRMKLLGANVIPVNSGSRTLKDA
                         INEALRDWVATFEYTHYLIGSVVGPHPYPTIVRDFQSVIGREAKAQILEAEGQLPDVIV
                         ACVGGGSNAMGIFYPFVNDKKVKLVGVEAGGKGLESGKHSASLNAGQVGVFHGMLSYFL
                         QDEEGQIKPTHSIAPGLDYPGVGPEHAYLKKIQRAEYVTVTDEEALKAFHELSRTEGII
                         PALESAHAVAYAMKLAKEMSRDEIIIVNLSGRGDKDLDIVLKVSGNVLEHHHHHH
SEQUENCE: 1
atgtggttcg gtgaatttgg tggtcagtac gtgccagaaa cgctgattga accgctgaaa  60
gagctggaaa aagcttacaa acgtttcaaa gatgacgaag aattcaatcg tcaactgaat  120
tactacctga aaacctgggc aggtcgtcca accccactgt actacgcaaa acgcctgact  180
gaaaaaatcg gtggtgctaa aatctacctg aaacgtgaag acctggttca cggtggtgca  240
cacaagacca acaacgccat cggtcaggca ctgctggcaa agttcatggg taaaactcgt  300
ctgatcgctg agaccggtgc tggtcagcac ggcgtagcga ctgcaatggc tggtgcactg  360
ctgggcatga aagtggacat ttacatgggt gctgaggacg tagaacgtca gaaaatgaac  420
gtattccgta tgaagctgct gggtgcaaac gtaattccag ttaactccgg ttctcgcacc  480
ctgaaagacg caatcaacga ggctctgcgt gattgggtgg ctacttttga atacacccac  540
tacctgatcg gttccgtggt cggtccacat ccgtatccga ccatcgttcg tgattttcag  600
tctgttatcg gtcgtgaggc taaagcgcag atcctggagg ctgaaggtca gctgccagat  660
gtaatcgttg cttgtgttgg tggtggctct aacgcgatgg gtatctttta cccgttcgtg  720
aacgacaaaa aagttaagct ggttggcgtt gaggctggtg gtaaaggcct ggaatctggt  780
aagcattccg ctagcctgaa cgcaggtcag gttggtgtgt tccatggcat gctgtcctac  840
tttctgcagg acgaagaagg tcagatcaaa ccaactcact ccatcgcacc aggtctggat  900
tatccaggtg ttggtccaga acacgcttac ctgaaaaaaa ttcagcgtgc tgaatacgtg  960
actgtaaccg atgaagaagc actgaaagcg ttccatgaac tgagccgtac cgaaggtatc  1020
atcccagctc tggaatctgc gcatgctgtg gcttacgcta tgaaactggc taaggaaatg  1080
tctcgtgatg agatcatcat cgtaaacctg tctggtcgtg gtgacaaaga cctggatatt  1140
gttctgaaag tgtctggcaa cgtgctcgag caccatcacc atcaccattg a           1191

SEQ ID NO: 2            moltype = AA  length = 396
FEATURE                 Location/Qualifiers
source                  1..396
                        mol_type = protein
                        organism = Pyrococcus furiosus
SEQUENCE: 2
MWFGEFGGQY VPETLIEPLK ELEKAYKRFK DDEEFNRQLN YYLKTWAGRP TPLYYAKRLT  60
EKIGGAKIYL KREDLVHGGA HKTNNAIGQA LLAKFMGKTR LIAETGAGQH GVATAMAGAL  120
LGMKVDIYMG AEDVERQKMN VFRMKLLGAN VIPVNSGSRT LKDAINEALR DWVATFEYTH  180
YLIGSVVGPH PYPTIVRDFQ SVIGREAKAQ ILEAEGQLPD VIVACVGGGS NAMGIFYPFV  240
NDKKVKLVGV EAGGKGLESG KHSASLNAGQ VGVFHGMLSY FLQDEEGQIK PTHSIAPGLD  300
YPGVGPEHAY LKKIQRAEYV TVTDEEALKA FHELSRTEGI IPALESAHAV AYAMKLAKEM  360
SRDEIIIVNL SGRGDKDLDI VLKVSGNVLE HHHHHH                            396

SEQ ID NO: 3            moltype = DNA  length = 1218
FEATURE                 Location/Qualifiers
source                  1..1218
                        mol_type = other DNA
                        organism = Archaeoglobus fulgidus
CDS                     1..1218
                        protein_id = 4
                        transl_table = 1
                        translation = MRCWLENLSGGRKMKFGEFGGRFVPEVLIPPLEELEKAYDRFKDDE
                         EFKARLEYYLKSYAGRPTPLYFAENLSRELGVKIYLKREDLLHGGAHKINNTIGQALLA
                         KFMGKKRVIAETGAGQHGVATAMAAALLGLEAEIYMGAEDYERQKMNVFRMELLGAKVT
                         AVESGSRTLKDAINEALRDWVESFEHTHYLIGSVVGPHPFPTIVRDFQAVIGKEARRQI
                         IEAEGGMPDAIIACVGGGSNAMGIFHPFLNDDVRLIGVEAGGEGIESGRHSASLTAGSK
                         GVLHGMLSYFLQDEEGMMLDTHSVSAGLDYPGVGPEHAYLKETGRCEYVTVNDEEALRA
                         FKTLSKLEGIIPALESAHAIAYAMKMAEEMQRDDVLVVNLSGRGDKDMDIVRRRLALEH
                         HHHHH
SEQUENCE: 3
atgcgttgct ggctggaaaa cctgtctggc ggtcgtaaaa tgaagtttgg tgagtttggc  60
ggtcgtttcg ttccggaggt actgatccca ccgctggaag aactggaaaa agcatatgac  120
cgctttaaag atgatgagga atttaaagca cgtctggaat actacctgaa atcctatgca  180
ggtcgtccga ccccactgta cttcgctgag aacctgagcc gtgaactggg cgtcaaaatc  240
tatctgaaac gcgaagacct gctgcatggt ggtgcgcaca aaatcaacaa taccatcggt  300
caagcgctgc tggcgaaatt catgggtaaa aagcgtgtta ttgcggaaac cggtgcaggt  360
cagcacggtg tggcgactgc gatggctgcg gcactgctgg gcctggaagc ggaaatttat  420
atgggtgctg aagactatga gcgccaaaaa atgaacgtgt ttcgtatgga actgctgggt  480
gccaaagtca ccgctgtaga aagcggttcc cgtaccctga aagacgcaat caacgaggca  540
```

ctgcgtgact gggtggaatc tttcgaacac actcactacc tgatcggttc tgtagtaggt 600
ccgcatccgt tcccgactat cgtccgcgac ttccaagctg tgatcggcaa ggaggcacgc 660
cgtcagatca tcgaagcgga aggtggtatg ccggatgcta tcatcgcgtg cgtaggcggt 720
ggctccaacg ctatgggcat cttccacccg ttcctgaacg acgacgtacg tctgattggt 780
gtagaagctg gcggtgaagg tatcgaatct ggtcgtcatt ccgcaagcct gaccgctggc 840
tctaaaggtg ttctgcacgg tatgctgagc tatttcctgc aggacgaaga gggtatgatg 900
ctggacaccc actccgtatc tgcaggtctg gattatccgg gtgttggtcc ggaacacgcc 960
tacctgaagg aaacgggtcg ttgtgagtac gttaccgtaa atgacgaaga agcgctgcgt 1020
gctttcaaaa ccctgtccaa actggaaggt atcattcctg cgctggaatc cgctcacgcc 1080
attgcatatg ctatgaaaat ggccgaggaa atgcagcgtg atgatgtgct ggttgtaaac 1140
ctgtccggtc gtggcgataa agatatggac atcgtacgtc gtcgtctggc tctcgagcac 1200
caccaccacc accactga 1218

SEQ ID NO: 4 moltype = AA length = 405
FEATURE Location/Qualifiers
source 1..405
mol_type = protein
organism = Archaeoglobus fulgidus
SEQUENCE: 4
MRCWLENLSG GRKMKFGEFG GRFVPEVLIP PLEELEKAYD RFKDDEEFKA RLEYYLKSYA 60
GRPTPLYFAE NLSRELGVKI YLKREDLLHG GAHKINNTIG QALLAKFMGK KRVIAETGAG 120
QHGVATAMAA ALLGLEAEIY MGAEDYERQK MNVFRMELLG AKVTAVESGS RTLKDAINEA 180
LRDWVESFEH THYLIGSVVG PHPFPTIVRD FQAVIGKEAR RQIIEAEGGM PDAIIACVGG 240
GSNAMGIFHP FLNDDVRLIG VEAGGEGIES GRHSASLTAG SKGVLHGMLS YFLQDEEGMM 300
LDTHSVSAGL DYPGVGPEHA YLKETGRCEY VTVNDEEALR AFKTLSKLEG IIPALESAHA 360
IAYAMKMAEE MQRDDVLVVN LSGRGDKDMD IVRRRLALEH HHHHH 405

SEQ ID NO: 5 moltype = DNA length = 1194
FEATURE Location/Qualifiers
source 1..1194
mol_type = other DNA
organism = Thermotoga maritima
CDS 1..1194
protein_id = 6
transl_table = 1
translation = MKGYFGPYGGQYVPEILMPALEELEAAYEEIMKDESFWKEFNDLLR
DYAGRPTPLYFARRLSEKYGARIYLKREDLLHTGAHKINNAIGQVLLAKKMGKTRIIAE
TGAGQHGVATATAAALFGMECVIYMGEEDTIRQKPNVERMKLLGAKVVPVKSGSRTLKD
AINEALRDWITNLQTTYYVIGSVVGPHPYPIIVRNFQKVIGEETKKQILEKEGRLPDYI
VACVGGGSNAAGIFYPFIDSGVKLIGVEAGGEGLETGKHAASLLKGKIGYLHGSKTFVL
QDDWGQVQVTHSVSAGLDYSGVGPEHAYWRETGKVLYDAVTDEEALDAFIELSRLEGII
PALESSHALAYLKKINIKGKVVVVNLSGRGDKDLESVLNHPYVRERIRLEHHHHHH
SEQUENCE: 5
atgaaaggct acttcggtcc gtacggtggc cagtacgtgc cggaaatcct gatgccagct 60
ctggaagaac tggaagctgc gtacgaagaa atcatgaaag atgagtcttt ctggaaagaa 120
ttcaatgacc tgctgcgcga ttatgcgggt cgtccgactc cgctgtactt cgcacgtcgt 180
ctgtccgaaa aatacggtgc tcgcatctat ctgaaacgtg aagacctgct gcatactggt 240
gcgcataaaa tcaataacgc tatcggccag gttctgctgg caaaaaaaat gggcaaaacc 300
cgtatcattg ctgaaacggg tgctggtcag cacggcgtag caactgctac cgcagcagcg 360
ctgttcggta tggaatgtgt aatctatatg ggcgaagaag acacgatccg ccagaaaccg 420
aacgttgaac gtatgaaact gctgggtgct aaagttgtac cggtaaaatc cggtagccgt 480
accctgaaag acgcaattaa cgaagctctg cgtgactgga ttaccaacct gcagaccacc 540
tattacgtga tcggctctgt ggttggtccg catccatatc cgattatcgt acgtaacttc 600
caaaaggtta tcggcgaaga gaccaaaaaa cagattctgg aaaaagaagg ccgtctgccg 660
gactacatcg ttgcgtgcgt gggtggtggt tctaacgctg ccggtatctt ctatccgttt 720
atcgattctg gtgtgaagct gatcggcgta gaagccggtg gcgaaggtct ggaaaccggt 780
aaacatgcgg cttctctgct gaaaggtaaa atcggctacc tgcacggttc taagacgttc 840
gttctgcagg atgactgggg tcaagttcag gtgacgcact ccgtctccgc tggcctggac 900
tactccggtg tcggtccgga acacgcctat tggcgtgaga ccggtaaagt gctgtacgat 960
gctgtgaccg atgaagaagc tctggacgca ttcatcgaac tgtctcgcct ggaaggcatc 1020
atcccagccc tggagtcttc tcacgcactg gcttatctga agaagatcaa catcaagggt 1080
aaagttgtgg tggttaatct gtctggtcgt ggtgacaagg atctggaatc tgtactgaac 1140
cacccgtatg ttcgcgaacg catccgcctc gagcaccacc accaccacca ctga 1194

SEQ ID NO: 6 moltype = AA length = 397
FEATURE Location/Qualifiers
source 1..397
mol_type = protein
organism = Thermotoga maritima
SEQUENCE: 6
MKGYFGPYGG QYVPEILMPA LEELEAAYEE IMKDESFWKE FNDLLRDYAG RPTPLYFARR 60
LSEKYGARIY LKREDLLHTG AHKINNAIGQ VLLAKKMGKT RIIAETGAGQ HGVATATAAA 120
LFGMECVIYM GEEDTIRQKP NVERMKLLGA KVVPVKSGSR TLKDAINEAL RDWITNLQTT 180
YYVIGSVVGP HPYPIIVRNF QKVIGEETKK QILEKEGRLP DYIVACVGGG SNAAGIFYPF 240
IDSGVKLIGV EAGGEGLETG KHAASLLKGK IGYLHGSKTF VLQDDWGQVQ VTHSVSAGLD 300
YSGVGPEHAY WRETGKVLYD AVTDEEALDA FIELSRLEGI IPALESSHAL AYLKKINIKG 360
KVVVVNLSGR GDKDLESVLN HPYVRERIRL EHHHHHH 397

SEQ ID NO: 7 moltype = DNA length = 1218

-continued

```
FEATURE                 Location/Qualifiers
source                  1..1218
                        mol_type = other DNA
                        organism = Escherichia coli
CDS                     1..1218
                        protein_id = 8
                        transl_table = 1
                        translation = MTTLLNPYFGEFGGMYVPQILMPALRQLEEAFVSAQKDPEFQAQFN
                         DLLKNYAGRPTALTKCQNITAGTNTTLYLKREDLLHGGAHKTNQVLGQALLAKRMGKTE
                         IIAETGAGQHGVASALASALLGLKCRIYMGAKDVERQSPNVFRMRLMGAEVIPVHSGSA
                         TLKDACNEALRDWSGSYETAHYMLGTAAGPHPYPTIVREFQRMIGEETKAQILEREGRL
                         PDAVIACVGGGSNAIGMFADFINETNVGLIGVEPGGHGIETGEHGAPLKHGRVGIYFGM
                         KAPMMQTEDGQIEESYSISAGLDFPSVGPQHAYLNSTGRADYVSITDDEALEAFKTLCL
                         HEGIIPALESSHALAHALKMMRENPDKEQLLVVNLSGRGDKDIFTVHDILKARGEILEH
                         HHHHH
SEQUENCE: 7
atgactactc tgctgaaccc gtacttcggt gagttcggtg gtatgtacgt gccacagatc  60
ctgatgcctg cgctgcgcca gctggaggag gcgtttgtta gcgcccagaa agatccggag  120
ttccaggctc agttcaacga cctgctgaaa aactatgctg gtcgtccgac cgcgctgacg  180
aaatgccaga acatcactgc tggtacgaac accaccctgt acctgaagcg tgaggacctg  240
ctgcatggtg gtgcgcacaa aaccaaccag gtcctgggtc aagcactgct ggcaaaacgt  300
atgggcaaaa ctgaaattat tgcggaaacg ggtgcaggtc agcacggtgt agcttctgcg  360
ctggccagcg cactgctggg tctgaagtgt cgtatctata tgggtgcgaa agatgtggag  420
cgtcagtctc cgaacgtatt ccgcatgcgt ctgatgggtg cagaagtgat cccggtacac  480
tctggttccg caactctgaa agacgcatgt aatgaagcac tgcgtgactg gtccggttct  540
tatgaaactg ctcactacat gctgggcacc gcagctggtc ctcacccgta cccgaccatc  600
gtacgtgaat tccagcgcat gattggtgaa gaaaccaaag cgcagatcct ggaacgtgaa  660
ggtcgcctgc cagatgcggt gatcgcgtgc gtaggtggtg gttccaacgc gatcggtatg  720
ttcgctgatt tcatcaacga aaccaacgtt ggcctgattg gtgtagaacc aggtggccac  780
ggcattgaaa ctggcgagca cggtgcacct ctgaaacacg gtcgcgtagg catttacttc  840
ggtatgaaag ctccgatgat gcagactgaa gacggtcaga tcgaagaatc ttactccatt  900
tctgcaggtc tggacttccc gtctgttggt ccgcaacacg catatctgaa ctctaccggt  960
cgtgcggact acgtgtctat cactgacgac gaggctctgg aggcctttaa aactctgtgc  1020
ctgcacgaag gtatcattcc agctctggaa tccagccacg cactggcaca cgcactgaaa  1080
atgatgcgtg aaaacccaga caaagaacag ctgctggtgg ttaacctgag cggtcgtggt  1140
gacaaggata tcttcacggt tcacgacatc ctgaaggctc gtggtgaaat cctcgagcac  1200
caccaccacc accactga                                                1218

SEQ ID NO: 8            moltype = AA  length = 405
FEATURE                 Location/Qualifiers
source                  1..405
                        mol_type = protein
                        organism = Escherichia coli
SEQUENCE: 8
MTTLLNPYFG EFGGMYVPQI LMPALRQLEE AFVSAQKDPE FQAQFNDLLK NYAGRPTALT  60
KCQNITAGTN TTLYLKREDL LHGGAHKTNQ VLGQALLAKR MGKTEIIAET GAGQHGVASA  120
LASALLGLKC RIYMGAKDVE RQSPNVFRMR LMGAEVIPVH SGSATLKDAC NEALRDWSGS  180
YETAHYMLGT AAGPHPYPTI VREFQRMIGE ETKAQILERE GRLPDAVIAC VGGGSNAIGM  240
FADFINETNV GLIGVEPGGH GIETGEHGAP LKHGRVGIYF GMKAPMMQTE DGQIEESYSI  300
SAGLDFPSVG PQHAYLNSTG RADYVSITDD EALEAFKTLC LHEGIIPALE SSHALAHALK  360
MMRENPDKEQ LLVVNLSGRG DKDIFTVHDI LKARGEILEH HHHHH                  405

SEQ ID NO: 9            moltype = DNA  length = 1191
FEATURE                 Location/Qualifiers
source                  1..1191
                        mol_type = other DNA
                        organism = synthetic construct
CDS                     1..1191
                        protein_id = 10
                        transl_table = 1
                        translation = MWFGEFGGQYVPETLVGPLKELEKAYKRFKDDEEFNRQLNYYLKTW
                         AGRPTPLYYAKRLTEKIGGAKVYLKREDLVHGGAHKTNNAIGQALLAKLMGKTRLIAET
                         GAGQHGVATAMAGALLGMKVDIYMGAEDVERQKMNVFRMKLLGANVIPVNSGSRTLKDA
                         INEALRDWVATFEYTHYLIGSVVGPHPYPTIVRDFQSVIGREAKAQILEAEGQLPDVIV
                         ACVGGGSNAMGIFYPFVNDKKVKLVGVEAGGKGLESGKHSASLNAGQVGVSHGMLSYFL
                         QDEEGQIKPSHSIAPGLDYPGVGPEHAYLKKIQRAEYVAVTDEEALKAFHELSRTEGII
                         PALESAHAVAYAMKLAKEMSRDEIIIVNLSGRGDKDLDIVLKASGNVLEHHHHHH
misc_feature            1..1191
                        note = PfTrpB2B9
SEQUENCE: 9
atgtggttcg gtgaatttgg tggtcagtac gtgccagaaa cgctggttgg accccctgaaa  60
gagctggaaa aagcttacaa acgtttcaaa gatgacgaag aattcaatcg tcagctgaat  120
tactacctga aaacctgggc aggtcgtcca accccactgt actacgcaaa acgcctgact  180
gaaaaaatcg gtggtgctaa agtctacctg aaacgtgaag acctggttca cggtggtgca  240
cacaagacca acaacgccat cggtcaggca ctgctggcaa agctcatggg taaaactcgt  300
ctgatcgctg agaccggtgc tggtcagcac ggcgtagcga ctgcaatggc tggtgcactg  360
ctgggcatga aagtggacat ttacatgggt gctgaggacg tagaacgtca gaaaatgaac  420
gtattccgta tgaagctgct gggtgcaaac gtaattccag ttaactccgg ttctcgcacc  480
ctgaaagacg caatcaacga ggctctgcgt gattgggtgg ctacttttga atacacccac  540
```

-continued

```
tacctaatcg gttccgtggt cggtccacat ccgtatccga ccatcgttcg tgattttcag  600
tctgttatcg gtcgtgaggc taaagcgcag atcctggagg ctgaaggtca gctgccagat  660
gtaatcgttg cttgtgttgg tggtggctct aacgcgatgg gtatctttta cccgttcgtg  720
aacgacaaaa aagttaagct ggttggcgtt gaggctggtg gtaaaggcct ggaatctggt  780
aagcattccg ctagcctgaa cgcaggtcag gttggtgtgt cccatggcat gctgtcctac  840
tttctgcagg acgaagaagg tcagatcaaa ccaagccact ccatcgcacc aggtctggat  900
tatccaggtg ttggtccaga acacgcttac ctgaaaaaaa ttcagcgtgc tgaatacgtg  960
gctgtaaccg atgaagaagc actgaaagcg ttccatgaac tgagccgtac cgaaggtatc  1020
atcccagctc tggaatctgc gcatgctgtg gcttacgcta tgaaactggc taaggaaatg  1080
tctcgtgatg agatcatcat cgtaaacctg tctggtcgtg gtgacaaaga cctggatatt  1140
gtcctgaaag cgtctggcaa cgtgctcgag caccaccacc accaccactg a           1191

SEQ ID NO: 10          moltype = AA  length = 396
FEATURE                Location/Qualifiers
source                 1..396
                       mol_type = protein
                       organism = synthetic construct
SEQUENCE: 10
MWFGEFGGQY VPETLVGPLK ELEKAYKRFK DDEEFNRQLN YYLKTWAGRP TPLYYAKRLT  60
EKIGGAKVYL KREDLVHGGA HKTNNAIGQA LLAKLMGKTR LIAETGAGQH GVATAMAGAL  120
LGMKVDIYMG AEDVERQKMN VFRMKLLGAN VIPVNSGSRT LKDAINEALR DWVATFEYTH  180
YLIGSVVGPH PYPTIVRDFQ SVIGREAKAQ ILEAEGQLPD VIVACVGGGS NAMGIFYPFV  240
NDKKVKLVGV EAGGKGLESG KHSASLNAGQ VGVSHGMLSY FLQDEEGQIK PSHSIAPGLD  300
YPGVGPEHAY LKKIQRAEYV AVTDEEALKA FHELSRTEGI IPALESAHAV AYAMKLAKEM  360
SRDEIIIVNL SGRGDKDLDI VLKASGNVLE HHHHHH                            396

SEQ ID NO: 11          moltype = DNA  length = 1164
FEATURE                Location/Qualifiers
source                 1..1164
                       mol_type = other DNA
                       organism = synthetic construct
CDS                    1..1164
                       protein_id = 12
                       transl_table = 1
                       translation = MWFGEFGGQYVPETLVGPLKELEKAYKRFKDDEEFNRQLNYYLKTW
                        AGRPTPLYYAKRLTEKIGGAKVYLKREDLVHGGAHKTNNAIGQALLAKLMGKTRLIAET
                        GAGQHGVATAMAGALLGMKVDIYMGAEDVERQKMNVFRMKLLGANVIPVNSGSRTVKDA
                        INEALRDWVATFEYTHYLIGSVVGPHPYPTIVRDFQSVIGREAKAQILEAEGQLPDVIV
                        ACVGGGSNAMGIFYPFVNDKKVKLVGVEAGGKGLESGKHSASLNAGQVGVSHGMLSYFL
                        QDEEGQIKPSHSIAPGLDYPGVGPEHAYLKKIQRAEYVAVTDEEALKAFHELSRTEGII
                        PALESAHAVAYAMKLAKEMSRDEIIIVNLSGRGDKDLDIVLKASGNV
misc_feature           1..1164
                       note = Pf2B9 L161V
SEQUENCE: 11
atgtggttcg gtgaatttgg tggtcagtac gtgccagaaa cgctggttgg acccctgaaa  60
gagctggaaa aagcttacaa acgtttcaaa gatgacgaag aattcaatcg tcagctgaat  120
tactacctga aaacctgggc aggtcgtcca accccactgt actacgcaaa acgcctgact  180
gaaaaaatcg gtggtgctaa agtctacctg aaacgtgaag acctggttca cggtggtgca  240
cacaagacca acaacgccat cggtcaggca ctgctggcaa agctcatggg taaaactcgt  300
ctgatcgctg agaccggtgc tggtcagcac ggcgtagcga ctgcaatggc tggtgcactg  360
ctgggcatga aagtggacat ttacatgggt gctgaggacg tagaacgtca gaaaatgaac  420
gtattccgta tgaagctgct gggtgcaaac gtaattccag ttaactccgg ttctcgcacc  480
gtgaaagacg caatcaacga ggctctgcgt gattgggtgg ctacttttga atacacccac  540
tacctaatcg gttccgtggt cggtccacat ccgtatccga ccatcgttcg tgattttcag  600
tctgttatcg gtcgtgaggc taaagcgcag atcctggagg ctgaaggtca gctgccagat  660
gtaatcgttg cttgtgttgg tggtggctct aacgcgatgg gtatctttta cccgttcgtg  720
aacgacaaaa aagttaagct ggttggcgtt gaggctggtg gtaaaggcct ggaatctggt  780
aagcattccg ctagcctgaa cgcaggtcag gttggtgtgt cccatggcat gctgtcctac  840
tttctgcagg acgaagaagg tcagatcaaa ccaagccact ccatcgcacc aggtctggat  900
tatccaggtg ttggtccaga acacgcttac ctgaaaaaaa ttcagcgtgc tgaatacgtg  960
gctgtaaccg atgaagaagc actgaaagcg ttccatgaac tgagccgtac cgaaggtatc  1020
atcccagctc tggaatctgc gcatgctgtg gcttacgcta tgaaactggc taaggaaatg  1080
tctcgtgatg agatcatcat cgtaaacctg tctggtcgtg gtgacaaaga cctggatatt  1140
gtcctgaaag cgtctggcaa cgtg                                         1164

SEQ ID NO: 12          moltype = AA  length = 388
FEATURE                Location/Qualifiers
source                 1..388
                       mol_type = protein
                       organism = synthetic construct
SEQUENCE: 12
MWFGEFGGQY VPETLVGPLK ELEKAYKRFK DDEEFNRQLN YYLKTWAGRP TPLYYAKRLT  60
EKIGGAKVYL KREDLVHGGA HKTNNAIGQA LLAKLMGKTR LIAETGAGQH GVATAMAGAL  120
LGMKVDIYMG AEDVERQKMN VFRMKLLGAN VIPVNSGSRT VKDAINEALR DWVATFEYTH  180
YLIGSVVGPH PYPTIVRDFQ SVIGREAKAQ ILEAEGQLPD VIVACVGGGS NAMGIFYPFV  240
NDKKVKLVGV EAGGKGLESG KHSASLNAGQ VGVSHGMLSY FLQDEEGQIK PSHSIAPGLD  300
YPGVGPEHAY LKKIQRAEYV AVTDEEALKA FHELSRTEGI IPALESAHAV AYAMKLAKEM  360
SRDEIIIVNL SGRGDKDLDI VLKASGNV                                     388
```

```
SEQ ID NO: 13          moltype = DNA  length = 1164
FEATURE                Location/Qualifiers
source                 1..1164
                       mol_type = other DNA
                       organism = synthetic construct
CDS                    1..1164
                       protein_id = 14
                       transl_table = 1
                       translation = MWFGEFGGQYVPETLVGPLKELEKAYKRFKDDEEFNRQLNYYLKTW
                        AGRPTPLYYAKRLTEKIGGAKVYLKREDLVHGGAHKTNNAIGQALLAKLMGKTRLIAET
                        GAGQHGVATAMAGALLGMKVDIYMGAEDVERQKLNVFRMKLLGANVIPVNSGSRTLKDA
                        IDEALRDWVATFEYTHYLIGSVVGPHPYPTIVRDFQSVIGREAKAQIPEAEGQLPDVIV
                        ACVGGGSNAMGIFYPFVNDKKVKLVGVEAGGKGLESGKHSASLNAGQVGVSHGMLSYFL
                        QDEEGQIKPSHSIAPGLDYPGVGPEHAYLKKIQRAEYVAVTDEEALKAFHELSRTEGII
                        PALESAHAVAYAMKLAKEMSRDEIIIVNLSGRGDKDLDIVLKASGNV
misc_feature           1..1164
                       note = Pf5G8
SEQUENCE: 13
atgtggttcg gtgaatttgg tggtcagtac gtgccagaaa cgctggttgg acccctgaaa  60
gagctggaaa aagcttacaa acgtttcaaa gatgacgaag aattcaatcg tcagctgaat  120
tactacctga aaacctgggc aggtcgtcca accccactgt actacgcaaa acgcctgact  180
gaaaaaatcg gtggtgctaa agtctacctg aaacgtgaag acctggttca cggtggtgca  240
cacaagacca acaacgccat cggtcaggca ctgctggcaa agctcatggg taaaactcgt  300
ctgatcgctg agaccggtgc tggtcagcac ggcgtagcga ctgcaatggc tggtgcactg  360
ctgggcatga aagtggacat ttacatgggt gctgaggacg tagaacgtca gaaattgaac  420
gtattccgta tgaagctgct gggtgcaaac gtaattccag ttaactccgg ttctcgcacc  480
ctgaaagacg caatcgacga ggctctgcgt gattgggtgg ctacttttga atacacccac  540
tacctaatcg gttccgtggt cggtccacat ccgtatccga ccatcgttcg tgattttcag  600
tctgttatcg gtcgtgaggc taaagcgcag atcccggagg ctgaaggtca gctgccagat  660
gtaatcgttg cttgtgttgg tggtggctct aacgcgatgg gtatctttta cccgttcgtg  720
aacgacaaaa aagttaagct ggttggcgtt gaggctggtg gtaaaggcct ggaatctggt  780
aagcattccg ctagcctgaa cgcaggtcag gttggtgtgt cccatggcat gctgtcctac  840
tttctgcagg acgaagaagg tcagatcaaa ccaagccact ccatcgcacc aggtctggat  900
tatccaggtg ttggtccaga acacgcttac ctgaaaaaaa ttcagcgtgc tgaatacgtg  960
gctgtaaccg atgaagaagc actgaaagcg ttccatgaac tgagccgtac cgaaggtatc  1020
atcccagctc tggaatctgc gcatgctgtg gcttacgcta tgaaactggc taaggaaatg  1080
tctcgtgatg agatcatcat cgtaaacctg tctggtcgtg gtgacaaaga cctggatatt  1140
gtcctgaaag cgtctggcaa cgtg                                        1164

SEQ ID NO: 14          moltype = AA  length = 388
FEATURE                Location/Qualifiers
source                 1..388
                       mol_type = protein
                       organism = synthetic construct
SEQUENCE: 14
MWFGEFGGQY VPETLVGPLK ELEKAYKRFK DDEEFNRQLN YYLKTWAGRP TPLYYAKRLT  60
EKIGGAKVYL KREDLVHGGA HKTNNAIGQA LLAKLMGKTR LIAETGAGQH GVATAMAGAL  120
LGMKVDIYMG AEDVERQKLN VFRMKLLGAN VIPVNSGSRT LKDAIDEALR DWVATFEYTH  180
YLIGSVVGPH PYPTIVRDFQ SVIGREAKAQ IPEAEGQLPD VIVACVGGGS NAMGIFYPFV  240
NDKKVKLVGV EAGGKGLESG KHSASLNAGQ VGVSHGMLSY FLQDEEGQIK PSHSIAPGLD  300
YPGVGPEHAY LKKIQRAEYV AVTDEEALKA FHELSRTEGI IPALESAHAV AYAMKLAKEM  360
SRDEIIIVNL SGRGDKDLDI VLKASGNV                                    388

SEQ ID NO: 15          moltype = DNA  length = 1164
FEATURE                Location/Qualifiers
source                 1..1164
                       mol_type = other DNA
                       organism = synthetic construct
CDS                    1..1164
                       protein_id = 16
                       transl_table = 1
                       translation = MWFGEFGGQYVPETLVGPLKELEKAYKRFKDDEEFNRQLNYYLKTW
                        AGRPTPLYYAKRLTEKIGGAKVYLKREDLVHGGAHKTNNAIGQALLAKLMGKTRLIAGT
                        GAGQHGVATAMAGALLGMKVDIYMGAEDVERQKLNVFRMKLLGANVIPVNSGSRTLKDA
                        IDEALRDWVATFEYTHYLIGSVVGPHPYPTIVRDFQSVIGREAKAQIPEAEGQLPDVIV
                        ACVGGGSNAMGIFYPFVNDKKVKLVGVEAGGKGLESGKHSASLNAGQVGVSHGMLSYFL
                        QDEEGQIKPSHSIAPGLDYPGVGPEHAYLKKIQRAEYVAVTDEEALKAFHELSRTEGII
                        PALESAHAVAYAMKLAKEMSRDEIIIVNLSGRGDKDLDIVLKASGNV
misc_feature           1..1164
                       note = Pf5G8 E104G
SEQUENCE: 15
atgtggttcg gtgaatttgg tggtcagtac gtgccagaaa cgctggttgg acccctgaaa  60
gagctggaaa aagcttacaa acgtttcaaa gatgacgaag aattcaatcg tcagctgaat  120
tactacctga aaacctgggc aggtcgtcca accccactgt actacgcaaa acgcctgact  180
gaaaaaatcg gtggtgctaa agtctacctg aaacgtgaag acctggttca cggtggtgca  240
cacaagacca acaacgccat cggtcaggca ctgctggcaa agctcatggg taaaactcgt  300
ctgatcgctg ggaccggtgc tggtcagcac ggcgtagcga ctgcaatggc tggtgcactg  360
ctgggcatga aagtggacat ttacatgggt gctgaggacg tagaacgtca gaaattgaac  420
gtattccgta tgaagctgct gggtgcaaac gtaattccag ttaactccgg ttctcgcacc  480
```

-continued

```
ctgaaagacg caatcgacga ggctctgcgt gattgggtgg ctacttttga atacacccac  540
tacctaatcg gttccgtggt cggtccacat ccgtatccga ccatcgttcg tgattttcag  600
tctgttatcg gtcgtgaggc taaagcgcag atcccggagg ctgaaggtca gctgccagat  660
gtaatcgttg cttgtgttgg tggtggctct aacgcgatgg gtatctttta cccgttcgtg  720
aacgacaaaa aagttaagct ggttggcgtt gaggctggtg gtaaaggcct ggaatctggt  780
aagcattccg ctagcctgaa cgcaggtcag gttggtgtgt cccatggcat gctgtcctac  840
tttctgcagg acgaagaagg tcagatcaaa ccaagccact ccatcgcacc aggtctggat  900
tatccaggtg ttggtccaga acacgcttac ctgaaaaaaa ttcagcgtgc tgaatacgtg  960
gctgtaaccg atgaagaagc actgaaagcg ttccatgaac tgagccgtac cgaaggtatc  1020
atcccagctc tggaatctgc gcatgctgtg gcttacgcta tgaaactggc taaggaaatg  1080
tctcgtgatg agatcatcat cgtaaacctg tctggtcgtg gtgacaaaga cctggatatt  1140
gtcctgaaag cgtctggcaa cgtg                                          1164

SEQ ID NO: 16          moltype = AA  length = 388
FEATURE                Location/Qualifiers
source                 1..388
                       mol_type = protein
                       organism = synthetic construct
SEQUENCE: 16
MWFGEFGGQY VPETLVGPLK ELEKAYKRFK DDEEFNRQLN YYLKTWAGRP TPLYYAKRLT  60
EKIGGAKVYL KREDLVHGGA HKTNNAIGQA LLAKLMGKTR LIAGTGAGQH GVATAMAGAL  120
LGMKVDIYMG AEDVERQKLN VFRMKLLGAN VIPVNSGSRT LKDAIDEALR DWVATFEYTH  180
YLIGSVVGPH PYPTIVRDFQ SVIGREAKAQ IPEAEGQLPD VIVACVGGGS NAMGIFYPFV  240
NDKKVKLVGV EAGGKGLESG KHSASLNAGQ VGVSHGMLSY FLQDEEGQIK PSHSIAPGLD  300
YPGVGPEHAY LKKIQRAEYV AVTDEEALKA FHELSRTEGI IPALESAHAV AYAMKLAKEM  360
SRDEIIIVNL SGRGDKDLDI VLKASGNV                                    388

SEQ ID NO: 17          moltype = DNA  length = 1164
FEATURE                Location/Qualifiers
source                 1..1164
                       mol_type = other DNA
                       organism = synthetic construct
CDS                    1..1164
                       protein_id = 18
                       transl_table = 1
                       translation = MWFGEFGGQYVPETLVGPLKELEKAYKRFKDDEEFNRQLNYYLKTW
                        AGRPTPLYYAKRLTEKIGGAKVYLKREDLVHGGAHKTNNAIGQALLAKLMGKTRLIAGT
                        GAGQHGVATAMAGALLGMKVDIYMGAEDVERQKLNVFRMKLLGANVIPVNSGSRTLKDA
                        IDEALRDWVATFEYTHYLFGSAVGPHPYPTIVRDFQSVIGREAKAQIPEAEGQLPDVIV
                        ACVGGGSNAMGIFYPFVNDKKVKLVGVEAGGKGLESGKHSASLNAGQVGVSHGMLSYFL
                        QDEEGQIKPSHSIAPGLDYPGVGPEHAYLKKIQRAEYVAVTDEEALKAFHELSRTEGII
                        PALESAHAVAYAMKLAKEMSRDEIIIVNLSGRGDKDLDIVLKASGNV
misc_feature           1..1164
                       note = Pf2A6
SEQUENCE: 17
atgtggttcg gtgaatttgg tggtcagtac gtgccagaaa cgctggttgg acccctgaaa  60
gagctggaaa aagcttacaa acgtttcaaa gatgacgaag aattcaatcg tcagctgaat  120
tactacctga aaacctgggc aggtcgtcca accccactgt actacgcaaa acgcctgact  180
gaaaaaatcg gtggtgctaa agtctacctg aaacgtgaag acctggttca cggtggtgca  240
cacaagacca acaacgccat cggtcaggca ctgctggcaa agctcatggg taaaactcgt  300
ctgatcgctg ggaccggtgc tggtcagcac ggcgtagcga ctgcaatggc tggtgcactg  360
ctgggcatga aagtggacat ttacatgggt gctgaggacg tagaacgtca gaaattgaac  420
gtattccgta tgaagctgct gggtgcaaac gtaattccag ttaactccgg ttctcgcacc  480
ctgaaagacg caatcgacga ggctctgcgt gattgggtgg ctacttttga atacacccac  540
tacctattcg gttccgcggt cggtccacat ccgtatccga ccatcgttcg tgattttcag  600
tctgttatcg gtcgtgaggc taaagcgcag atcccggagg ctgaaggtca gctgccagat  660
gtaatcgttg cttgtgttgg tggtggctct aacgcgatgg gtatctttta cccgttcgtg  720
aacgacaaaa aagttaagct ggttggcgtt gaggctggtg gtaaaggcct ggaatctggt  780
aagcattccg ctagcctgaa cgcaggtcag gttggtgtgt cccatggcat gctgtcctac  840
tttctgcagg acgaagaagg tcagatcaaa ccaagccact ccatcgcacc aggtctggat  900
tatccaggtg ttggtccaga acacgcttac ctgaaaaaaa ttcagcgtgc tgaatacgtg  960
gctgtaaccg atgaagaagc actgaaagcg ttccatgaac tgagccgtac cgaaggtatc  1020
atcccagctc tggaatctgc gcatgctgtg gcttacgcta tgaaactggc taaggaaatg  1080
tctcgtgatg agatcatcat cgtaaacctg tctggtcgtg gtgacaaaga cctggatatt  1140
gtcctgaaag cgtctggcaa cgtg                                          1164

SEQ ID NO: 18          moltype = AA  length = 388
FEATURE                Location/Qualifiers
source                 1..388
                       mol_type = protein
                       organism = synthetic construct
SEQUENCE: 18
MWFGEFGGQY VPETLVGPLK ELEKAYKRFK DDEEFNRQLN YYLKTWAGRP TPLYYAKRLT  60
EKIGGAKVYL KREDLVHGGA HKTNNAIGQA LLAKLMGKTR LIAGTGAGQH GVATAMAGAL  120
LGMKVDIYMG AEDVERQKLN VFRMKLLGAN VIPVNSGSRT LKDAIDEALR DWVATFEYTH  180
YLFGSAVGPH PYPTIVRDFQ SVIGREAKAQ IPEAEGQLPD VIVACVGGGS NAMGIFYPFV  240
NDKKVKLVGV EAGGKGLESG KHSASLNAGQ VGVSHGMLSY FLQDEEGQIK PSHSIAPGLD  300
YPGVGPEHAY LKKIQRAEYV AVTDEEALKA FHELSRTEGI IPALESAHAV AYAMKLAKEM  360
SRDEIIIVNL SGRGDKDLDI VLKASGNV                                    388
```

```
SEQ ID NO: 19          moltype = DNA  length = 1164
FEATURE                Location/Qualifiers
source                 1..1164
                       mol_type = other DNA
                       organism = synthetic construct
CDS                    1..1164
                       protein_id = 20
                       transl_table = 1
                       translation = MWFGEFGGQYVPETLVGPLKELEKAYKRFKDDEEFNRQLNYYLKTW
                        AGRPTPLYYAKRLTEKIGGAKVYLKREDLVHGGAHKTNNAIGQALLAKLMGKTRLIAET
                        GAGQHGVATAMAGALLGMKVDIYMGAEDVERQKLNVFRMKLLGANVIPVNSGSRTLKDA
                        FDEALRDWVATFEYTHYLIGSVVGPHPYPTIVRDFQSVIGREAKAQILEAEGQLPDVIV
                        ACVGGGSNAMGIFYPFVNDKKVKLVGVEAGGKGLESGKHSASLNAGQVGVSHGMLSYFL
                        QDEEGQIKPSHSIAPGLDHPGVGPEHAYLKKIQRAEYVAVTDEEALKAFHELSRTEGII
                        PALESAHAVAYAMKLAKEMSRDEIIIVNLSGRGDKDLDIVLKASGNV
misc_feature           1..1164
                       note = Pf0A9
SEQUENCE: 19
atgtggttcg gtgaatttgg tggtcagtac gtgccagaaa cgctggttgg acccctgaaa  60
gagctggaaa aagcttacaa acgtttcaaa gatgacgaag aattcaatcg tcagctgaat  120
tactacctga aaacctgggc aggtcgtcca accccactgt actacgcaaa acgcctgact  180
gaaaaaatcg gtggtgctaa agtctacctg aaacgtgaag acctggttca cggtggtgca  240
cacaagacca acaacgccat cggtcaggca ctgctggcaa agctcatggg taaaactcgt  300
ctgatcgctg agaccggtgc tggtcagcac ggcgtagcga ctgcaatggc tggtgcactg  360
ctgggcatga aagtggacat ttacatgggt gctgaggacg tagaacgtca gaaactgaac  420
gtattccgta tgaagctgct gggtgcaaac gtaattccag ttaactccgg ttctcgcacc  480
ctgaaagacg catttgacga ggctctgcgt gattgggtgg ctacttttga atacacccac  540
tacctaatcg gttccgtggt cggtccacat ccgtatccga ccatcgttcg tgattttcag  600
tctgttatcg gtcgtgaggc taaagcgcag atcctggagg ctgaaggtca gctgccagat  660
gtaatcgttg cttgtgttgg tggtggctct aacgcgatgg gtatctttta cccgttcgtg  720
aacgacaaaa aagttaagct ggttggcgtt gaggctggtg gtaaaggcct ggaatctggt  780
aagcattccg ctagcctgaa cgcaggtcag gttggtgtgt cccatggcat gctgtcctac  840
tttctgcagg acgaagaagg tcagatcaaa ccaagccact ccatcgcacc aggtctggat  900
catccaggtg ttggtccaga acacgcttac ctgaaaaaaa ttcagcgtgc tgaatacgtg  960
gctgtaaccg atgaagaagc actgaaagcg ttccatgaac tgagccgtac cgaaggtatc  1020
atcccagctc tggaatctgc gcatgctgtg gcttacgcta tgaaactggc taaggaaatg  1080
tctcgtgatg agatcatcat cgtaaacctg tctggtcgtg gtgacaaaga cctggatatt  1140
gtcctgaaag cgtctggcaa cgtg                                         1164

SEQ ID NO: 20          moltype = AA  length = 388
FEATURE                Location/Qualifiers
source                 1..388
                       mol_type = protein
                       organism = synthetic construct
SEQUENCE: 20
MWFGEFGGQY VPETLVGPLK ELEKAYKRFK DDEEFNRQLN YYLKTWAGRP TPLYYAKRLT  60
EKIGGAKVYL KREDLVHGGA HKTNNAIGQA LLAKLMGKTR LIAETGAGQH GVATAMAGAL  120
LGMKVDIYMG AEDVERQKLN VFRMKLLGAN VIPVNSGSRT LKDAFDEALR DWVATFEYTH  180
YLIGSVVGPH PYPTIVRDFQ SVIGREAKAQ ILEAEGQLPD VIVACVGGGS NAMGIFYPFV  240
NDKKVKLVGV EAGGKGLESG KHSASLNAGQ VGVSHGMLSY FLQDEEGQIK PSHSIAPGLD  300
HPGVGPEHAY LKKIQRAEYV AVTDEEALKA FHELSRTEGI IPALESAHAV AYAMKLAKEM  360
SRDEIIIVNL SGRGDKDLDI VLKASGNV                                     388

SEQ ID NO: 21          moltype = DNA  length = 1164
FEATURE                Location/Qualifiers
source                 1..1164
                       mol_type = other DNA
                       organism = synthetic construct
CDS                    1..1164
                       protein_id = 22
                       transl_table = 1
                       translation = MWFGEFGGQYVPETLVGPLKELEKAYKRFKDDEEFNRQLNYYLKTW
                        AGRPTPLYYAKRLTEKIGGAKVYLKREDLVHGGAHKTNNAIGQALLAKLMGKTRLIAGT
                        GAGQHGVATAMAGALLGMKVDIYMGAEDVERQKLNVFRMKLLGANVIPVNSGSRTLKDA
                        FDEALRDWVATFEYTHYLIGSVVGPHPYPTIVRDFQSVIGREAKAQILEAEGQLPDVIV
                        ACVGGGSNAMGIFYPFVNDKKVKLVGVEAGGKGLESGKHSASLNAGQVGVSHGMLSYFL
                        QDEEGQIKPSHSIAPGLDHPGVGPEHAYLKKIQRAEYVAVTDEEALKAFHELSRTEGII
                        PALESAHAVAYAMKLAKEMSRDEIIIVNLSGRGDKDLDIVLKASGNV
misc_feature           1..1164
                       note = Pf0A9 E104G
SEQUENCE: 21
atgtggttcg gtgaatttgg tggtcagtac gtgccagaaa cgctggttgg acccctgaaa  60
gagctggaaa aagcttacaa acgtttcaaa gatgacgaag aattcaatcg tcagctgaat  120
tactacctga aaacctgggc aggtcgtcca accccactgt actacgcaaa acgcctgact  180
gaaaaaatcg gtggtgctaa agtctacctg aaacgtgaag acctggttca cggtggtgca  240
cacaagacca acaacgccat cggtcaggca ctgctggcaa agctcatggg taaaactcgt  300
ctgatcgctg ggaccggtgc tggtcagcac ggcgtagcga ctgcaatggc tggtgcactg  360
ctgggcatga aagtggacat ttacatgggt gctgaggacg tagaacgtca gaaactgaac  420
```

-continued

```
gtattccgta tgaagctgct gggtgcaaac gtaattccag ttaactccgg ttctcgcacc  480
ctgaaagacg catttgacga ggctctgcgt gattgggtgg ctacttttga atacacccac  540
tacctaatcg gttccgtggt cggtcccacat ccgtatccga ccatcgttcg tgattttcag  600
tctgttatcg gtcgtgaggc taaagcgcag atcctggagg ctgaaggtca gctgccagat  660
gtaatcgttg cttgtgttgg tggtggctct aacgcgatgg gtatctttta cccgttcgtg  720
aacgacaaaa aagttaagct ggttggcgtt gaggctggtg gtaaaggcct ggaatctggt  780
aagcattccg ctagcctgaa cgcaggtcag gttggtgtgt cccatggcat gctgtcctac  840
tttctgcagg acgaagaggg tcagatcaaa ccaagccact ccatcgcacc aggtctggat  900
catccaggtg ttggtccaga acacgcttac ctgaaaaaaa ttcagcgtgc tgaatacgtg  960
gctgtaaccg atgaagaagc actgaaagcg ttccatgaac tgagccgtac cgaaggtatc  1020
atcccagctc tggaatctgc gcatgctgtg gcttacgcta tgaaactggc taaggaaatg  1080
tctcgtgatg agatcatcat cgtaaacctg tctggtcgtg gtgacaaaga cctggatatt  1140
gtcctgaaag cgtctggcaa cgtg                                        1164

SEQ ID NO: 22          moltype = AA  length = 388
FEATURE                Location/Qualifiers
source                 1..388
                       mol_type = protein
                       organism = synthetic construct
SEQUENCE: 22
MWFGEFGGQY VPETLVGPLK ELEKAYKRFK DDEEFNRQLN YYLKTWAGRP TPLYYAKRLT  60
EKIGGAKVYL KREDLVHGGA HKTNNAIGQA LLAKLMGKTR LIAGTGAGQH GVATAMAGAL  120
LGMKVDIYMG AEDVERQKLN VFRMKLLGAN VIPVNSGSRT LKDAFDEALR DWVATFEYTH  180
YLIGSVVGPH PYPTIVRDFQ SVIGREAKAQ ILEAEGQLPD VIVACVGGGS NAMGIFYPFV  240
NDKKVKLVGV EAGGKGLESG KHSASLNAGQ VGVSHGMLSY FLQDEEGQIK PSHSIAPGLD  300
HPGVGPEHAY LKKIQRAEYV AVTDEEALKA FHELSRTEGI IPALESAHAV AYAMKLAKEM  360
SRDEIIIVNL SGRGDKDLDI VLKASGNV                                    388

SEQ ID NO: 23          moltype = DNA  length = 1167
FEATURE                Location/Qualifiers
source                 1..1167
                       mol_type = other DNA
                       organism = synthetic construct
CDS                    1..1167
                       protein_id = 24
                       transl_table = 1
                       translation = MKGYFGPYGGQYVPEILMGALEELEAAYEEIMKDESFWKEFNDLLR
                        DYAGRPTPLYFARRLSEKYGARVYLKREDLLHTGAHKINNAIGQVLLAKLMGKTRIIAE
                        TGAGQHGVATATAAALFGMECVIYMGEEDTIRQKLNVERMKLLGAKVVPVKSGSRTLKD
                        AIDEALRDWITNLQTTYYVIGSVVGPHPYPIIVRNFQKVIGEETKKQIPEKEGRLPDYI
                        VACVGGGSNAAGIFYPFIDSGVKLIGVEAGGEGLETGKHAASLLKGKIGYLHGSKTFVL
                        QDDWGQVQVSHSVSAGLDYSGVGPEHAYWRETGKVLYDAVTDEEALDAFIELSRLEGII
                        PALESSHALAYLKKINIKGKVVVVNLSGRGDKDLESVLNHPYVRERIR
misc_feature           1..1167
                       note = Tm2F3
SEQUENCE: 23
atgaaaggct acttcggtcc gtacggtggc cagtacgtgc cggaaatcct gatgggagct  60
ctggaagaac tggaagctgc gtacgaagaa atcatgaaag atgagtcttt ctggaaagaa  120
ttcaatgacc tgctgcgcga ttatgcgggt cgtccgactc cgctgtactt cgcacgtcgt  180
ctgtccgaaa aatacggtgc tcgcgtatat ctgaaacgtg aagacctgct gcatactggt  240
gcgcataaaa tcaataacgc tatcggccag gttctgctgg caaaactaat gggcaaaacc  300
cgtatcattg ctgaaacggg tgctggtcag cacggcgtag caactgctac cgcagcagcg  360
ctgttcggta tggaatgtgt aatctatatg ggcgaagaag acacgatccg ccagaaacta  420
aacgttgaac gtatgaaact gctgggtgct aaagttgtac cggtaaaatc cggtagccgt  480
accctgaaag acgcaattga cgaagctctg cgtgactgga ttaccaacct gcagaccacc  540
tattacgtga tcggctctgt ggttggtccg catccatatc cgattatcgt acgtaacttc  600
caaaaggtta tcggcgaaga gaccaaaaaa cagattccag aaaaagaagg ccgtctgccg  660
gactacatcg ttgcgtgcgt gggtggtggt tctaacgctg ccggtatctt ctatccgttt  720
atcgattctg gtgtgaagct gatcggcgta gaagccggtg gcgaaggtct ggaaaccggt  780
aaacatgcgg cttctctgct gaaaggtaaa atcggctacc tgcacggttc taagacgttc  840
gttctgcagg atgactgggg tcaagttcag gtgagccact ccgtctccgc tggcctggac  900
tactccggtg tcggtccgga acacgcctat tggcgtgaga ccggtaaagt gctgtacgat  960
gctgtgaccg atgaagaagc tctggacgca ttcatcgaac tgtctcgcct ggaaggcatc  1020
atcccagccc tggagtcttc tcacgcactg gcttatctga agaagatcaa catcaagggt  1080
aaagttgtgg tggttaatct gtctggtcgt ggtgacaagg atctggaatc tgtactgaac  1140
cacccgtatg ttcgcgaacg catccgc                                     1167

SEQ ID NO: 24          moltype = AA  length = 389
FEATURE                Location/Qualifiers
source                 1..389
                       mol_type = protein
                       organism = synthetic construct
SEQUENCE: 24
MKGYFGPYGG QYVPEILMGA LEELEAAYEE IMKDESFWKE FNDLLRDYAG RPTPLYFARR  60
LSEKYGARVY LKREDLLHTG AHKINNAIGQ VLLAKLMGKT RIIAETGAGQ HGVATATAAA  120
LFGMECVIYM GEEDTIRQKL NVERMKLLGA KVVPVKSGSR TLKDAIDEAL RDWITNLQTT  180
YYVIGSVVGP HPYPIIVRNF QKVIGEETKK QIPEKEGRLP DYIVACVGGG SNAAGIFYPF  240
IDSGVKLIGV EAGGEGLETG KHAASLLKGK IGYLHGSKTF VLQDDWGQVQ VSHSVSAGLD  300
YSGVGPEHAY WRETGKVLYD AVTDEEALDA FIELSRLEGI IPALESSHAL AYLKKINIKG  360
```

-continued

```
KVVVVNLSGR GDKDLESVLN HPYVRERIR                          389

SEQ ID NO: 25           moltype = DNA  length = 1167
FEATURE                 Location/Qualifiers
source                  1..1167
                        mol_type = other DNA
                        organism = synthetic construct
CDS                     1..1167
                        protein_id = 26
                        transl_table = 1
                        translation = MKGYFGPYGGQYVPEILMGALEELEAAYEEIMKDESFWKEFNDLLR
                         DYAGRPTPLYFARRLSEKYGARVYLKREDLLHTGAHKINNAIGQVLLAKLMGKTRIIAE
                         TGAGQHGVATATAAALFGMECVIYMGEEDTIRQKLNVERMKLLGAKVVPVKSGSRTLKD
                         AIDEALRDWITNLQTTYYVFGSVVGPHPYPIIVRNFQKVIGEETKKQIPEKEGRLPDYI
                         VACVGGGSNAAGIFYPFIDSGVKLIGVEAGGEGLETGKHAASLLKGKIGYLHGSKTFVL
                         QDDWGQVQVSHSVSAGLDYSGVGPEHAYWRETGKVLYDAVTDEEALDAFIELSRLEGII
                         PALESSHALAYLKKINIKGKVVVVNLSGRGDKDLESVLNHPYVRERIR
misc_feature            1..1167
                        note = Tm2F3 I184F
SEQUENCE: 25
atgaaaggct acttcggtcc gtacggtggc cagtacgtgc cggaaatcct gatgggagct  60
ctggaagaac tggaagctgc gtacgaagaa atcatgaaag atgagtcttt ctggaaagaa  120
ttcaatgacc tgctgcgcga ttatgcgggt cgtccgactc cgctgtactt cgcacgtcgt  180
ctgtccgaaa aatacggtgc tcgcgtatat ctgaaacgtg aagacctgct gcatactggt  240
gcgcataaaa tcaataacgc tatcggccag gttctgctgg caaaactaat gggcaaaacc  300
cgtatcattg ctgaaacggg tgctggtcag cacggcgtag caactgctac cgcagcagcg  360
ctgttcggta tggaatgtgt aatctatatg ggcgaagaag acacgatccg ccagaaacta  420
aacgttgaac gtatgaaact gctgggtgct aaagttgtac cggtaaaatc cggtagccgt  480
accctgaaag acgcaattga cgaagctctg cgtgactgga ttaccaacct gcagaccacc  540
tattacgtgt tcggctctgt ggttggtccg catccatatc cgattatcgt acgtaacttc  600
caaaaggtta tcggcgaaga gaccaaaaaa cagattccag aaaaagaagg ccgtctgccg  660
gactacatcg ttgcgtgcgt gggtggtggt tctaacgctg ccggtatctt ctatccgttt  720
atcgattctg gtgtgaagct gatcggcgta gaagccggtg gcgaaggtct ggaaaccggt  780
aaacatgcgg cttctctgct gaaaggtaaa atcggctacc tgcacggttc taagacgttc  840
gttctgcagg atgactgggg tcaagttcag gtgagccact ccgtctccgc tggcctggac  900
tactccggtg tcggtccgga acacgcctat tggcgtgaga ccggtaaagt gctgtacgat  960
gctgtgaccg atgaagaagc tctggacgca ttcatcgaac tgtctcgcct ggaaggcatc  1020
atcccagccc tggagtcttc tcacgcactg gcttatctga agaagatcaa catcaagggt  1080
aaagttgtgg tggttaatct gtctggtcgt ggtgacaagg atctggaatc tgtactgaac  1140
cacccgtatg ttcgcgaacg catccgc                                    1167

SEQ ID NO: 26           moltype = AA  length = 389
FEATURE                 Location/Qualifiers
source                  1..389
                        mol_type = protein
                        organism = synthetic construct
SEQUENCE: 26
MKGYFGPYGG QYVPEILMGA LEELEAAYEE IMKDESFWKE FNDLLRDYAG RPTPLYFARR  60
LSEKYGARVY LKREDLLHTG AHKINNAIGQ VLLAKLMGKT RIIAETGAGQ HGVATATAAA  120
LFGMECVIYM GEEDTIRQKL NVERMKLLGA KVVPVKSGSR TLKDAIDEAL RDWITNLQTT  180
YYVFGSVVGP HPYPIIVRNF QKVIGEETKK QIPEKEGRLP DYIVACVGGG SNAAGIFYPF  240
IDSGVKLIGV EAGGEGLETG KHAASLLKGK IGYLHGSKTF VLQDDWGQVQ VSHSVSAGLD  300
YSGVGPEHAY WRETGKVLYD AVTDEEALDA FIELSRLEGI IPALESSHAL AYLKKINIKG  360
KVVVVNLSGR GDKDLESVLN HPYVRERIR                                  389
```

ENGINEERED SYNTHASE FOR PRODUCTION OF TRYPTOPHAN DERIVATIVES AND INTRANSIGENT SUBSTRATES

CROSS REFERENCE TO RELATED APPLICATIONS

This application is a continuation of U.S. Non-Provisional application Ser. No. 17/724,390, filed Apr. 19, 2022, which is a division of U.S. Non-Provisional application Ser. No. 15/685,839, filed Aug. 24, 2017, now U.S. Pat. No. 11,332,729, issued May 17, 2022, which claims priority under 35 U.S.C. 119 to U.S. Provisional Application Ser. No. 62/379,039, filed Aug. 24, 2016, U.S. Provisional Application Ser. No. 62/462,193, filed Feb. 22, 2017 and U.S. Provisional Application No. 62/507,383, filed May 17, 2017, the disclosures of which are incorporated herein by reference.

STATEMENT REGARDING FEDERALLY SPONSORED RESEARCH

This invention was made with government support under Grant No. GM117635 awarded by the National Institutes of Health. The government has certain rights in the invention.

INCORPORATION BY REFERENCE OF SEQUENCE LISTING

The instant application contains a Sequence Listing which has been submitted via Patent Center and is hereby incorporated by reference in its entirety for all purposes. Said .xml copy, created on Jan. 29, 2024 is named 086544-1418094-021823US, and is 61,317 bytes in size.

TECHNICAL FIELD

This invention relates to modified tryptophan synthase and more particularly to modified beta-subunits of tryptophan synthase. The invention further relates to cells expressing such modified subunits and methods of using such modified subunits for the production of tryptophan derivatives and other chemical entities that are challenging to synthesize.

BACKGROUND

Heteromeric enzyme complexes catalyzing a rich array of useful reactions are often allosterically regulated by their protein partners, such that the catalytic subunits are much less active when isolated. Utilizing isolated enzyme subunits, however, is desirable for biosynthetic applications, wherein expressing large complexes increases the metabolic load on the host cell and complicates efforts to engineer activity, substrate specificity, stability, and other properties.

Tryptophan synthase (TrpS; EC 4.2.1.20) is a heterodimeric complex that catalyzes the formation of L-tryptophan (Trp) from L-serine (Ser) and indole glycerol phosphate (IGP) (see, FIG. 1A). The mechanism of this transformation has been extensively studied for TrpS from *Escherichia coli* and *Salmonella typhimurium*, where it has been shown that the enzyme consists of two subunits, TrpA (α-subunit) and TrpB (β-subunit), both of which have low catalytic efficiencies in isolation. The activities of both subunits increase upon complex formation and are further regulated by an intricate and well-studied allosteric mechanism. IGP binding to the α-subunit stimulates pyridoxal phosphate (PLP)-dependent aminoacrylate formation in the β-subunit [E (A-A); FIG. 1B], which in turn promotes retro-aldol cleavage of IGP in the α-subunit, releasing indole. This tightly choreographed mechanism serves to prevent the free diffusion of indole, which is only released from the α-subunit when the complex is in a closed conformation that forms a 25-Å tunnel through which indole diffuses into the β-subunit. Here, indole reacts with E (A-A) in a C—C bond-forming reaction, yielding L-tryptophan as product (FIG. 1B). These allosteric effects are mediated through the rigid-body motion of the communication (COMM) domain and a monovalent cation (MVC) binding site within the β-subunit (FIG. 1A), which undergo complex conformational transitions associated with open, partially closed, and fully closed states during the catalytic cycle.

SUMMARY

The disclosure provides TrpB-derived biocatalysts that exhibit activity with mono- and disubstituted indoles. The substrate scope includes indoles bearing electron-withdrawing groups, such as nitro and cyano, which are fundamentally deactivating in this reaction manifold. The disclosure showcases the potency of the amino-acrylate as an electrophile, as well as the ability of the active site to protect the amino-acrylate from degradation, while promoting reactions with even the most stubborn nucleophiles. These qualities make mutant-TrpB catalysis a versatile and easy-to-use platform for the production of valuable synthetic building blocks.

The disclosure provides a recombinant polypeptide comprising an isolate β-subunit of tryptophan synthase (EC 4.2.1.20), wherein the isolate β-subunit comprises at least one mutation that stabilizes the closed state of the isolate β-subunit wherein the recombinant polypeptide catalyzes the production of tryptophan analogs substituted at the 4-, 5-, 6- and/or 7-position using serine and an indole analog as a substrate. In one embodiment, the isolate β-subunit has a sequence that is at least 57% to 99% identical to SEQ ID NO:2. In another embodiment, the indole analog comprises a structure as set forth in Formula I:

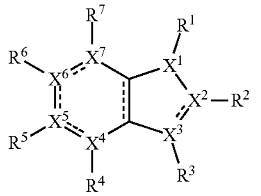

wherein $X_1$-$X_7$ are independently either a carbon, nitrogen, oxygen, or sulfur; $R_1$-$R_3$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen and $R_4$-$R_7$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen, wherein at least one of $R_4$-$R_7$ is an electron withdrawing group. In another embodiment, the indole analog has a structure of Formula II:

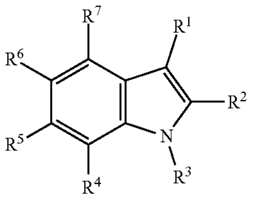

wherein, $R_1$-$R_3$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen and $R_4$-$R_7$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen, wherein at least one of $R_4$-$R_7$ is an electron withdrawing group. In yet another embodiment, the indole analog is selected from the group consisting of:

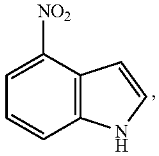, 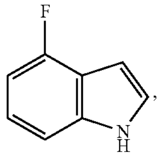, 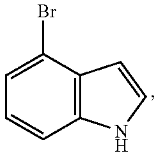,

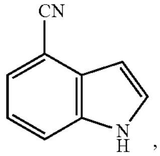, 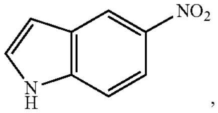,

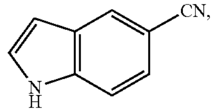, 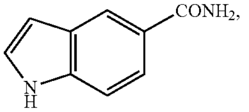,

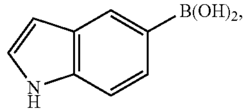, 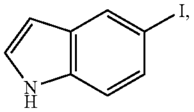,

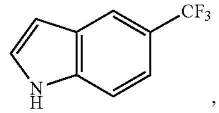, 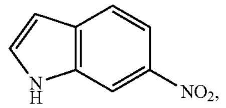,

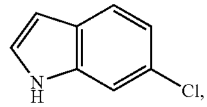, 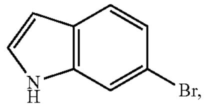,

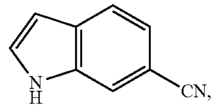, 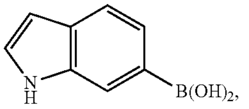,

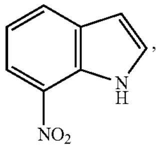, 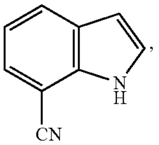, 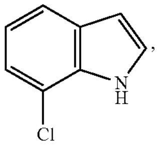,

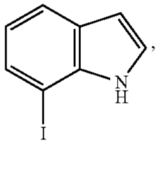, 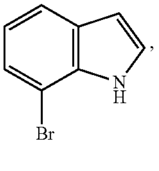, 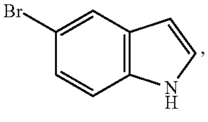,

-continued

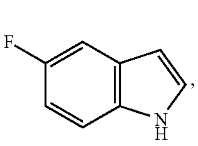, 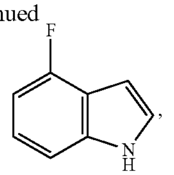,

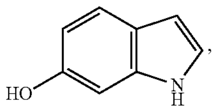, and 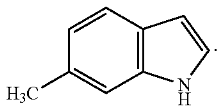.

In yet another embodiment, the recombinant polypeptide comprises a sequence selected from the group consisting of: (a) about 57% or more identity to SEQ ID NO: 2 and has activating mutations at positions 16, 17, 68, 95, 104, 139, 166, 183, 186, 212, 274, 292, 321 and 384; (b) about 57% or more identity to SEQ ID NO: 4 and has activating mutations at positions 29, 30, 80, 107, 116, 151, 178, 195, 198, 224, 285, 303, 332, and 395; (c) about 57% or more identity to SEQ ID NO: 6 and has activating mutations at positions 18, 19, 69, 96, 105, 140, 167, 184, 187, 213, 274, 292, and 381; and (d) about 57% or more identity to SEQ ID NO: 8 and has activating mutations at positions 22, 23, 73, 100, 109, 144, 171, 188, 217, 279, 326, and 390. In a further embodiment, the activating mutations of (a) are selected from the group consisting of I16V, E17G, I68V, F95L, E104G or E104A, M139L, N166D, I183F, V186A, L212P, F274S, T292S, T321A, V384A and any combination thereof relative to SEQ ID NO: 2. In another embodiment, the activating mutation of (b) are selected from the group consisting of I29V, P30V, I80V, F107L, E116G or E116A, M151L, N178D, I195F, V198A, I224P, L285S, T303S, T332A, R395A and any combination thereof relative to SEQ ID NO: 4. In still another embodiment, the activating mutation of (c) are selected from the group consisting of M18V, P19G, I69V, K96L, E105G (or E105A), P140L, N167D, I184F, V187A, L213P, L274S, T292S, H381A and any combination thereof relative to SEQ ID NO: 6. In another embodiment, the activating mutation of (d) are selected from the group consisting of M22V, P23G, L73V, R100L, E109G or E109A, P144L, N171D, L188F, L217P, Y279S, S326A, 1390A and any combination thereof relative to SEQ ID NO: 8. In another embodiment, the polypeptide is at least 80% identical to SEQ ID NO: 14, 16, 18, 20, 22, 24 or 26 and wherein the polypeptide catalyzes the production of tryptophan analogs substituted at the 4-, 5-, 6- and/or 7-position using serine and an indole analog as a substrate.

The disclosure also provides an isolated nucleic acid encoding any of the polypeptide embodiments set forth herein.

The disclosure also provides a vector containing a polynucleotide of the disclosure. In one embodiment, the vector is an expression vector.

The disclosure also provides recombinant host cells that have been transformed or transfected with a nucleic acid or vector of the disclosure.

The disclosure also provides a method for producing tryptophan analog, a non-canonical amino acid and/or an unnatural amino acid comprising contacting an indole analog and L-serine with a polypeptide of the disclosure.

The disclosure provides a method for producing a tryptophan analog substituted at the 4-, 5-, 6- and/or 7-position, the method comprising (a) providing L-serine, an indole analog substituted at the 4-, 5-, 6- and or 7-position and an isolated β-subunit of tryptophan synthase (EC 4.2.1.20)

having at least a mutation corresponding to E104 of SEQ ID NO: 10; and (b) admixing the components of (a) in a reaction for a time and under conditions to produce the tryptophan analog. In one embodiment, the indole analog comprises a structure as set forth in Formula I:

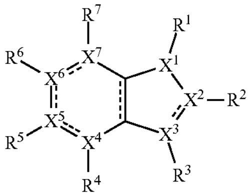

wherein $X_1$-$X_7$ are independently either a carbon, nitrogen, oxygen, or sulfur; $R_1$-$R_3$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen and $R_4$-$R_7$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen, wherein at least one of $R_4$-$R_7$ is an electron withdrawing group. In another embodiment, the indole analog has a structure of Formula II:

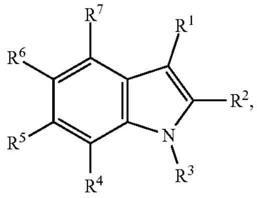

wherein $R_1$-$R_3$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen and $R_4$-$R_7$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen, wherein at least one of $R_4$-$R_7$ is an electron withdrawing group. In yet another embodiment, the indole analog is selected from the group consisting of:

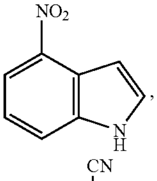 , 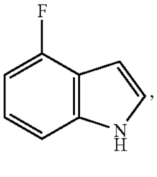 , 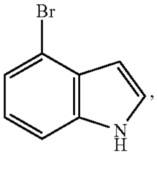 ,

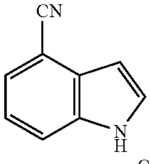 , 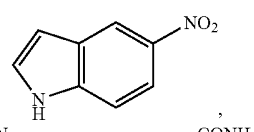 ,

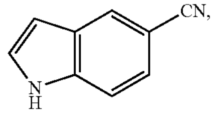 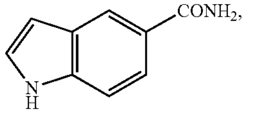

-continued

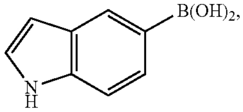 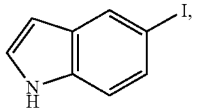

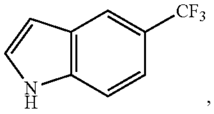 , 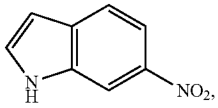

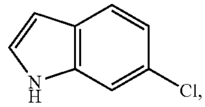 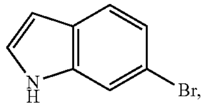

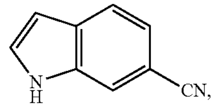 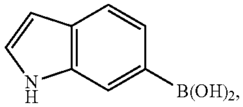

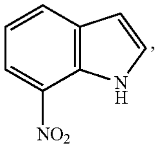 , 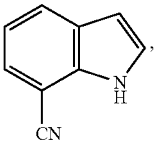 , 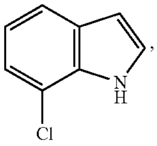 ,

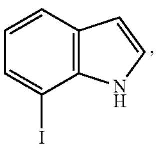 , 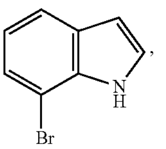 , 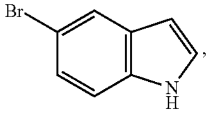 ,

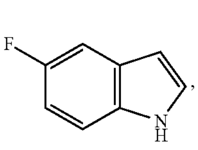 , 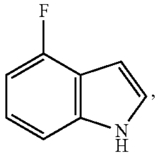 ,

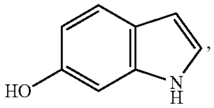 , and 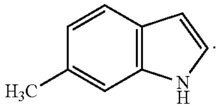 .

In another embodiment, the β-subunit of tryptophan synthase is from *E. coli*, *S. typhimurium*, *P. furiosus*, *A. fulgidus* or *T. maritima*. In another embodiment, the recombinant polypeptide comprises a sequence selected from the group consisting of (a) about 57% or more identity to SEQ ID NO: 2 and has activating mutations at positions 16, 17, 68, 95, 104, 139, 166, 183, 186, 212, 274, 292, 321 and 384; (b) about 57% or more identity to SEQ ID NO: 4 and has activating mutations at positions 29, 30, 80, 107, 116, 151, 178, 195, 198, 224, 285, 303, 332, and 395; (c) about 57% or more identity to SEQ ID NO: 6 and has activating mutations at positions 18, 19, 69, 96, 105, 140, 167, 184, 187, 213, 274, 292, and 381; and (d) about 57% or more identity to SEQ ID NO: 8 and has activating mutations at positions 22, 23, 73, 100, 109, 144, 171, 188, 217, 279, 326, and 390. In a further embodiment, the activating mutations of (a) are selected from the group consisting of I16V, E17G, I68V, F95L, E104G or E104A, M139L, N166D, I183F, V186A, L212P, F274S, T292S, T321A, V384A and any combination thereof relative to SEQ ID NO:2. In another embodiment, the activating mutation of (b) are selected from the group consisting of I29V, P30V, I80V, F107L, E116G or E116A, M151L, N178D, I195F, V198A, I224P, L285S, T303S, T332A, R395A and any combination thereof relative to SEQ ID NO: 4. In yet another embodiment, the activating mutation of (c) are selected from the group consisting of M18V, P19G, I69V, K96L, E105G or E105A, P140L, N167D, I184F, V187A, L213P, L274S, T292S, H381A and any combination thereof relative to SEQ ID NO: 6. In still another embodiment, the activating mutation of (d) are selected from the group consisting of M22V, P23G, L73V, R100L, E109G or E109A, P144L, N171D, L188F, L217P, Y279S, S326A, 1390A and any combination thereof relative to SEQ ID NO: 8. In yet another embodiment, the polypeptide is at least 80% identical to SEQ ID NO: 14, 16, 18, 20, 22, 24 or 26 and wherein the polypeptide catalyzes the production of tryptophan analogs substituted at the 4-, 5-, 6- and/or 7-position using serine and an indole analog as a substrate. In still another embodiment, the method is carried out in a cell free system.

The disclosure also provides a reaction mixture for carrying out the method of the disclosure, wherein the reaction mixtures comprises a buffer, pyridoxal phosphate, an indole analog, L-serine and an isolated β-subunit of tryptophan synthase having at least 80% identity to SEQ ID NO: 10 and having an mutation at E104.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

FIG. 2 shows a multiple sequence alignment of Pf (SEQ ID NO: 2), Af (SEQ ID NO: 4), Im (SEQ ID NO: 6) and Ec (SEQ ID NO: 8) TrpB homologs. The mutated residues identified in the present disclosure are shown above the first line. Symbols under sequences: (*) identify identical residues, (:) report for residues of equal nature, and (.) recognize roughly similar residues.

FIG. 4A-C shows Putative reaction pathways for reaction with 4-nitroindole. (A) Catalytic cycle for formation of 4-nitroTrp. (B) Enzymatic decomposition of Ser. (C) Competitive formation of isotryptophan 1.

Like reference symbols in the various drawings indicate like elements.

DETAILED DESCRIPTION

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a," "an," and "the" include plural referents unless the content clearly dictates otherwise.

Unless defined otherwise, all technical and scientific terms used herein have the same meaning as commonly understood by one of ordinary skill in the art to which the invention pertains. Although any methods and materials similar or equivalent to those described herein can be used in the practice for testing of the invention (s), specific examples of appropriate materials and methods are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Where a range is recited, the disclosure contemplates any value between the range and includes sub-ranges within the range. Moreover, a percentage of "at least X %" includes X % up to any including 100% unless clearly indicated otherwise, and includes any percentage value therebetween.

Any publications discussed above and throughout the text are provided solely for their disclosure prior to the filing date of the present application. Nothing herein is to be construed as an admission that the inventors are not entitled to antedate such disclosure by virtue of prior disclosure.

Figure 1A:
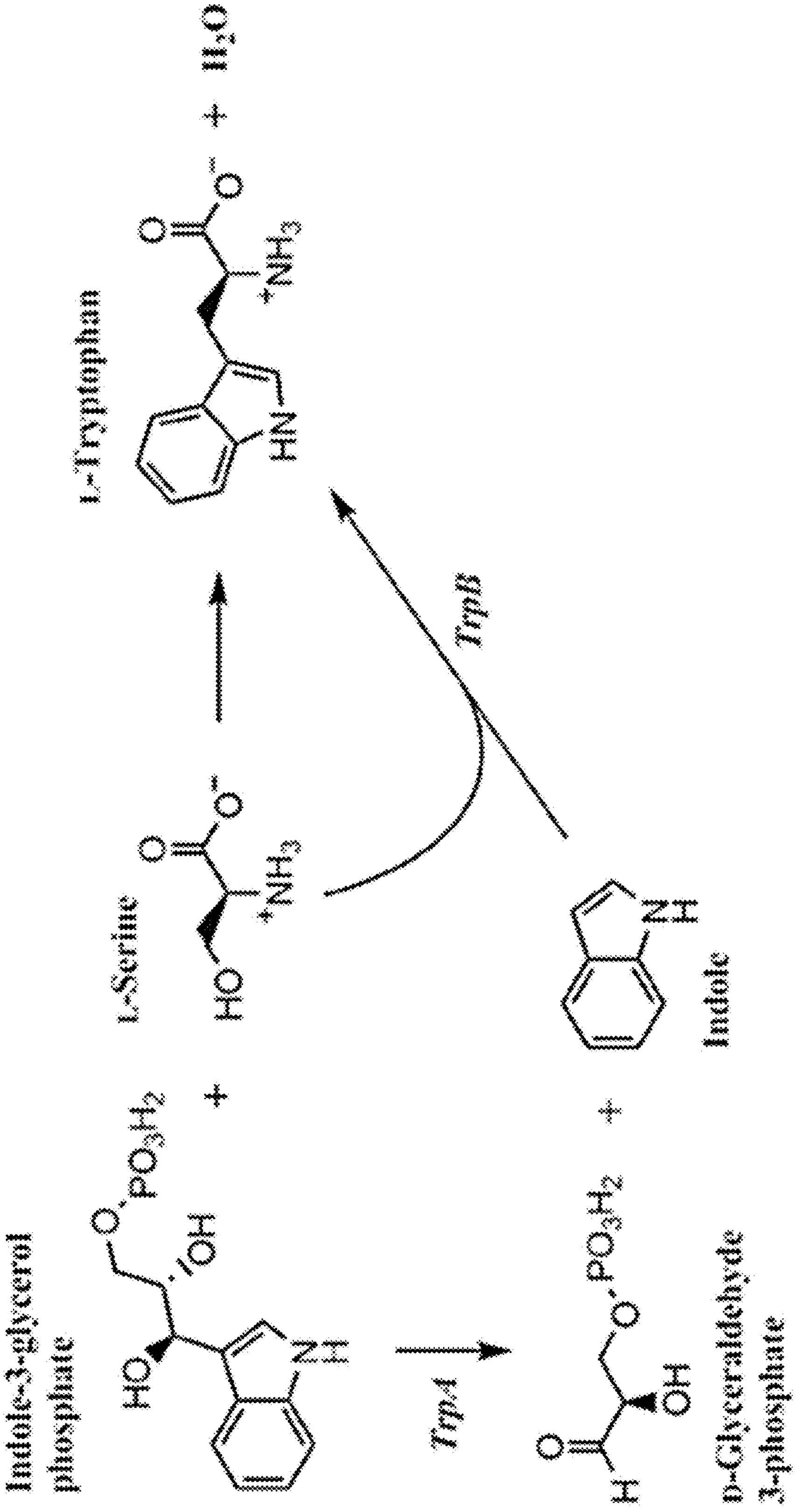
FIG. 1A shows the last two steps in the biosynthesis of L-Trp catalyzed by the multi-enzyme complex tryptophan synthase. IGP is cleaved into G3P and indole by TrpA. The latter serves as nucleophile in the TrpB-catalyzed replacement reaction of the L-Ser hydroxyl to give L-Trp. G3P and water are released as side products of the overall reaction.
Figure 1B:
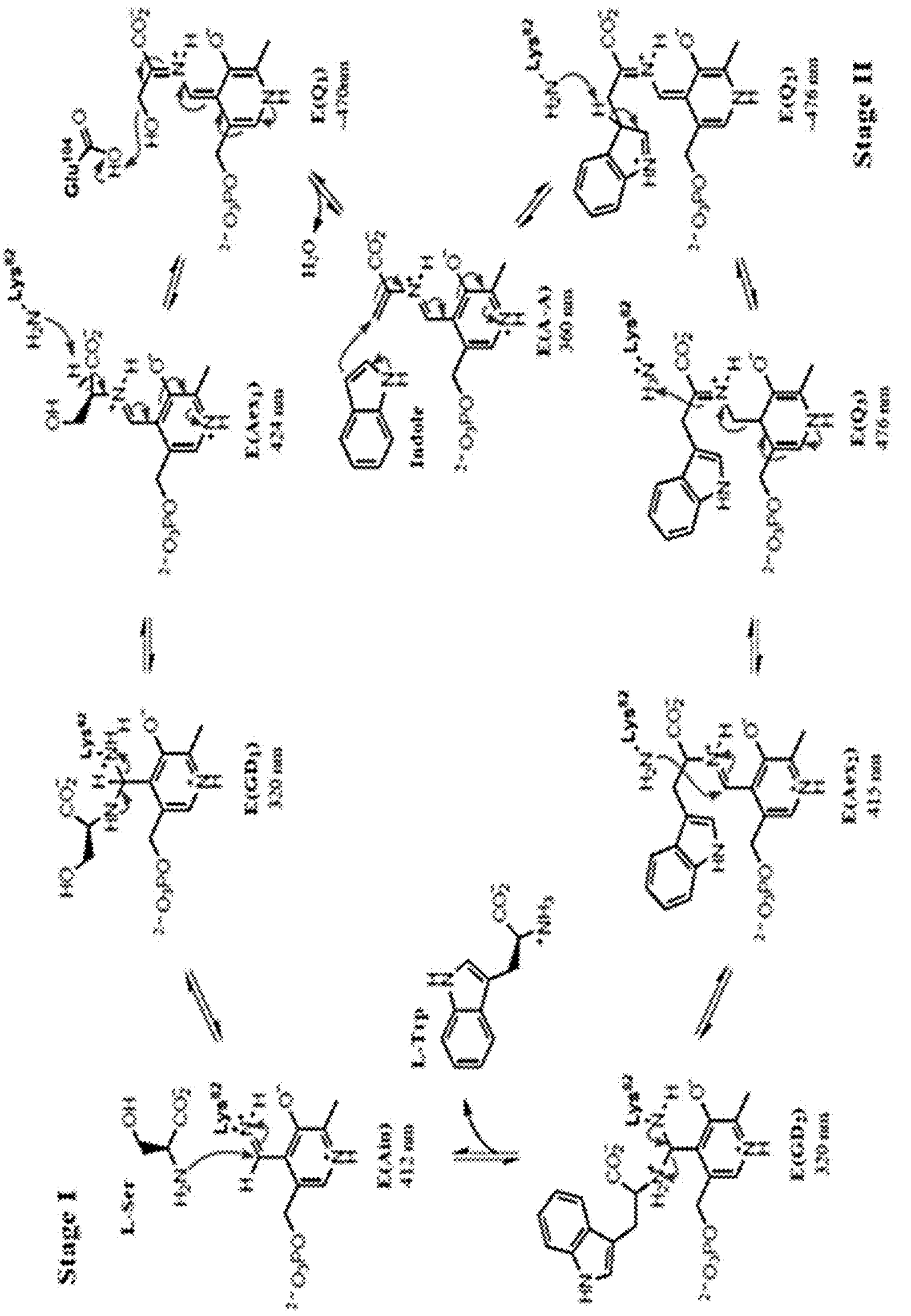
FIG. 1B shows a depiction of the mechanism of the β-replacement reaction in tryptophan synthase divided into α, β-elimination of L-Ser (stage I) and nucleophilic addition of indole (stage II). The wavelengths beneath each intermediate belong to maximum absorbances observed in TrpB from *E. coli* and *S. typhimurium.*
Figure 3A:
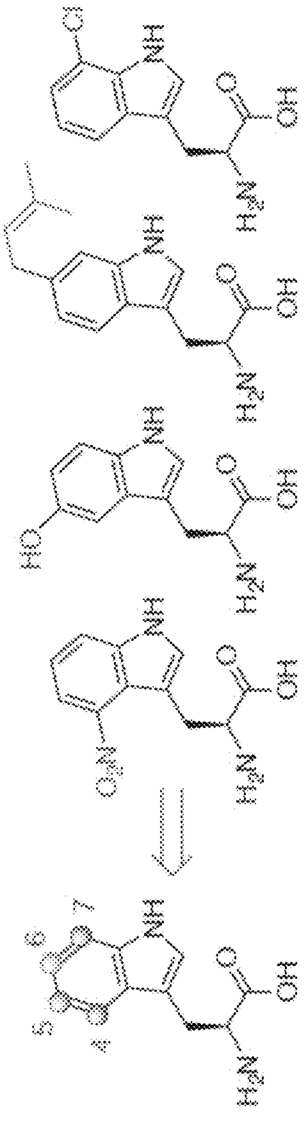
FIG. 3A-C shows the synthesis of Trp analogs. (A) Shows examples of biosynthetic intermediates derived from Trp. (B) Shows previous synthetic methods using enzymes. (C) Shows an alternative biocatalytic route based on TrpB. Ac=acetyl.
Figure 3B:
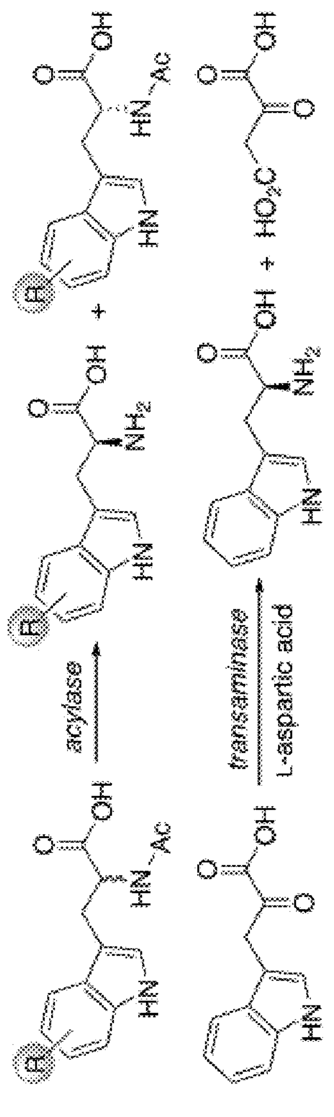
Figure 3C:
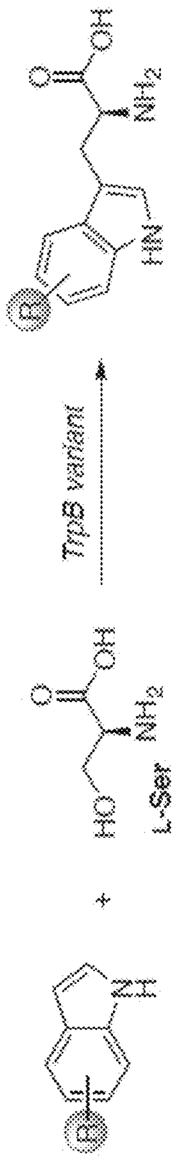

Enzymes such as acylases and transaminases (FIG. 3B) have been applied to synthesis of tryptophan analogs, but in these approaches, the majority of the product must be assembled in advance, with the enzymes mostly serving to set the stereochemistry at the end. Many methods, such as those that use esterases, rely on kinetic resolution, which limits the maximum theoretical yield of product to 50%. A notable exception is the use of tryptophan synthase (TrpS), which can assemble Trp analogs from L-serine (Ser) and the corresponding indole analog with retention of enantiopurity (FIG. 3*c*).

TrpS is a naturally promiscuous enzyme complex catalyzing β-substitution reaction with most haloindoles, methylindoles, and aminoindoles, along with an assortment of nonindole nucleophiles for C—S and C—N bond formation. Such noncanonical amino acids (NCAAs) have diverse applications in chemical biology, serve as intermediates in the synthesis of natural products, and are privileged scaffolds for the development of pharmaceuticals. Despite its natural ability to produce these desirable compounds, TrpS has enjoyed only limited application. Optimized methods are restricted by low substrate concentrations and yields typically below 50%. To produce NCAAs, researchers have used the *S. typhimurium* TrpS complex (StTrpS), which suffers from poor thermostability and low tolerance to organic solvents.

Tryptophan synthase is typically found as a bi-enzyme complex linearly arranged. In *S. typhimurium*, the smaller α-subunit (27 kDa) adopts a TIM β/α barrel. The PLP-dependent β-subunit (43 kDa) is of a fold type II conformation and features a monovalent cation-binding site adjacent to its catalytic center. The active sites of the subunits are interconnected by a substrate tunnel for efficient channeling of the common metabolite, indole. A great degree of allosteric regulation by an intricate network of interactions is necessary to synchronize the catalytic activities in the spatially separated active sites of the tryptophan synthase complex. A variety of analytical tools have been sought out to gain a more detailed mechanical and chemical understanding of the allosteric regulation mechanisms involved in catalysis, including biochemical solution experiments, mutational studies, and X-ray crystallography. The most essential feature allowing for the high enzymatic efficiency of tryptophan synthase is the direct channeling of the common intermediate, indole, through the hydrophobic 25-Å long substrate tunnel interconnecting the active sites of the subunits. As mentioned tryptophan synthase comprises a polymeric polypeptide of two alpha and two beta subunits referred to as TrpA (tryptophan-α) and TrpB (tryptophan-β) that form an α-ββ-α complex. The a and B subunits have molecular masses of 27 and 43 kDa, respectively. The a subunit has a TIM barrel conformation. The β subunit has a fold type II conformation and a binding site adjacent to the active site for monovalent cations. Their assembly into a complex leads to structural changes in both subunits resulting in reciprocal activation. There are two main mechanisms for intersubunit communication. First, the COMM domain of the β-subunit and the α-loop2 of the α-subunit interact. Additionally, there are interactions between the αGly181 and βSer178 residues. The active sites are regulated allosterically and undergo transitions between open, inactive, and closed, active, states.

Amino acids are organic compounds that form the basis for almost all functional molecules in biological systems. Twenty-one amino acids, which span a wide range of chemical and physical properties, form the basis for the proteins found in all living things. However, nature's repertoire of amino acids extends beyond this set of twenty-one to include the so called non-canonical amino acids (ncAAs), which are not found in proteins, but nonetheless act as signaling molecules and serve as starting materials in both biosynthesis and chemical synthesis.

The interest in non-canonical amino acids (NCAA) has been exponentially growing ever since the possibility of their site-specific introduction into enzymes both in vivo and in vitro through nonsense codon suppression. A large and diverse library of unnatural amino acids (UAAs) has been established to address unresolved questions in protein structure and function with unreached precision. The applications are numerous, including incorporation of biophysical probes, such as fluorescent tags and spin labels, production of "caged" proteins with photoreactive side chains, assessing protein stability, and improving natural enzyme activity.

Furthermore, compounds of peptidic structure are often found in nature and employed in drugs by the pharmaceutical industry. However, chemical synthesis of these substances can be challenging. As part of the green-chemistry movement the enzymatic synthesis of non-canonical peptidic compounds has gained in importance. In addition to the mild conditions and nontoxic reagents, enzymatic reactions often occur with high enantiomeric purity and remarkable rate acceleration.

Tryptophan synthase has also been extensively employed for the enzymatic synthesis of a variety of tryptophan analogues, including methylated, halogenated, and aminated L-tryptophans, dihydroisotryptophan, and selenatryptophan. The common basic approach of the aforementioned cases consists of creating batch reactions of indole analogues and L-Ser catalyzed by native tryptophan synthases.

As used herein an "indole analog" refers to any number of known derivatives of indole as set forth in Formula I:

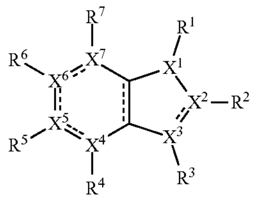

wherein $X_1$-$X_7$ are independently either a carbon, nitrogen, oxygen, or sulfur; $R_1$-$R_7$ are each independently selected from the group consisting of H, —OH, alkyl, aryl, alkoxy, alkenes, alkynes, and substitutions of the foregoing, sulfur-containing group (e.g., thioalkoxy), nitrogen-containing groups (e.g., amide, amino, nitro, azide, and cyano), oxygen-containing group (e.g., ketone, aldehyde, ester, ether, carboxylic acid, and acyl halide), or halogen (e.g., Br, F, iodine). In one embodiment, the indole analog has a structure of Formula II:

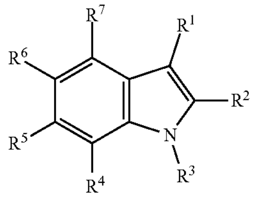

wherein $R_1$-$R_7$ are each independently selected from the group consisting of H, —OH, alkyl, aryl, alkoxy, alkenes, alkynes, and substitutions of the foregoing, sulfur-containing group (e.g., thioalkoxy), nitrogen-containing groups (e.g., amide, amino, nitro, azide, and cyano), oxygen-containing group (e.g., ketone, aldehyde, ester, ether, carboxylic acid, and acyl halide), or halogen (e.g., Br, F, iodine). In one embodiment, the indole analog is selected from the group consisting of:

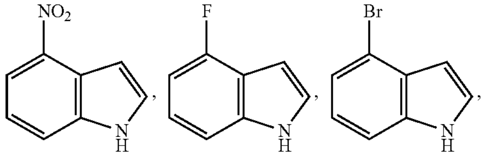
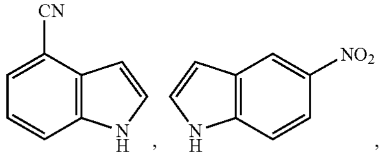
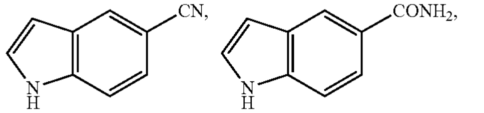
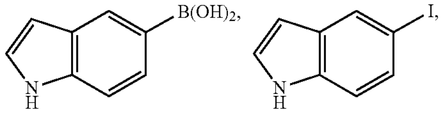
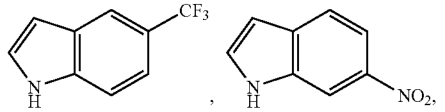
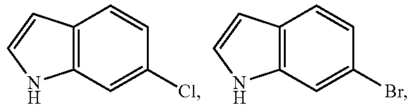
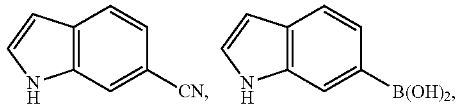
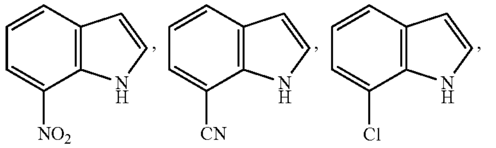
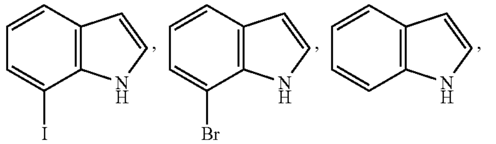
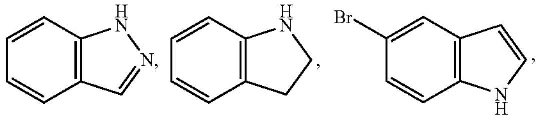
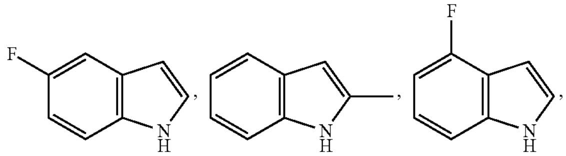
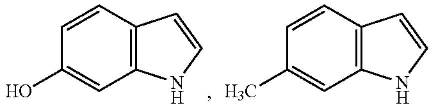

and

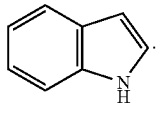

As used herein a "mutant TrpB", "TrpB mutant", "mTrpB" or "engineered TrpB" refers to the β-subunit of tryptophan synthase (TrpS) that has been recombinantly modified to differ from the wild-type sequence. A mutant TrpB typically has a desired substrates specificity, turnover number, product production, stability, etc. that differ from a wild-type enzyme or subunit. A mutant TrpB can be derived from a number of homologs of diverse origin, wherein the mutant TrpB differs from a wild-type of parental polypeptide by one or more (e.g., 2, 3, 4, 5, 6, 7, 8, 9, 10, 15, 20, 25, 30 or more, up to about 50) mutations and wherein the mutant TrpB can generate NCAA. UAA amino acids or other desired chemical entities from an indole analog and a serine or threonine substrate or analog and/or wherein the mutant TrpB functions independent of the TrpA subunit.

A "mutant", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. A mutant or modified protein or enzyme is usually, although not necessarily, expressed from a mutant polynucleotide or gene.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon.

Modified amino acids are amino acids that are chemically modified. Non-limiting examples of a modified amino acid include a glycosylated amino acid, a sulfated amino acid, a prenylated (e.g., farnesylated, geranylgeranylated) amino acid, an acetylated amino acid, an acylated amino acid, a pegylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme.

A "parental polypeptide" refers to a polypeptide used to generate a recombinant or mutant polypeptide. The term "parental polypeptide" describes a polypeptide that occurs in nature, i.e. a "wild-type" cell that has not been genetically modified. The term "parental polypeptide" also describes a polypeptide that serves as the "parent" for further engineering. For example, a wild-type polypeptide can be mutated to have a first mutation or set of mutations that can provide a desired biological activity or be "silent mutations". For example, the wild-type TrpB from *P. furiosus* (SEQ ID NO: 2), *A. fulgidus* (SEQ ID NO: 4), *T. maritima* (SEQ ID NO: 6) or *E. coli* (SEQ ID NO: 8) can serve as a parent wild-type polypeptide for mutagenesis. The polypeptide can be mutated to include a first set of mutations (e.g., mutations at I16, E17, I68, F95, F274, T292, T321 and V384) to give rise to mutant PfTrpB2B9 (SEQ ID NO: 10). This first mutant polypeptide (e.g., PfTrpB2B9) can then act as a parental polypeptide in the generation of second mutation or set of mutations that can provide a desired biological activity or be silent mutations.

The term "polynucleotide," "nucleic acid" or "recombinant nucleic acid" refers to polynucleotides such as deoxyribonucleic acid (DNA), and, where appropriate, ribonucleic acid (RNA).

A "protein" or "polypeptide", which terms are used interchangeably herein, comprises one or more chains of chemical building blocks called amino acids that are linked together by chemical bonds called peptide bonds. A protein or polypeptide can function as an enzyme. An "enzyme" means any substance, composed wholly or largely of protein, that catalyzes or promotes, more or less specifically, one or more chemical or biochemical reactions. As used herein "TrpB" refers to a diverse set of homologs of the β-subunit of tryptophan synthase. A wild-type TrpB can be used as a parental polypeptide for mutation. For example, the TrpB from *Pyroccous furiosus* (PfTrpB) is used as a reference sequence in the disclosure and comprises or consists of the sequence as set forth in SEQ ID NO: 2. Homologs of PfTrpB are known and include, for example, TrpB from *Archaeoglobus fulgidus* (Af), which has 72% sequence identity to PfTrpB, and TrpB from *Escherichia coli* (Ec), which has 57% sequence identity to PfTrpB. Accordingly, wild-type TrpB sequences having at least 57% sequence identity to SEQ ID NO:2 can be used as a parental polypeptide for mutations to form mutant TrpB. The disclosure demonstrates that a diverse set of TrpB homologs based on a phylogenetic analysis of TrpB, including *Archaeoglobus fulgidus* (AfTrpB, 72% sequence identity), *Thermotoga maritima* (TmTrpB, 64%), and *Escherichia coli* (EcTrpB, 57%) are useful in obtaining desirable mutant TrpBs. A multiple-sequence alignment with PfTrpB is shown in FIG. 2.

The engineered/mutant tryptophan beta-subunits (TrpBs) described throughout the disclosure were acquired by accumulating point mutations in directed evolution experiments from a parental polypeptide. An alternative method for making libraries for directed evolution to obtain modified TrpBs with new or altered properties is recombination, or chimeragenesis, in which portions of homologous TrpBs are swapped to form functional chimeras. Therefore, the amino acid mutations made in this way are less disruptive, on average, than random mutations. A structure-based algorithm, such as SCHEMA, identifies fragments of proteins that can be recombined to minimize disruptive interactions that would prevent the protein from folding into its active form.

Provided herein are variants of TrpB that catalyze the synthesis of NCAAs and UAAs. The reaction uses indole analogs and L-serine or L-threonine or analogs thereof.

The term "total turnover number" (TTN) is the total number of substrate molecules converted to product (or turned over) by an enzyme over its lifetime or during a specified time period. TTN is an important figure of merit for a catalyst because it allows for the calculation of the total amount of product that can be made from a given quantity of catalyst.

The modified TrpB subunits used as catalyst can, in some instances, function at ambient temperature or higher (e.g., from 20° C. to 95° C., typically about 75° C.) and ambient pressure.

The mutant TrpBs of the disclosure have enormous potential for applications in drug discovery, chemical synthesis, pharmaceutical preparations, and biotechnology. However, tailoring TrpBs to accept nonnatural substrates, as required by many applications, is difficult in this catalytic system, which involves multiple subunits having allosteric interactions. Compared to their natural counterparts, engineered/mutant TrpBs of the disclosure have improved catalytic and coupling efficiencies.

The phrase "TrpB activity" refers to the biological activity of TrpB or mutants thereof. For example, TrpB activity includes the ability of the TrpB polypeptide to produce NCAAs or UAAs from an indole or derivative thereof and L-serine or L-threonine. A mTrpB activity includes the ability to produce, in one embodiment, a 4-, 5-, 6- and/or 7-position substituted tryptophan analog from a 4-, 5-, 6- and/or 7-position substituted indole analog and L-serine (Ser).

The term "substrate" or "suitable substrate" means any substance or compound that is converted or meant to be converted into another compound by the action of an enzyme catalyst. The term includes indole and indole derivatives as well as serine or threonine and derivatives thereof.

As will be described in more detail below, the disclosure is based, at least in part, on the generation and expression of novel enzymes that catalyze the conversion of indole or indole derivatives and serine or threonine to NCAAs, UAAs and other chemical entities. In one embodiment, polypeptides have been engineered to convert an indole and serine or threonine to an NCAA, UAA or other chemical. For example, 4-nitroindole can be used in the production of chemical entities when reacted with a TrpB variant of the disclosure (see, e.g., scheme 1). Because the nitro substituent on the 4-nitroindole creates a steric impediment to substrate binding, and also withdraws electron density from the indole moiety, the reaction provides for the production of 4-nitrotryptophan. Since the indole is a nucleophile in this reaction manifold, electron withdrawing substituents are intrinsically deactivating. The compound 4-nitroTrp is a biosynthetic and chemical precursor to thaxtomin A, a potentially useful agrochemical. Additionally, 4-nitroTrp is a chemical precursor to the tumor-promoter indolactam V (see, Table A).

Scheme 1

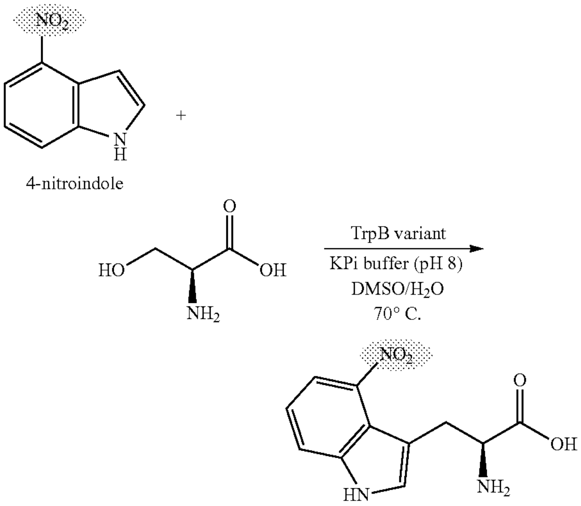

4-nitroindole 4-nitroTrp

KPi = potassium phosphate

TABLE A

| Products synthesized from 4-nitroTrp |
|---|
| 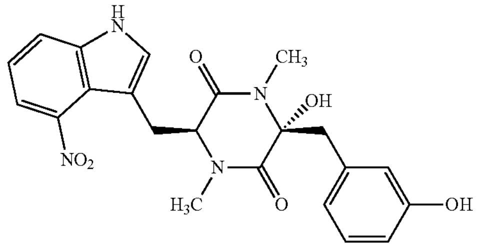 |
| thaxtomin A |
| 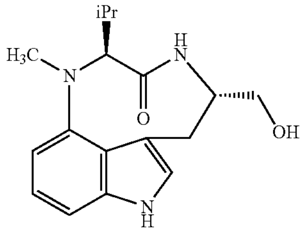 |
| indolactam V |

While the TrpB mutants will be described in more detail below, it is understood that polypeptides of the disclosure may contain one or more modified amino acids. Amino acid (s) are modified, for example, co-translationally or post-translationally during recombinant production (e.g., N-linked glycosylation at N—X—S/T motifs during expression in mammalian cells) or modified by synthetic means.

The disclosure demonstrates the engineering of TrpB through directed evolution to provide a β-subunit that has biological activity independent of TrpA and which can produce tryptophan and/or NCAAs, UAAs or other chemical entities from suitable substrates. For example, the evolution of TrpB into TrpB-mutants shows that members of the TrpB family can be evolved by point mutations and screening for function on various substrates and various products production.

Referring to the sequence comparison of various TrpB subunits in FIG. 2, SEQ ID NO:2 includes the amino acid sequence of TrpB isolated from *Pyroccocus furiosus* designated PfTrpB. SEQ ID NO: 4 provides the amino acid sequence of wild-type TrpB from *Archaeoglobus fulgidus*. This wild-type TrpB designated AfTrpB shares 72% amino acid sequence identity to PfTrpB (SEQ ID NO:2). SEQ ID NO: 6 includes the amino acid sequence of wild-type TrpB from *Thermotoga maritima*. This wild-type TrpB is designated TmTrpB and shares 64% amino acid sequence identity to PfTrpB (SEQ ID NO: 2). SEQ ID NO: 8 includes the amino acid sequence of wild-type TrpB from *Escherichia coli*. This wild-type TrpB is designated EcTrpB and shares 57% amino acid sequence identity to PfTrpB (SEQ ID NO: 2).

The TrpBs set forth in SEQ ID NOs: 2, 4, 6, and 8 are closely related to one another and show a high degree of sequence identity and activity. The sequences can be aligned and conserved amino acids identified based upon the alignment. The alignment provided in FIG. 2 identifies "equivalent positions" in the sequences. An equivalent position denotes a position which, on the basis of the alignment of the sequence of the parent TrpB in question with the "reference" TrpB amino acid sequence in question (e.g. SEQ ID NO: 2) so as to achieve juxtapositioning of amino acid residues which are common to both, corresponds most closely to a particular position in the reference sequence in question. This process can cause gaps or insertions to appear in the sequences. In the alignment of FIG. 2, equivalent positions are shown lined up vertically with one another. For example, position 47 in SEQ ID NO: 2 is equivalent or corresponds to position 60 in SEQ ID NO: 4 and position 49 in SEQ ID NO: 6 and position 53 in SEQ ID NO: 8.

Provided herein are engineered mutant TrpB polypeptides capable of producing NCAAs, UAAs and chemical entities. Protein engineering of TrpBs from other sources can be expected to lead to a similar result using the basic alignment and mutation tools described herein. It is well known in the art that amino acid substitutions having a particular effect (e.g. that confer activity toward a new substrate) can have the same effect in closely related proteins. For example, the alignment of the four homologs illustrates the high degree of sequence similarity among the four TrpBs (see, FIG. 2). Moreover, it will be readily apparent based upon the "mutation" row, which exemplary mutations can be and have been made. It has been shown on multiple occasions that amino acid substitutions at equivalent positions in these enzymes have equivalent effects on function. For example, the substitution of M144T and N166D in PfTrpB increases the $k_{cat}$ by at least 2-fold. The same substitution of the equivalent position in AfTrpB, TmTrpB, and EcTrpB, which is M156T/N178D, M145T/N167D, and M149T/N171D (respectively), has the same effect. Additionally, these TrpB polypeptides can be subjected to rounds of directed evolution using the techniques and screens described herein to obtain and/or increase substrate specificity and product generation.

Accordingly, in one embodiment, a mutant TrpB polypeptide is provided that comprises at least 57% identity to SEQ ID NO: 2 and comprises activating mutations at positions 16, 17, 68, 95, 139, 212, 274, 292, 321 and 384 of SEQ ID NO:2 or positions in SEQ ID NO:4 (positions 29, 30, 80, 107, 151, 224, 285, 303, 332, and 395), 6 (positions 18, 19, 69, 96, 140, 213, 274, 292, and 381) or 8 (positions 22, 23, 73, 100, 144, 217, 279, 326, and 390), which correspond to the positions in SEQ ID NO: 2. In one embodiment, the activating mutations are an I16V, E17G, I68V, F95L, M139L, L212P, F274S, T292S, T321A, V384A mutations with respect to SEQ ID NO:2 (129V, P30V, I80V, F107L, M151L, I224P, L285S, T303S, T332A, and R395A for SEQ ID NO: 4; M18V, P19G, I69V, K96L, P140L, L213P, L274S, T292S, and H381A for SEQ ID NO: 6; and M22V, 23G, L73V, R100L, P144L, L217P, Y279S, S326A, and I390A for SEQ ID NO: 8). In another embodiment, the mutant TrpB can include 50, 25, 10, 5 or fewer conservative substitutions in addition to the specific mutations above.

In another embodiment, the mutant TrpB can comprise one or more additional mutations that improve activity. These mutations are selected from the group consisting of mutations at residues 104, 165, 166, 183, 186, 301 and any combination thereof of SEQ ID NO:2; residues 116, 177, 178, 195, 198, 312 and any combination there of SEQ ID NO: 4; residues 105, 166, 167, 184, 187, 301 and any combination thereof of SEQ ID NO: 6; and residues 109, 170, 171, 188, 306 and any combination thereof of SEQ ID NO:8. In another embodiment, the mutant TrpB can comprise one or more additional mutations selected from the group consisting of E104G or E104A, Y165F, N166D, I183F, V186A, Y301H and any combination thereof of SEQ ID NO: 2; residues E116G or E116A, Y177F, N178D, I195F, V198A, Y312H and any combination there of SEQ ID NO: 4; residues E105G or E105A, Y166F, N167D, I184F, V187A, Y301H and any combination thereof of SEQ ID NO: 6; and residues E109G or E109A, C165F, N171D, L188F, F306H and any combination thereof of SEQ ID NO: 8.

In yet another embodiment, a mutant TrpB polypeptide is provided that comprises SEQ ID NO:2 and has at least 50, 25, 10, 5 or fewer conservative substitutions or has about 578 or more identity to SEQ ID NO: 2 and has activating mutations at positions 16, 17, 68, 95, 139, 212, 274, 292, 321 and 384. In one embodiment, the activating mutations are an I16V, E17G, I68V, F95L, M139L, L212P, F274S, T292S, T321A, V384A. In a further embodiment, the mutant TrpB polypeptide comprises one or more additional mutations that improve activity. These mutations are selected from the group consisting of mutations at residues 104, 166, 183, 186 and any combination thereof of SEQ ID NO:2. In a further embodiment, the mutant TrpB can comprise one or more additional mutations selected from the group consisting of E104G or E014A, N166D, I183F, V186A and any combination thereof of SEQ ID NO: 2.

In yet another embodiment, a mutant TrpB polypeptide is provided that comprises SEQ ID NO: 4 and has at least 50, 25, 10, 5 or fewer conservative substitutions or has about 57% or more identity to SEQ ID NO: 4 and has activating mutations at positions 29, 30, 80, 107, 151, 224, 285, 303, 332, and 395. In one embodiment, the activating mutations are an 129V, P30V, I80V, F107L, M151L, I224P, L285S, T303S, T332A, and R395A. In a further embodiment, the mutant TrpB polypeptide comprises one or more additional mutations that improve activity. These mutations are selected from the group consisting of mutations at residues 116, 178, 195, 198 and any combination thereof of SEQ ID NO: 4. In a further embodiment, the mutant TrpB can comprise one or more addition mutations selected from the group consisting of E116G, N178D, I195F, V198A and any combination thereof of SEQ ID NO: 4.

In yet another embodiment, a mutant TrpB polypeptide is provided that comprises SEQ ID NO: 6 and has at least 50, 25, 10, 5 or fewer conservative substitutions or has about 57% or more identity to SEQ ID NO: 6 and has activating mutations at positions 18, 19, 69, 96, 140, 213, 274, 292, and 381. In one embodiment, the activating mutations are an M18V, P19G, I69V, K96L, P140L, L213P, L274S, T292S, and H381A. In a further embodiment, the mutant TrpB polypeptide comprises one or more additional mutations that improve activity. These mutations are selected from the group consisting of mutations at residues 105, 167, 184, 187 and any combination thereof of SEQ ID NO: 6. In a further embodiment, the mutant TrpB can comprise one or more addition mutations selected from the group consisting of E105G, N167D, I184F, V187A and any combination thereof of SEQ ID NO: 6.

In yet another embodiment, a mutant TrpB polypeptide is provided that comprises SEQ ID NO: 8 and has at least 50, 25, 10, 5 or fewer conservative substitutions or has about 57% or more identity to SEQ ID NO: 8 and has activating mutations at positions 22, 23, 73, 100, 144, 217, 279, 326, and 390. In one embodiment, the activating mutations are an M22V, P23G, L73V, R100L, P144L, L217P, Y279S, S326A, and I390A. In a further embodiment, the mutant TrpB polypeptide comprises one or more additional mutations that improve activity. These mutations are selected from the group consisting of mutations at residues 109, 171, 188 and any combination thereof of SEQ ID NO: 8. In a further embodiment, the mutant TrpB can comprise one or more addition mutations selected from the group consisting of E109G, N171D, L188F and any combination thereof of SEQ ID NO: 8.

In yet another embodiment, a mutant TrpB polypeptide is provided that comprises SEQ ID NO: 2 and has at least 50, 25, 10, 5 or fewer conservative substitutions or has about 57%, 60%, 70%, 80%, 85%, 90%, 95%, 98%, or 99% or more identity to SEQ ID NO:2 and has activating mutations at positions 16, 17, 68, 95, 104, 139, 166, 183, 186, 212, 274, 292, 321 and 384. In one embodiment, the activating mutations are an I16V, E17G, I68V, F95L, E104G (or E104A), M139L, N166D, I183F, V186A, L212P, F274S, T292S, T321A, and V384A. In yet another embodiment, a mutant TrpB polypeptide is provided that has or consists of the sequence of SEQ ID NO:2, but has the following mutations: I16V, E17G, I68V, F95L, E104G (or E104A), M139L, N166D, I183F, V186A, L212P, F274S, T292S, T321A, and V384A.

In yet another embodiment, a mutant TrpB polypeptide is provided that comprises SEQ ID NO: 4 and has at least 50, 25, 10, 5 or fewer conservative substitutions or has about 57%, 60%, 70%, 80%, 85%, 90%, 95%, 98%, or 99% or more identity to SEQ ID NO: 4 and has activating mutations at positions 29, 30, 80, 107, 116, 151, 178, 195, 198, 224, 285, 303, 332, and 395. In one embodiment, the activating mutations are an I29V, P30V, I80V, F107L, E116G (or E116A), M151L, N178D, I195F, V198A, I224P, L285S, T303S, T332A, and R395A. In yet another embodiment, a mutant TrpB polypeptide is provided that has or consists of the sequence of SEQ ID NO: 4, but has the following mutations: I29V, P30V, I80V, F107L, E116G (or E116A), M151L, N178D, I195F, V198A, I224P, L285S, T303S, T332A, and R395A.

In yet another embodiment, a mutant TrpB polypeptide is provided that comprises SEQ ID NO: 6 and has at least 50, 25, 10, 5 or fewer conservative substitutions or has about 57%, 60%, 70%, 80%, 85%, 90%, 95%, 98%, or 99% or more identity to SEQ ID NO: 6 and has activating mutations at positions 18, 19, 69, 96, 105, 140, 167, 184, 187, 213, 274, 292, and 381. In one embodiment, the activating mutations are an M18V, P19G, I69V, K96L, E105G (or E105A), P140L, N167D, I184F, V187A, L213P, L274S, T292S, and H381A. In yet another embodiment, a mutant TrpB polypeptide is provided that has or consists of the sequence of SEQ ID NO: 6, but has the following mutations: M18V, P19G, I69V, K96L, E105G (or E105A), P140L, N167D, I184F, V187A, L213P, L274S, T292S, and H381A.

In yet another embodiment, a mutant TrpB polypeptide is provided that comprises SEQ ID NO: 8 and has at least 50, 25, 10, 5 or fewer conservative substitutions or has about 57% or more identity to SEQ ID NO: 8 and has activating mutations at positions 22, 23, 73, 100, 109, 144, 171, 188, 217, 279, 326, and 390. In one embodiment, the activating mutations are an M22V, P23G, L73V, R100L, E109G (or E109A), P144L, N171D, L188F, L217P, Y279S, S326A, and I390A. In yet another embodiment, a mutant TrpB polypeptide is provided that has or consists of the sequence of SEQ ID NO: 8, but has the following mutations: M22V, P23G, L73V, R100L, E109G (or E109A), P144L, N171D, L188F, L217P, Y279S, S326A, and I390A.

"Conservative amino acid substitution" or, simply, "conservative variations" of a particular sequence refers to the replacement of one amino acid, or series of amino acids, with essentially identical amino acid sequences. One of skill will recognize that individual substitutions, deletions, or additions which alter, add, or delete a single amino acid or a percentage of amino acids in an encoded sequence result in "conservative variations" where the alterations result in the deletion of an amino acid, addition of an amino acid, or substitution of an amino acid with a chemically similar amino acid.

Conservative substitution tables providing functionally similar amino acids are well known in the art. For example, one conservative substitution group includes Alanine (A), Serine (S), and Threonine (T). Another conservative substitution group includes Aspartic acid (D) and Glutamic acid (E). Another conservative substitution group includes Asparagine (N) and Glutamine (Q). Yet another conservative substitution group includes Arginine (R) and Lysine (K). Another conservative substitution group includes Isoleucine, (I) Leucine (L), Methionine (M), and Valine (V). Another conservative substitution group includes Phenylalanine (F), Tyrosine (Y), and Tryptophan (W).

Thus, "conservative amino acid substitutions" of a listed polypeptide sequence (e.g., SEQ ID NOs: 2, 4, 6, or 8) include substitutions of a percentage, typically less than 10%, of the amino acids of the polypeptide sequence, with a conservatively selected amino acid of the same conservative substitution group. Accordingly, a conservatively substituted variation of a polypeptide of the disclosure can contain 100, 75, 50, 25, or 10 substitutions with a conservatively substituted variation of the same conservative substitution group.

It is understood that the addition of sequences which do not alter the encoded activity of a nucleic acid molecule, such as the addition of a non-functional or non-coding sequence, is a conservative variation of the basic nucleic acid. One of skill in the art will appreciate that many conservative variations of the nucleic acid constructs, which are disclosed, yield a functionally identical construct. For example, owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the polypeptides provided herein.

The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. As used interchangeably herein a "TrpB mutant activity", "mutant TrpB activity", "biological activity of TrpB mutant" or "functional activity of TrpB mutant", refers to an activity exerted by a TrpB mutant polypeptide of the disclosure on a TrpB substrate, as determined in vivo or in vitro, according to standard techniques. The biological activity of TrpB mutants is described herein as, for example, the ability to utilize indole or analogs thereof and L-serine or L-threonine in the generation of NCAAs, UAAs or other desired chemical entities. Other measurements are described in the examples below.

It will be appreciated by those skilled in the art that due to the degeneracy of the genetic code, a multitude of nucleotide sequences encoding mutant TrpBs of the disclosure may be produced, some of which bear substantial identity to the nucleic acid sequences explicitly disclosed herein (e.g., SEQ ID NO:1, 3, 5, or 7). For instance, codons AGA, AGG, CGA, CGC, CGG, and CGU all encode the amino acid arginine. Thus, at every position in the nucleic acids of the disclosure where an arginine is specified by a codon, the codon can be altered to any of the corresponding codons described above without altering the encoded polypeptide. It is understood that U in an RNA sequence corresponds to T in a DNA sequence.

"Conservative variants" are proteins or enzymes in which a given amino acid residue has been changed without altering overall conformation and function of the protein or enzyme, including, but not limited to, replacement of an amino acid with one having similar properties, including polar or non-polar character, size, shape, and charge. Amino acids other than those indicated as conserved may differ in a protein or enzyme so that the percent protein or amino acid sequence similarity between any two proteins of similar function may vary and can be, for example, at least 30%, at least 50%, at least 70%, at least 80%, at least 90%, at least 95%, at least 98%, or at least 99%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that result in the highest sequence similarity.

"Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that result in the highest sequence similarity. For example, the "identity" or "percent identity" with respect to a particular pair of aligned amino acid sequences can refer to the percent amino acid sequence identity that is obtained by ClustalW analysis (version W 1.8 available from European Bioinformatics Institute, Cambridge, UK), counting the number of identical matches in the alignment and dividing such number of identical matches by the greater of (i) the length of the aligned sequences, and (ii) 96, and using the following default ClustalW parameters to achieve slow/accurate pairwise alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins" in "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Nat'l. Acad. Sci. USA 89:10915-10919 (each of which is incorporated by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul et al. (1997) Nucl. Acids Res. 25:3389-3402 (incorporated by reference herein), and made available to the public at the National Center for Biotechnology Information (NCBI) website. Optimal alignments, including multiple alignments, can be prepared using, e.g., PSI-BLAST, available through the NCBI website and described by Altschul et al. (1997) Nucl. Acids Res. 25:3389-3402 (incorporated by reference herein).

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. For example, in SEQ ID NO: 2, position 12 is P, position 13 is E, etc. When a test sequence is optimally aligned with SEQ ID NO: 2, a residue in the test sequence that aligns with the P at position 12 is said to "correspond to position 12" of SEQ ID NO: 2. Owing to deletions, insertion, truncations, fusions, etc., that must be taken into account when determining an optimal alignment, in general the amino acid residue number in a test sequence as determined by simply counting from the N-terminal end will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

Non-conservative modifications of a particular polypeptide are those, which substitute any amino acid not characterized as a conservative substitution. For example, any substitution which crosses the bounds of the six groups set forth above. These include substitutions of basic or acidic amino acids for neutral amino acids, (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid. Basic side chains include lysine (K), arginine (R), histidine (H); acidic side chains include aspartic acid (D), glutamic acid (E); uncharged polar side chains include glycine (G), asparagine (N), glutamine (Q), serine (S), threonine (T), tyrosine (Y), cysteine (C); nonpolar side chains include alanine (A), valine (V), leucine (L), isoleucine (I), proline (P), phenylalanine (F), methionine (M), tryptophan (W); beta-branched side chains include threonine (T), valine (V), isoleucine (I); aromatic side chains include tyrosine (Y), phenylalanine (F), tryptophan (W), histidine (H).

Accordingly, some amino acid residues at specific positions in a polypeptide are "excluded" from conservative amino acid substitutions. Instead, these restricted amino acids are generally chosen from a specific group or selected amino acids or are not substituted or mutated at all. For example, with reference to FIG. 2, the line indicated as "Mutations" are positions that include specific and/or non-conservative mutations.

A polynucleotide, polypeptide, or other component is "isolated" or "purified" when it is partially or completely separated from components with which it is normally associated (other proteins, nucleic acids, cells, synthetic reagents, etc.). A nucleic acid or polypeptide is "recombinant" when it is artificial or engineered, or derived from an artificial or engineered protein or nucleic acid through the process of mutation. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant or engineered mutant of a naturally occurring gene, is recombinant. For example, an "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4kb, 3kb, 2kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

The disclosure envisions multi-unit polypeptides. Such a multi-unit polypeptide would comprise for example: TrpA-mTrpB-mTrpB-TrpA. The tryptophan-α (TrpA) domain (and sequences thereof) of TrpS for each of *Pyrococcus furiosus, Archaeoglobus fulgidus, Thermotoga maritima*, and *Escherichia coli* are well known in the art.

In other embodiments, isolated nucleic acid molecules are provided. In one embodiment, the disclosure provides a novel family of isolated or recombinant polynucleotides referred to herein as "TrpB mutant polynucleotides" or "TrpB mutant nucleic acid molecules." TrpB mutant polynucleotide sequences are characterized by the ability to encode a TrpB mutant polypeptide. In general, the disclosure includes any nucleotide sequence that encodes any of the TrpB mutant polypeptides described herein. In some aspects of the disclosure, a TrpB mutant polynucleotide that encodes a TrpB mutant polypeptide with TrpB mutant activity is provided. The terms "polynucleotide," "nucleotide sequence," and "nucleic acid molecule" are used to refer to a polymer of nucleotides (A, C, T or U, G, etc. or naturally occurring or artificial nucleotide analogues), e.g., DNA or RNA, or a representation thereof, e.g., a character string, etc., depending on the relevant context. A given polynucleotide or complementary polynucleotide can be determined from any specified nucleotide sequence.

In one embodiment, the TrpB mutant polynucleotides comprise recombinant or isolated forms of naturally occurring nucleic acids isolated from an organism, which have been mutated by, for example, directed evolution. Exemplary TrpB polynucleotides include those that encode the wild-type polypeptides set forth in SEQ ID NO: 2, 4, 6, or 8. In another aspect of the disclosure, TrpB mutant polynucleotides are produced by diversifying, e.g., recombining and/or mutating one or more naturally occurring, isolated, or recombinant TrpB polynucleotides. As described in more detail elsewhere herein, it is often possible to generate diversified TrpB mutant polynucleotides encoding TrpB mutant polypeptides with superior functional attributes, e.g., increased catalytic function, increased stability, novel substrate or product production, or higher expression level, than a TrpB polynucleotide used as a substrate or parent in the diversification process.

The polynucleotides of the disclosure have a variety of uses in, for example, recombinant production (i.e., expression) of the TrpB mutant polypeptides of the disclosure and as substrates for further diversity generation, e.g., recombination reactions or mutation reactions to produce new and/or improved TrpB mutant homologues, and the like.

It is important to note that certain specific, substantial, and credible utilities of TrpB mutant polynucleotides do not require that the polynucleotide encodes a polypeptide with substantial TrpB mutant activity or even TrpB mutant activity. For example, TrpB mutant polynucleotides that do not encode active enzymes can be valuable sources of parental polynucleotides for use in diversification procedures to arrive at TrpB mutant polynucleotide with desirable functional properties (e.g., high $K_{cat}$ or $K_{cat}/K_m$, low $K_m$, high stability toward heat or other environmental factors, high transcription or translation rates, resistance to proteolytic cleavage, etc.).

TrpB mutant polynucleotides, including nucleotide sequences that encode TrpB polypeptides and variants thereof, fragments of TrpB mutant polypeptides, related fusion proteins, or functional equivalents thereof, are used in recombinant DNA molecules that direct the expression of the TrpB mutant polypeptides in appropriate host cells, such as bacterial cells. Due to the inherent degeneracy of the genetic code, other nucleic acid sequences which encode substantially the same or a functionally equivalent amino acid sequence can also be used to clone and express the TrpB mutant polynucleotides.

The term "host cell", as used herein, includes any cell type which is susceptible to transformation with a nucleic acid construct. The term "transformation" means the introduction of a foreign (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may include regulatory or control sequences, such as start, stop, promoter, signal, secretion, or other sequences used by the genetic machinery of the cell. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang et al. (1991) Gene 105:61-72; incorporated by reference herein). Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508; incorporated by reference herein) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA, respectively. The preferred stop codon for monocotyledonous plants is UGA, whereas insects and *E. coli* prefer to use UAA as the stop codon (Dalphin et al. (1996) Nucl. Acids Res. 24: 216-218; incorporated by reference herein). Methodology for optimizing a nucleotide sequence for expression in a plant is provided, for example, in U.S. Pat. No. 6,015,891, and the references cited therein (incorporated herein by reference).

In some embodiments, nucleic acid molecules of the disclosure include: (a) a nucleic acid molecule which encodes a polypeptide comprising the amino acid sequence selected from the group consisting of SEQ ID NO: 10, 12, 14, 16, 18, 20, 22, 24, and 26; (b) a nucleic acid molecule which encodes a polypeptide consisting of the amino acid sequence selected from the group consisting of SEQ ID NO: 10, 12, 14, 16, 18, 20, 22, 24, and 26; (c) a nucleic acid molecule which hybridizes under stringent conditions to a polynucleotide consisting of a sequence selected from the group consisting of SEQ ID NO: 1, 3, 5, 7, 9, 11, 13, 15, 17, 19, 21, 23, and 25 and which encodes a TrpB mutant polypeptide that as an independent subunit catalyze the production of NCAAs, UAAs from an indole or indole derivative and L-serine or L-threonine; or (d) a nucleic acid molecule which hybridizes under stringent conditions to a polynucleotide consisting of sequence selected from the group consisting of SEQ ID NO: 1, 3, 5, 7, 9, 11, 13, 15, 17, 19, 21, 23, and 25 and which encodes a polypeptide that comprises the amino acid sequence selected from the group consisting of SEQ ID NO: 10, 12, 14, 16, 18, 20, 22, 24, and 26.

In one embodiment, an isolated nucleic acid molecule that includes a nucleic acid molecule of the disclosure and a nucleotide sequence encoding a heterologous polypeptide or peptide is provided. For example, a coding sequence for a tag (e.g., a polyHis Tag) can be linked to a polynucleotide of the disclosure.

In general, the disclosure includes any TrpB mutant polypeptide encoded by a modified TrpB polynucleotide derived by mutation, recursive sequence recombination, and/or diversification of the polynucleotide sequences described herein, wherein the polypeptide has novel substrate specificity, can catalyze a reaction independent of the TrpA subunit and can produce NCAAs, UAAs and/or other novel/desired chemical entities including intermediates for further metabolic and/or chemical modifications.

A nucleic acid molecule of the disclosure, e.g., a nucleic acid molecule that encodes a polypeptide set forth in any of SEQ NOs:2, 4, 6, 8, 10, 12, 14, 16, 18, 20, 22, 24, or 26, or having the nucleotide sequence of set forth in any of SEQ ID NOs: 1, 3, 5, 7, 9, 11, 13, 15, 17, 19, 21, 23, or 25, or a portion thereof, can be isolated using standard molecular biology techniques and the sequence information provided herein.

A nucleic acid of the disclosure can be amplified using CDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer. In some embodiments, an isolated nucleic acid molecule of the disclosure comprises a nucleic acid molecule which is a complement of a nucleotide sequence encoding a polypeptide having a sequence selected from the group consisting of SEQ NOs: 10, 12, 14, 16, 18, 20, 22, 24, and 26. In still another embodiment, an isolated nucleic acid molecule of the disclosure comprises a nucleotide sequence which is at least about 50%, 54%, 55%, 60%, 62%, 65%, 70%, 75%, 78%, 80%, 85%, 86%, 90%, 95%, 97%, 98% or more identical to the nucleotide sequence encoding a polypeptide selected from the group consisting of SEQ NOs: 2, 4, 6, 8, 10, 12, 14, 16, 18, 20, 22, 24, and 26, and having mTrpB activity or having the nucleotide sequence selected from the group consisting of SEQ ID NOs: 9, 11, 13, 15, 17, 19, 21, 23, and 25.

Nucleic acid molecules are "hybridizable" to each other when at least one strand of one polynucleotide can anneal to another polynucleotide under defined stringency conditions. Stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.) require correspondingly less overall complementarity between the hybridizing sequences (1×SSC is 0.15 M NaCl, 0.015 M Na citrate). Nucleic acid molecules that hybridize include those which anneal under suitable stringency conditions and which encode polypeptides or enzymes having the same function, such as the ability to catalyze the conversion of an indole or indole derivative and L-serine or L-threonine to a NCAA or UAA. Further, the term "hybridizes under stringent conditions" is intended to describe conditions for hybridization and washing under which nucleotide sequences at least 60% or greater in homology to each other typically remain hybridized to each other. Preferably, the conditions are such that sequences at least about 70%, more preferably at least about 80%, even more preferably at least about 85% or 90% homologous to each other typically remain hybridized to each other.

The skilled artisan will appreciate that changes can be introduced by mutation into the nucleotide sequences of any nucleic acid sequence provided herein or any nucleic acid encoding a polypeptide of the disclosure.

Also contemplated are those situations where it is desirable to alter the activity of a parent polypeptide such that the polypeptide has new or increased activity on a particular substrate. It is understood that these amino acid substitutions will generally not constitute "conservative" substitutions. Instead, these substitutions constitute non-conservative substitutions introduced into a sequence in order to obtain a new or improved activity. For example, a polypeptide set forth SEQ ID NOs: 10, 12, 14, 16, 18, 20, 22, 24, or 26 include specific amino acid substitutions that include one or more mutations at a position selected from the group consisting of 16, 17, 68, 95, 104, 139, 166, 183, 186, 212, 274, 292, 321, 384 compared to the wild-type sequence of SEQ ID NO: 2 and which mutations contribute to the alteration of the activity of the polypeptide.

It is also understood that an isolated nucleic acid molecule encoding a polypeptide having identity to or homologous to a polypeptide of SEQ ID NO: 2, 4, 6, 8, 10, 12, 14, 16, 18, 20, 22, 24, or 26 can be created by introducing one or more nucleotide substitutions, additions, or deletions into the nucleotide sequence encoding the particular polypeptide, such that one or more amino acid substitutions, additions or deletions are introduced into the encoded protein. Mutations can be introduced into the nucleic acid sequence by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions.

Mutational methods of generating diversity include, for example, site-directed mutagenesis (Ling et al. (1997) "Approaches to DNA mutagenesis: an overview" Anal Biochem. 254 (2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100:468-500 (1983); Methods in Enzymol. 154:329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100:468-500; and Zoller &

Smith (1987) "Oligonucleotide-directed mutagenesis: a simple method using two oligonucleotide primers and a single-stranded DNA template" Methods in Enzymol. 154: 329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787; Nakamaye & Eckstein (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16: 791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999) (each of which is incorporated by reference).

Additional suitable methods include point mismatch repair (Kramer et al. (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh & Henikoff (1986) "Use of oligonucleotides to generate large deletions" Nucl. Acids Res. 14: 5115), restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34: 315-323; and Grundstrom et al. (1985) "Oligonucleotide-directed mutagenesis by microscale 'shot-gun' gene synthesis" Nucl. Acids Res. 13: 3305-3316); double-strand break repair (Mandecki (1986); Arnold (1993) "Protein engineering for unusual environments" Current Opinion in Biotechnology 4:450-455; and "Oligonucleotide-directed double-strand break repair in plasmids of Escherichia coli: a method for site-specific mutagenesis" Proc. Natl. Acad. Sci. USA, 83:7177-7181) (each of which is incorporated by reference). Additional details on many of the above methods can be found in Methods in Enzymology Volume 154, which also describes useful controls for trouble-shooting problems with various mutagenesis methods.

Additional details regarding various diversity generating methods can be found in the following U.S. patents, PCT publications, and EPO publications: U.S. Pat. No. 5,605,793 to Stemmer (Feb. 25, 1997), "Methods for In vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/13487 by Stemmer et al., "Methods for Optimization of Gene Therapy by Recursive Sequence Shuffling and Selection;" WO 00/00632, "Methods for Generating Highly Diverse Libraries;" WO 00/09679, "Methods for Obtaining in vitro Recombined Polynucleotide Sequence Banks and Resulting Sequences;" WO 98/42832 by Arnold et al., "Recombination of Polynucleotide Sequences Using Random or Defined Primers;" WO 99/29902 by Arnold et al., "Method for Creating Polynucleotide and Polypeptide Sequences;" WO 98/41653 by Vind, "An in vitro Method for Construction of a DNA Library;" WO 98/41622 by Borchert et al., "Method for Constructing a Library Using DNA Shuffling;" WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" WO 01/23401 by Welch et al., "Use of Codon-Varied Oligonucleotide Synthesis for Synthetic Shuffling;" and WO 01/64864 "Single-Stranded Nucleic Acid Template-Mediated Recombination and Nucleic Acid Fragment Isolation" by Affholter (each of which is incorporated by reference).

Also provided are recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), or the like, into which a nucleic acid sequence of the disclosure has been inserted, in a forward or reverse orientation. In a preferred aspect of this embodiment, the construct further comprises regulatory sequences including, for example, a promoter operably linked to the sequence. Large numbers of suitable vectors and promoters are known to those of skill in the art, and are commercially available.

Accordingly, in other embodiments, vectors that include a nucleic acid molecule of the disclosure are provided. In other embodiments, host cells transfected with a nucleic acid molecule of the invention, or a vector that includes a nucleic acid molecule of the invention, are provided. Host cells include eucaryotic cells such as yeast cells, insect cells, or animal cells. Host cells also include prokaryotic cells such as bacterial cells.

The terms "vector", "vector construct" and "expression vector" mean the vehicle by which a DNA or RNA sequence (e.g. a foreign gene) can be introduced into a host cell, so as to transform the host and typically express (e.g. transcription and translation) the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can be readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

Polynucleotides provided herein can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell, and, if replication is desired, which is replicable and viable in the relevant host can be used.

Vectors can be employed to transform an appropriate host to permit the host to express a mutant TrpB polypeptide or protein. Examples of appropriate expression hosts include: bacterial cells, such as *E. coli, B. subtilis, Streptomyces*, and *Salmonella typhimurium*; fungal cells, such *as Saccharomyces cerevisiae, Pichia pastoris*, and *Neurospora crassa*; insect cells such as Drosophila and *Spodoptera frugiperda*; mammalian cells such as CHO, COS, BHK, HEK 293 br Bowes melanoma; or plant cells or explants, etc.

In bacterial systems, a number of expression vectors may be selected depending upon the use intended for the mutant TrpB polypeptide. For example, when large quantities of mutant TrpB polypeptide or fragments thereof are needed for commercial production or for induction of antibodies, vectors which direct high-level expression of fusion proteins that are readily purified can be desirable. Such vectors include, but are not limited to, multifunctional *E. coli* cloning and expression vectors such as BLUESCRIPT (Stratagene), in which the mutant TrpB polypeptide coding sequence may be ligated into the vector in-frame with sequences for the amino-terminal Met and the subsequent 7 residues of beta-galactosidase so that a hybrid protein is produced; pIN vectors (Van Heeke & Schuster (1989) J. Biol. Chem. 264: 5503-5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH may be used for production of the TrpB polypeptides of the invention. For reviews, see Ausubel (supra) and Grant et al. (1987) Methods in Enzymology 153:516-544 (incorporated herein by reference).

Also provided are engineered host cells that are transduced (transformed or transfected) with a vector provided herein (e.g., a cloning vector or an expression vector), as well as the production of polypeptides of the disclosure by recombinant techniques. The vector may be, for example, a plasmid, a viral particle, a phage, etc. The engineered host cells can be cultured in conventional nutrient media modified as appropriate for activating promoters, selecting transformants, etc. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) Culture of Animal Cells: A Manual of Basic Technique, 3rd ed. (Wiley-Liss, New York) and the references cited therein.

In other embodiments, methods for producing a cell that converts an indole or indole derivative a substrate (e.g., L-serine or L-threonine) to a desired chemical entity, are provided. Such methods generally include transforming a cell with an isolated nucleic acid molecule (or vector containing the same) encoding a mutant TrpB polypeptide of the disclosure.

In other embodiments, methods for producing NCAAs, UAAs and desired chemical entities are provided. The methods include: (a) providing a cell containing a nucleic acid construct comprising a nucleotide sequence that encodes a mutant TrpB, (b) culturing the cell in the presence of a suitable indole or indole derivative and L-serine or L-threonine and under conditions where the mutant TrpB is expressed at an effective level; and (c) producing an NCAA, UAA or chemical entity. In another embodiments, the methods include: (a) providing a cell containing a nucleic acid construct comprising a nucleotide sequence that encodes a mutant TrpB, (b) culturing the cells under conditions to express the mTrpB; (c) isolating the mTrpB to obtain a substantially purified mTrpB preparation or preparing a disrupted or cell-free preparation of mTrpB; (d) contacting/Admixing the mTrpB with a suitable indole or indole derivative and L-serine; and (c) producing an NCAA, UAA or chemical entity.

In another embodiment, methods of producing di-substituted tryptophan analogs, 4-, 5-, 6- or 7-nitrotryptophan or tryptophan analogs thereof are provided. The method includes (a) providing L-serine, an indole or indole derivative or nitro-indole, and a mutant TrpB of the disclosure. Admixing the components for sufficient time and under suitable conditions to produce the di-substituted tryptophan analogs, 4-, 5-, 6- or 7-nitrotryptophan or tryptophan analogs.

TrpB from *P. furiosus* and *Thermotoga maritima* are optimal parents for directed evolution, due to their high thermostability. The wild-type proteins (PfTrpB and TmTrpB), as well as the already-generated stand-alone variants were tested for their ability to produce 4-nitroTrp. The wild-type enzymes exhibited only trace activity. In addition, many of the variants formed a significant amount of the isotryptophan (1, FIG. 4) as a side product. One variant, Pf2B9 (SEQ ID NO: 10), provided 18% conversion of 4-nitroindole to 4-nitroTrp. Notably, this variant, which has eight mutations from wild-type PfTrpB, was initially evolved for activity with indole and threonine (Thr). Thus, the fortuitous improvement for 4-nitroindole and Ser lent support to the hypothesis that optimizing a catalyst for production of 4-nitroTrp would provide simultaneous gains for other substrates.

The TrpB catalytic mechanism was analyzed in order to identify what might be limiting conversion of 4-nitroindole. TrpB uses the cofactor pyridoxal phosphate (PLP), which is covalently bound to a lysine residue in the active site (FIG. 4A, intermediate I). The lysine is displaced by Ser (intermediate II), which then undergoes $\alpha$-deprotonation (intermediate III) and $\beta$-elimination to generate the active electrophile, amino-acrylate IV. Ideally, this would be attacked by the nucleophilic substrate, such as 4-nitroindole, to form the Trp product.

Figures 6A, 6B:
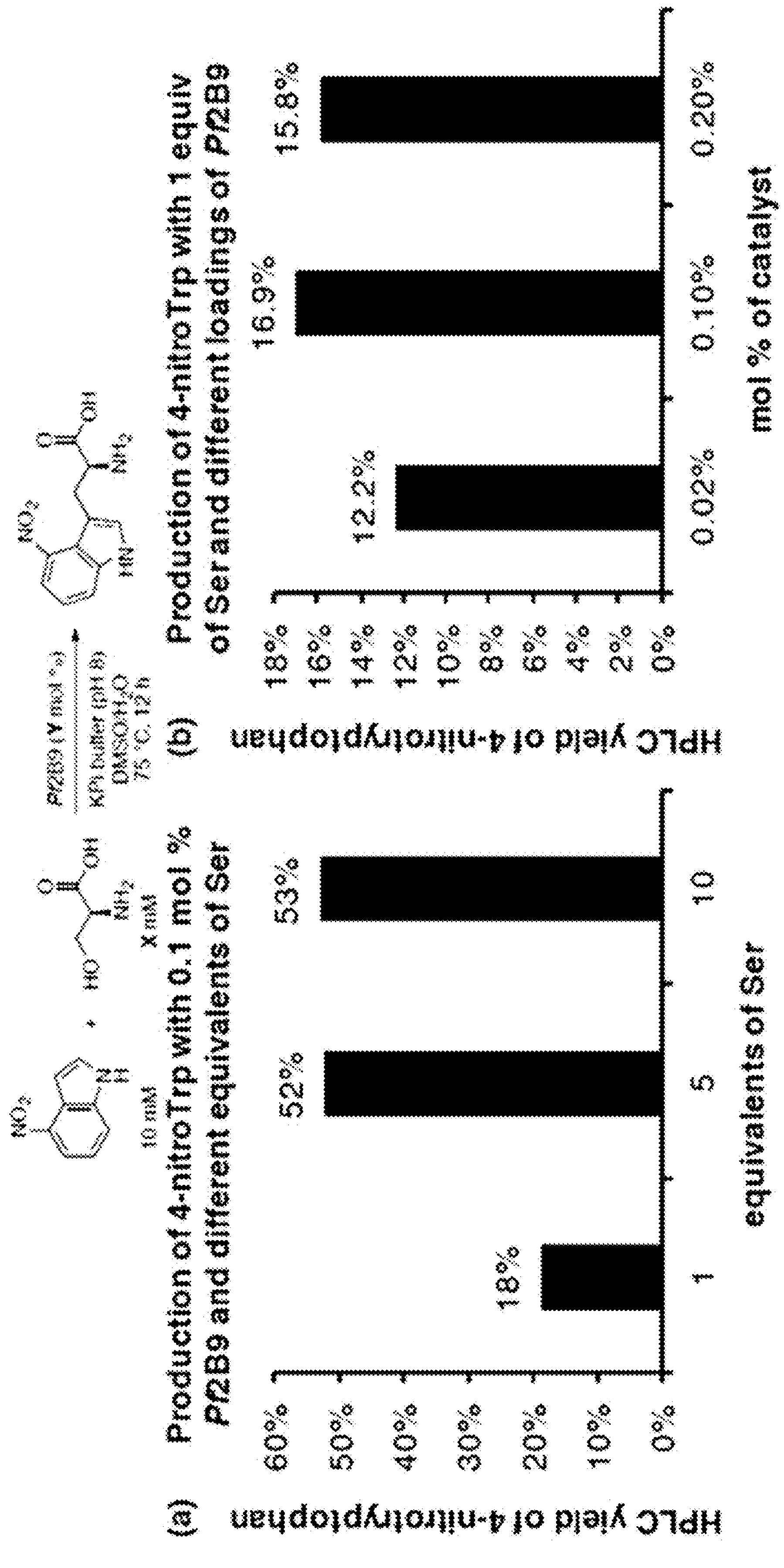
FIG. 6A-B shows production of 4-nitrotryptophan under different conditions. (A) HPLC yield with 0.02, 0.05, 0.1, and 0.2 mol % of Pf2B9 (1 equiv of Ser). (B) HPLC yield with 1, 5, and 10 equivalents of Ser (0.1 mol % of Pf2B9).

Increasing the catalyst loading had a negligible effect on production of 4-nitroTrp (FIG. 6A), but the Ser was completely consumed at the end of the reaction period. By contrast, production of 4-nitroTrp was improved by addition of excess Ser (FIG. 6B). These observations are consistent with the known side reaction in which the amino-acrylate is ejected from the PLP cofactor and undergoes hydrolytic decomposition to pyruvate (FIG. 4B). In addition, and especially at early reaction times, formation of isotryptophan 1 was observed (FIG. 4C), in which 4-nitroindole atom (N1) rather than the desired carbon atom (C3). While this reaction appears to be reversible, it undoubtedly slows the desired reaction. The goal was to engineer a TrpB that would rapidly and quantitatively convert equimolar amounts of 4-nitroindole and Ser into 4-nitroTrp with perfect regio- and enantioselectivity.

Figure 5A:
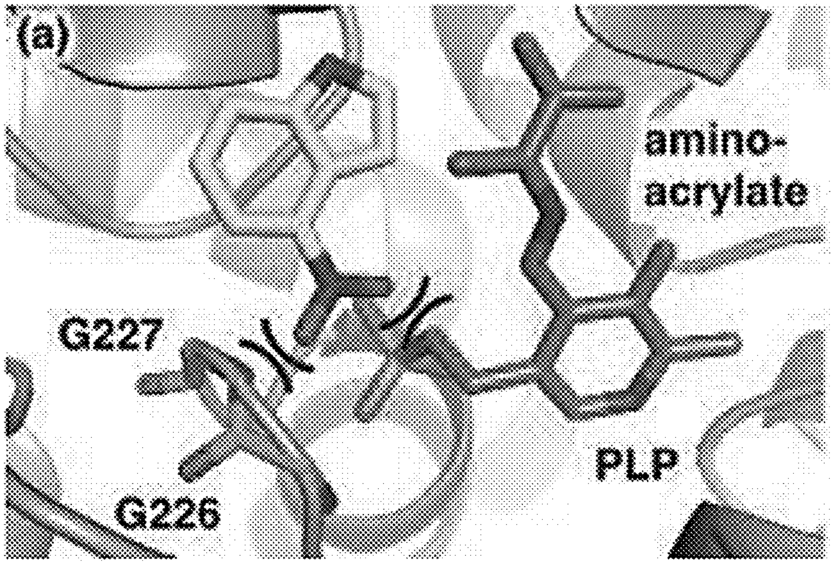
FIG. 5A-B shows a model of 4-nitroindole in the active site of Pf2B9 (PDB ID: 5VM5). (A) Nitro group clashes with the protein backbone and the PLP cofactor. (B) Alternative view showing side-chains extending in to the active site and hydrogen bond with E104.
Figure 5B:
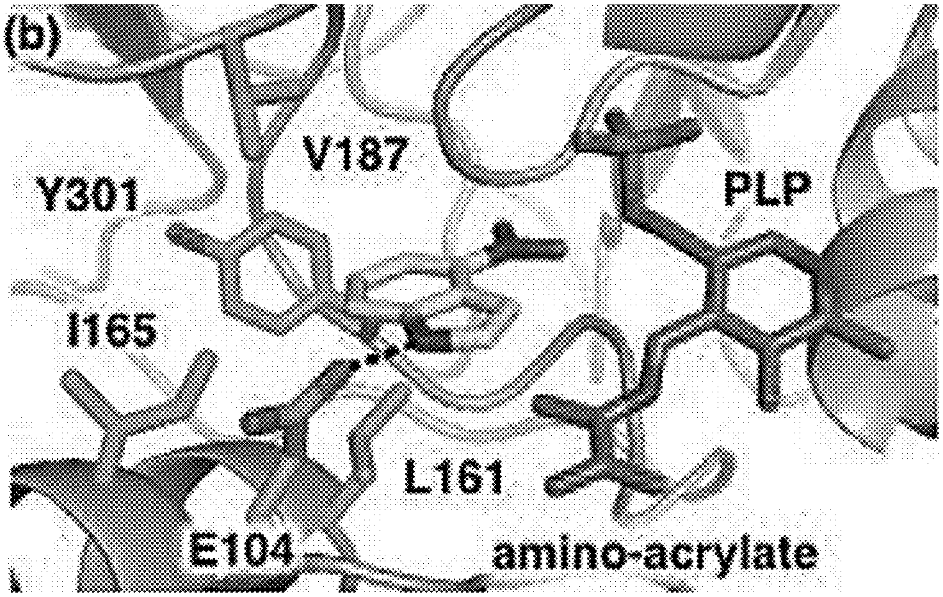

Small site-saturation mutagenesis libraries were developed that could be screened by high-performance liquid chromatography (HPLC). 4-nitroindole was modeled into the binding pose necessary to achieve C—C bond formation, in the hope of identifying steric clashes that could be alleviated by mutations. The model suggested that the nitro group was clashing with the protein main chain as well as with the PLP cofactor (FIG. 5A). Nonetheless, four residues were identified whose side chains extended into the indole-binding pocket: L161, I165, V187, and Y301 (FIG. 5B). The sidechain of E104 also occupies the active site, but this residue is thought to bind indole through the NH moiety, thereby promoting attack from C3. Since this residue is universally conserved in TrpB homologs, and 4-nitroindole already suffers from poor regioselectivity, mutagenesis at this position was avoided. It was hypothesized that mutation at the other four positions could create space for 4-nitroindole to bind in an alternative pose that relieved the steric clashes but still allowed for attack of the amino-acrylate.

Figure 7:
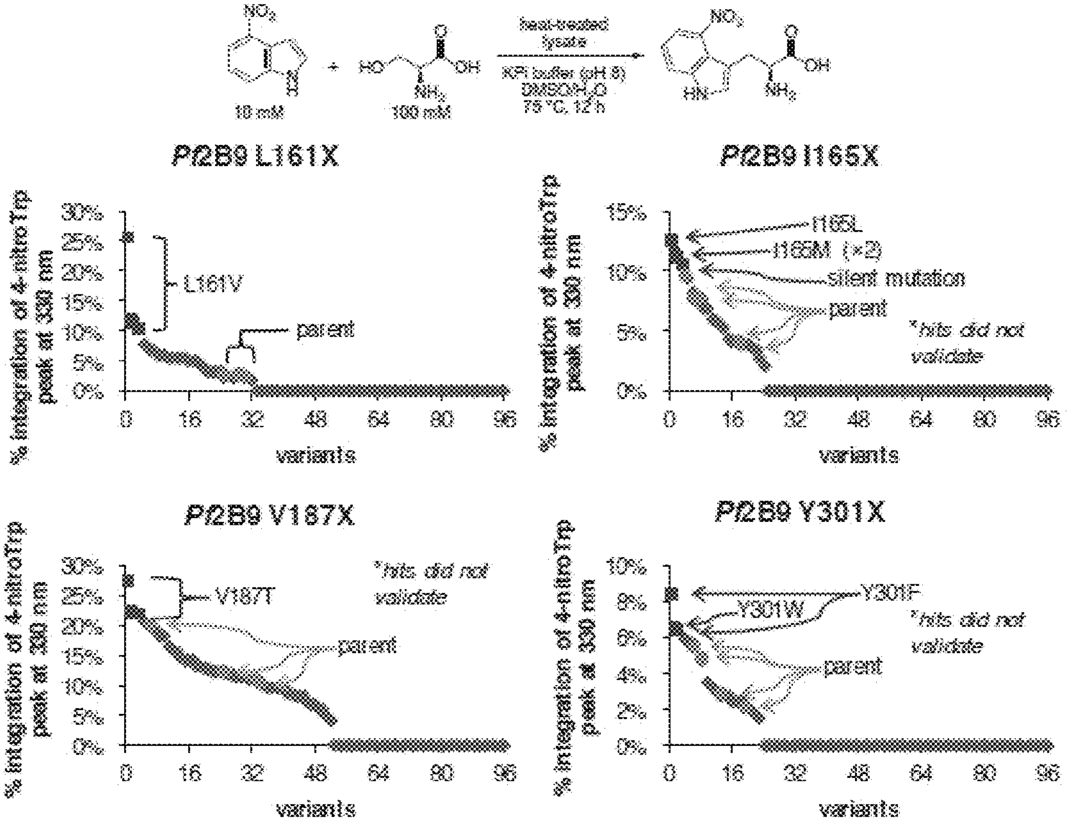
FIG. 7 shows site-saturation of Pf2B9 at L161, I165, V187, and Y301 for production of 4-nitrotryptophan. Product formation was measured by HPLC.

Suprisingly, mutations at the targeted residues were almost uniformly deleterious (FIG. 7), with the exception of L161V, which boosted the yield of 4-nitroTrp to 25%. While this improvement is modest, the mutation also suppressed the formation of isotryptophan 1. It is worth noting that although the side-chain of valine is indeed smaller than that of leucine, mutation of this position to alanine is deleterious.

Figure 8:
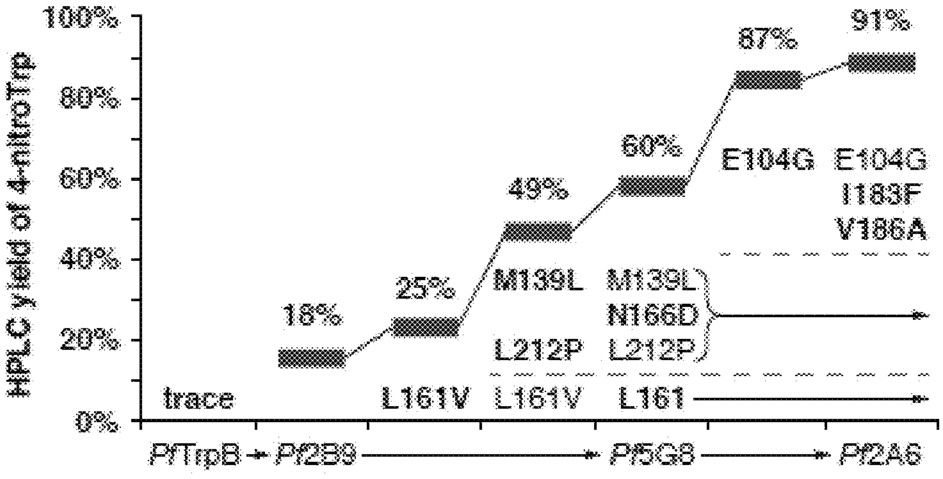
FIG. 8 shows evolutionary progression in production of 4-nitroTrp. Mutations in bold were added in the corresponding round of mutagenesis and screening. Dashed lines denote a new round of random mutagenesis. The horizontal axis indicates catalyst designations.

A random mutagenesis library, generated by error-prone polymerase chain reaction, was used and identified a variant, with mutations M139L and L212P, that almost doubled the HPLC yield of 4-nitroTrp to 49% (FIG. 8). A library which randomly recombined those two mutations and N166D, a beneficial mutation, was tested. The active-site L161V mutation was randomly varied, since its effect had been comparatively minor. Indeed, in the best variant from this library (Pf5G8; SEQ ID NO: 14), the active-site mutation had reverted back to leucine and the other three mutations were retained. This variant formed 4-nitroTrp in 60% HPLC yield from equimolar amounts of 4-nitroindole and Ser.

Figure 9:
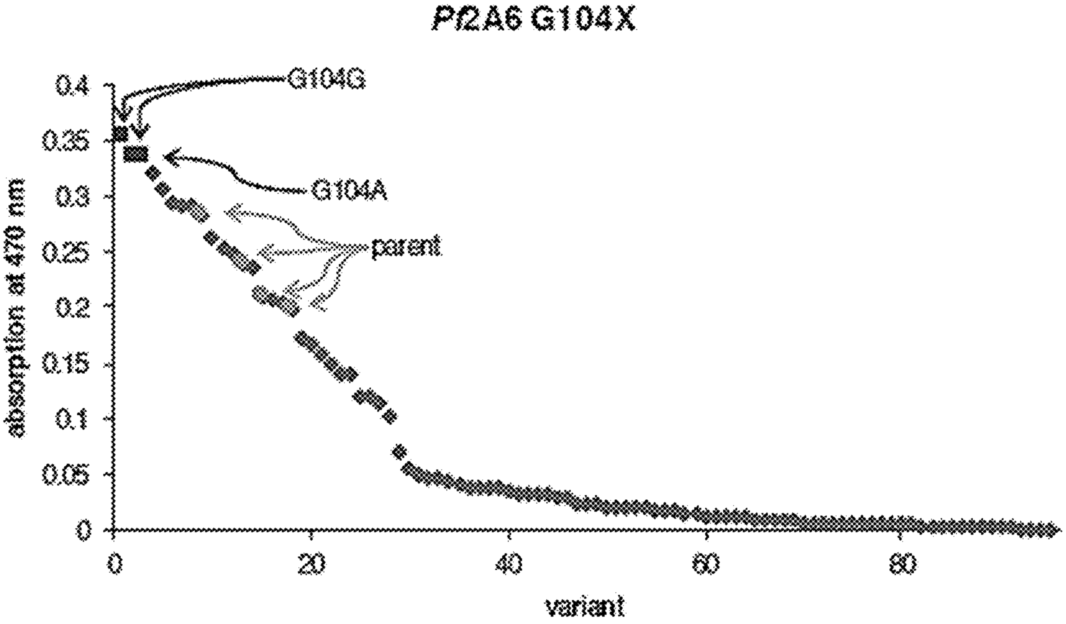
FIG. 9 shows site-saturation of Pf2A6 at position G104 for production of 4-nitrotryptophan. Production was measured on a UV-vis plate reader.

Another random mutagenesis library was generated with Pf5G8 as the parent protein. From this library, two mutations (I183F and V186A) that increased HPLC yield slightly, to ~70%. A further improvement, however, came from a variant bearing the mutation E104G (SEQ ID NO:16), which increased HPLC yield to ~87% and eviscerated the earlier supposition that an H-bonding interaction with 4-nitroindole and the side-chain of E104 would promote the reaction. A recombination library was then screened and it was found that the E104G mutation recombined with I183F and V186A to produce 4-nitroTrp in 91% HPLC yield. A site-saturation library was screened at position 104 and it was determined that glycine at this position was optimal, with Ala yielding similar, but slightly inferior results (FIG. 9).

The identified enzymes Pf5G8 (SEQ ID NO: 14) and Pf2A6 (SEQ ID NO: 18) were also tested against other nitroindole derivatives (Table B). Pf5G8 showed improvement for all substrates compared to Pf2B9 (SEQ ID NO: 10), forming all isomeric nitrotryptophans in about 60% HPLC yield (Table 1, entries 1 and 2). Enzyme Pf2A6, on the other hand, showed almost quantitative conversion of 7-nitroindole to the corresponding nitroTrp, but had lower activity with 5- and 6-nitroindole (Table 1, entry 3). Because catalysts were identified that exhibited moderate activity with these substrates, experiments were further performed to determining if a subset of the mutations from Pf2A6 would further activate them for 5- and 6-nitroindole.

TABLE B

| Nitro substitution positions: |
| --- |
| 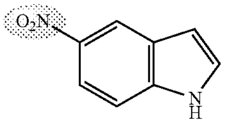<br>5-nitroindole |

TABLE B-continued

| Nitro substitution positions: |
| --- |
| 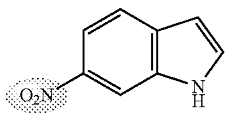<br>6-nitroindole |
| 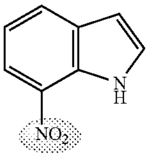<br>7-nitroindole |

TABLE 1

Catalyst activity to other nitroindole isomers:

| | | HPLC yield of nitroTrp (%)[a] | | | |
| --- | --- | --- | --- | --- | --- |
| Entry | Catalyst | 4-nitro | 5-nitro | 6-nitro | 7-nitro |
| 1 | Pf2B9 | 18 | 7.5 | 17 | 33 |
| 2 | Pf5G8 | 60 | 69 | 66 | 60 |
| 3 | Pf2A6 | 91 | 3.5 | 22 | >99 |
| 4 | Tm2F3[b] | | 76 | | |
| 5 | Tm2F3 I184F | | 86 | | |
| 6 | Pf2B9 I165F Y301H | | | 66 | |
| 7 | Pf0A9[c] | | | 86 | |
| 8 | Pf0A9 E104G | | | 91 | |

[a]Reactions used equimolar amounts of nitroindole and Ser. [b]TmTrpB plus mutations P19G, I68V, K96L, P140L, N167D, L213P, T292S. [c]Pf2B9 plus mutations M139L, I165F, N166D, and Y301H.

Engineered variants of TmTrpB had higher activity with 5-substituted indoles than their PfTrpB homologs. In addition, when certain beneficial mutations in PfTrpB variants were transferred to the corresponding positions in TmTrpB, then the activating effects were also transferred. Thus, a library in which the mutations of Pf2A6 were randomly recombined at the corresponding positions in TmTrpB were made (see, alignment in FIG. 2). When this library was tested for activity with 5-nitroindole, two variants were identified that outperformed all previous catalysts in the production of 5-nitrotryptophan. The first variant, Tm2F3, contained five mutations that were originally found in Pf2B9 plus all three mutations from Pf5G8; this variant formed 5-nitrotryptophan in 76% HPLC yield (Table 1, entry 4). The second variant was identical, but also contained one of the mutations found in Pf2A6 (I184F, according to numbering in *T. maritima*). This variant gave a further boost in yield to 86% (Table 1, entry 5).

Figure 10:
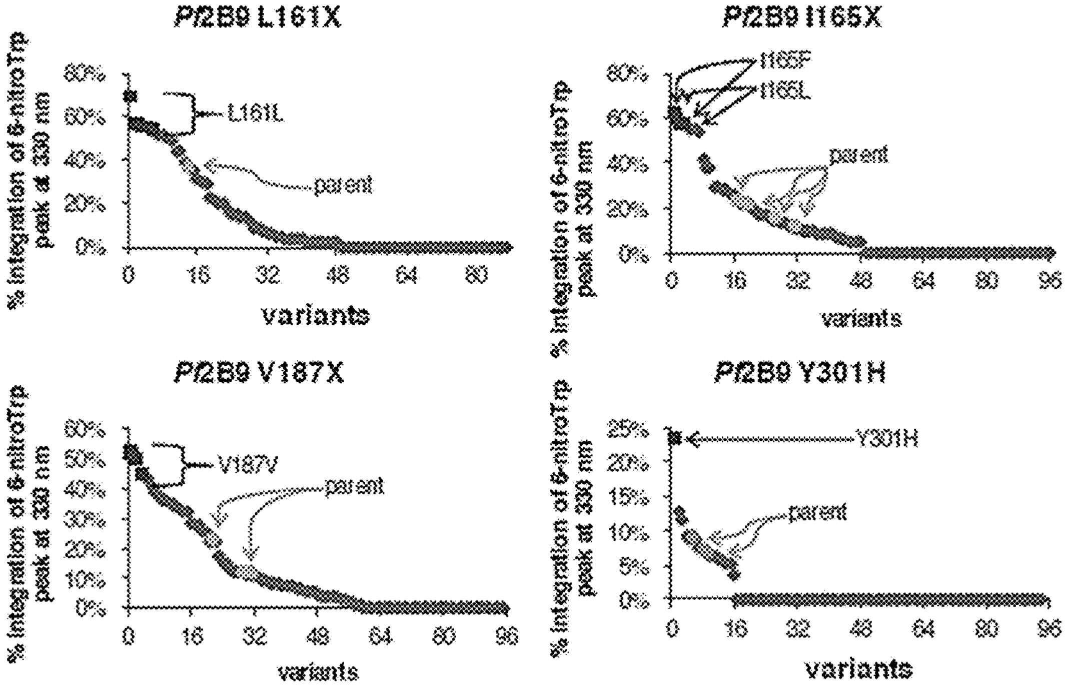
FIG. 10 shows site-saturation of Pf2B9 at L161, I165, V187, and Y301 for production of 6-nitrotryptophan. Product formation was measured by HPLC.

To improve activity with 6-nitroindole, mutation I165F and Y301H in SEQ ID NO: 10 were both beneficial (FIG. 10). Ultimately, the best variant contained both of these mutations and formed 6-nitroTrp in 66% HPLC yield (Table 1, entry 6). Thus, the disclosure also provides a mutant TrpB comprising SEQ ID NO: 10 with muations at I165 and Y301 that (or sequences that are 85%, 90%, 95%, 98%, 99% identical to SEQ ID NO: 10 and having mutations at I165 and Y301 wherein the polypeptide produces 6-nitroTrp from serine and 6-nitroindole).

A further random recombination library of the mutations from Pf2A6, from which a new variant, Pf0A9, was identified bearing mutations M139L and N166D, which increased the yield to 86% (Table 1, entry 7). Surprisingly, the mutation E104G also enhanced activity, albeit modestly, to 91% yield (Table 1, entry 8).

When the catalysts (mTrpBs of the disclosure) were applied to various indole analog substrates, the catalysts accepted essentially every indole analog tested, often forming the corresponding tryptophan product in excellent yield. For preparative reactions, however, halogenated and electron-deficient indoles were used, since historically these have been the most challenging.

With 4-nitroindole, Pf2A6 can achieve ~5000 turnovers, but the reaction seems to slow. As a result, a higher catalyst loading is used to achieve the high conversion observed in the catalyst evolution (Table 2, entry 1). Fortunately, the catalysts are expressed at high levels (>200 mg/L of *E. coli* culture) and can be used as heat-treated lysate, without additional protein purification. As a result, over a gram of 4-nitrotryptophan was obtained using the protein from a 1-L bacterial culture (Scheme 2). 4-fluorotryptophan was also obtained in excellent yield (Table 2, entry 2), as well as 4-bromo- and 4-cyanotryptophan (Table 2, entries 2 and 3, respectively).

Scheme 2

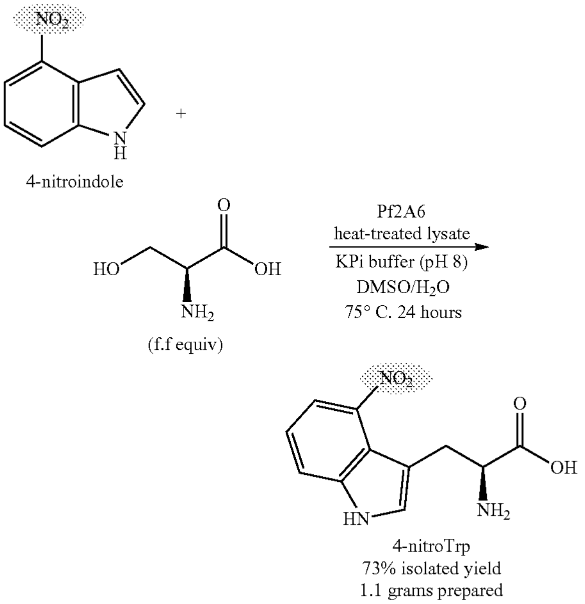

KPi = potassium phosphate

As with 4-nitroindole, the reaction with 5-nitroindole slowed toward the end. Nonetheless, 5-nitrotryptophan could be obtained in 88% yield with a higher catalyst loading (Table 2, entry 5). Good results were also obtained with other electron-withdrawing substituents, such as nitrile, carboxamide, and boronate (Table 2, entries 6-8). Notably, promising activity with 5-iodo- and 5-trifluoromethylindole (Table 2, entries 9 and 10) was observed.

The 6-substituted indoles proved to be the best behaved and most predictable series of substrates. At this position, high yields were obtained with the nitro substituent (Table 2, entry 11), as well as halo substituents (Table 2, entries 12 and 13) and other electron-withdrawing substituents like nitrile (Table 2, entry 14) and boronate (Table 2, entry 15).

Activity was also observed with 7-substituted indoles. While 7-nitroindole and 7-cyanoindole favored Pf2A6 (Table 2, entries 16 and 17), Pf0A9 gave optimal activity for 7-chloro- and 7-iodoindole (Table 2, entries 18 and 19). 7-bromotryptophan could be formed in modest yield with catalyst Pf5G8 (Table 2, entry 20).

The production of tryptophan analogs with multiple substituents was also examined (Table C). This capability is important both because poly-substituted Trp derivatives are precursors to many natural products and because polyhalogenated arenes are prevalent in bioactive compounds in general. The mTrpB's of the disclosure were capable of producing 5,6-disubstituted Trp 2 and 5,7-disubstituted Trp 3 in good yields using Pf5G8 and Tm2F3 I184F, respectively. The bulkier 5,7-disubstituted product 4 was also accessible.

TABLE C

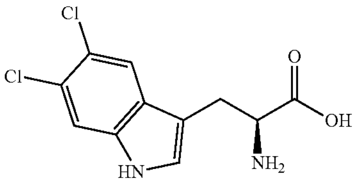

2
Pf5G8: 87% yield
4350 turnovers

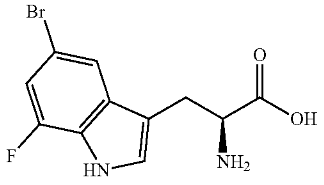

3
Tm2F3I184F: 56% yield
2800 turnovers

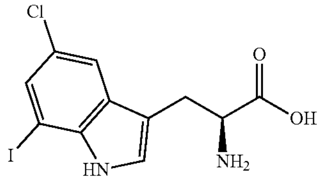

4
Tm2F3: 10% yield
500 turnovers

While the poor solubility of 4-nitroindole affected the ability to measure Michaelis-Menten kinetics, the initial rate of 4-nitroTrp production was estimated under the reaction conditions by measuring conversion at short reaction times (Table 3). In addition, the rate of Ser deamination was measured by incubating the enzymes with Ser, in the absence of a nucleophilic substrate, and measuring the production of pyruvate. Compared to the initial variant, Pf2B9 (SEQ ID NO: 10), variant Pf5G8 exhibits an increase in the rate of 4-nitroTrp production, but a six-fold decrease in the rate of Ser deamination (Table 3, entries 1 and 2). The mutation E104G improves both kinetic parameters in approximately equal measure (Table 3, entry 3). The addition of I183F and V186A actually increases the rate of Ser deamination, but increases the rate of the desired reaction even more (Table 3, entry 4).

TABLE 3

| Kinetics | | | |
|---|---|---|---|
| | | Initial turnover frequency ($min^{-1}$) | |
| Entry | Catalyst | to 4-nitroTrp | to pyruvate |
| 1 | Pf2B9 | 1.25 | 12 |
| 2 | Pf5G8 | 1.87 | 2.0 |
| 3 | Pf5G8 E104G | 3.33 | 0.87 |
| 4 | Pf2A6 | 6.82 | 1.4 |

Figure 11A:
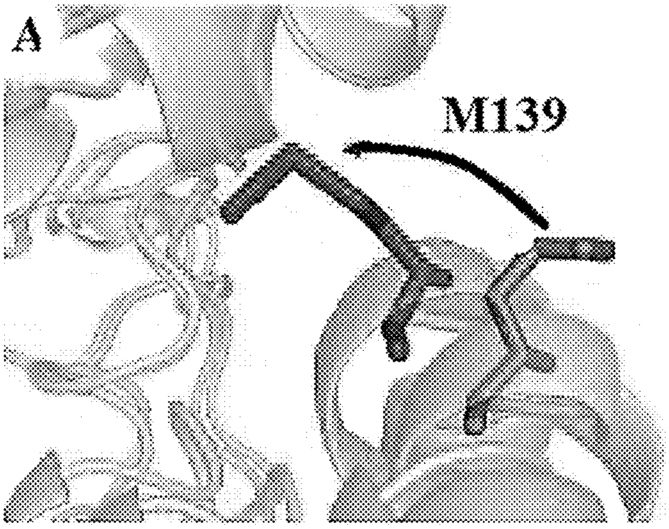
FIG. 11A-B shows overlaid crystal structures of PfTrpB (PDB ID: 5DVZ) in the open state and Pf2B9 (PDB ID: 5VM5) in the closed state showing the side-chain motion of (A) M139, (B) N166, and H275.
Figure 11B:
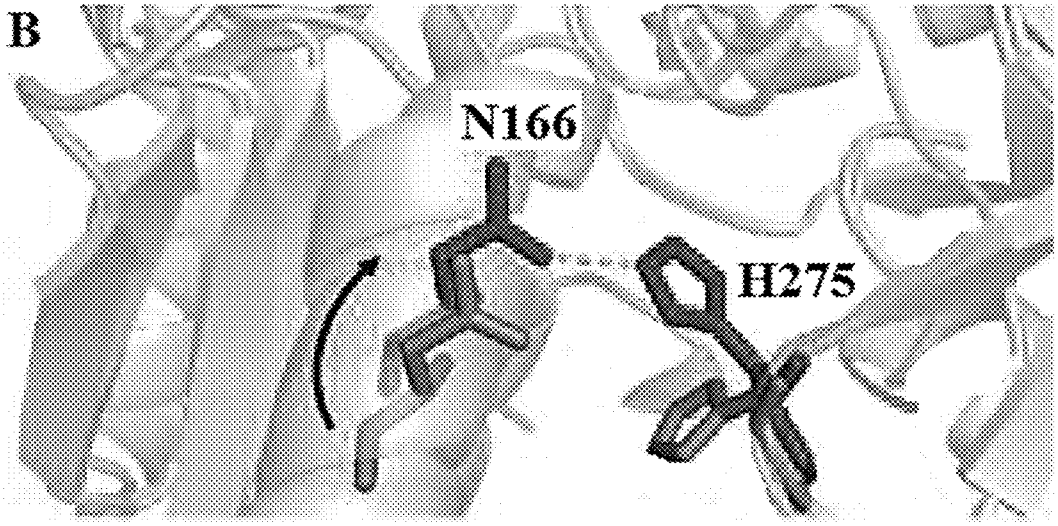

A comparison of the structures of wild-type PfTrpB in the open state, as well as Pf2B9 in the closed state revealed that the side-chain of M139, which is mutated to leucine in Pf5G8, undergoes a substantial movement when the protein transitions from open to closed (FIG. 11A). Thus, it is unsurprising that mutation at this position would influence the transition from open to closed. Residue N166, which is mutated to aspartate in Pf5G8, exhibits only a minor conformational change between open and closed, but its side-chain forms a hydrogen bond in the closed state with the side-chain of H275, which undergoes a rotameric switch that closes the active site (FIG. 11B). It is therefore plausible that strengthening of this interaction with the more basic aspartate would stabilize the closed state of the enzyme.

The mutations E104G, I183F, and V186A occur at positions in the enzyme active site. In the case of I183 and V186, the side chains do not interact directly with the substrates, nor do they undergo significant movement during the transition from the open to closed state. The beneficial effects of the mutations are likely due to subtle reshaping of the active site to accommodate the added bulk of 4-nitroindole and bind the substrate in a more reactive conformation. This is consistent with the observation that addition of these two mutations greatly increases the rate of 4-nitroTrp production while exerting little effect on the rate of Ser deamination (Table 3, entries 2 and 3).

Various roles have been assigned to the side-chain of E104, including activation of the Ser β-hydroxyl group as a leaving group, as well as binding and activation of the indole nucleophile (see FIG. 4, intermediates II and III). Indeed, studies of TrpS from *S. typhimurium* (StTrpS) showed that mutation of the corresponding residue to alanine eliminated activity with indole and Ser. However, this activity was rescued by the introduction of certain monovalent cations, such as $Cs^{+}$, indicating that neither of the aforementioned roles of E104 are essential. It therefore seems that its most significant role is in modulating the transition of the enzyme to the closed state. This was supported by the observation that increasing concentrations of CsCl shifted the catalytic steady state of the variant away from the external aldimine (FIG. 4, intermediate II) toward the amino-acrylate as the major species, a trend that is a hallmark of closed-state stabilization. By contrast, the amino-acrylate predominates in the steady state of both Pf5G8 and the E104G variant. In fact, the E104G mutation appears to stabilize the closed state, as inferred from the twofold decrease in deamination rate (Table 3, entries 1 and 2). Thus, it may be that the other mutations in Pf5G8 have changed the function of E104.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel") (each of which is incorporated by reference). Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564 (each of which is incorporated by reference). Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein (incorporated by reference herein), in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The invention is illustrated in the following examples, which are provided by way of illustration and are not intended to be limiting.

EXAMPLES

Cloning, expression, and purification of TrpB variants. The genes encoding Pf2B9 and TmTrpB (UNIPROT ID P50909) were cloned into pET22(b)+ with a C-terminal His-tag. Protein expression of the variants was carried out in *Escherichia coli* BL21 E. cloni Express cells (Lucigen) by inoculating 5 mL of Lysogeny Broth containing 100 μg/mL ampicillin (LBamp) with a single colony and incubating this pre-culture overnight at 37° C. and 230 rpm. The overnight cultures were used to inoculate 500 mL of Terrific Broth containing 100 μg/mL ampicillin (TBamp). The expression cultures were shaken at 37° C. and 230 rpm for ~3 h, at which point the OD600 was 0.6-0.8. The cultures were then chilled on ice for >30 min and then induced with by the addition of 1 M aq. isopropyl β-D-thiogalactopyranoside (IPTG, 500 μL, final concentration of 1 mM). Expression of the homologs took place at 230 rpm and 20° C. for another 20 h. The cultures were subjected to centrifugation at 5,000×g and 4° C. for 5 minutes. The cell pellets were decanted, then frozen and stored at −30° C. until further use.

For protein purification, cells were thawed, then resuspended in potassium phosphate buffer (25 mM, pH 8) that contained 20 mM imidazole, 100 mM NaCl, 200 μM PLP, 1 mg/ml of hen egg white lysozyme (HEWL, Sigma Aldrich), and 0.1 mg/ml of bovine pancreas DNase I. BugBuster (Novagen) was added, then the mixture was vortexed to suspend the pellet. The suspension was shaken at 37° C. and 230 rpm for 15 min, then subjected to centrifugation at 5000×g and 4° C. for 10 minutes. Without decanting, the cell lysate was immersed in a water bath at 75° C. After 30 minutes, the suspension was subjected to another centrifugation step (15,000×g and 4° C. for 15 minutes). The supernatant was purified using a 1-mL histrap HP column with an AKTA purifier FPLC system (GE Healthcare) and a linear gradient from buffer A (25 mM potassium phosphate, 20 mM imidazole, 100 mM NaCl, pH 8) to buffer B (25 mM potassium phosphate, 500 mM imidazole, 100 mM NaCl, pH 8) over 10 volumes. Proteins eluted at approximately 140 mM imidazole. Purified proteins were dialyzed into potassium phosphate buffer (50 mM, pH 8), then flash-frozen in liquid Ne and stored at −80° C. until further use. Protein concentrations were determined via the Bradford assay (Bio-Rad).

Construction of site-saturation mutagenesis libraries. PCR was conducted using Phusion polymerase (New England Biolabs) according to the standard protocol. For the given site of mutagenesis, three primers were designed containing codons NDT (encoding for Ile, Asn, Ser, Gly, Asp, Val, Arg, His, Leu, Phe, Tyr, and Cys), VHG (encoding for Met, Thr, Lys, Glu, Ala, Val, Gln, Pro, and Leu), and TGG (Trp), respectively, thereby including all 20 natural amino acids. These three primers were mixed in a ratio 12:9:1. Then, the plasmid was constructed by site-directed mutagenesis by overlap extension (SOE) PCR using a plasmid that contained the parent gene in the pET22 (b)+ vector as template. The linear plasmid was digested with DpnI, purified by preparative agarose gel, then cyclized via the Gibson method.

Construction of random recombination libraries. These libraries were constructed in an analogous manner to the site-saturation libraries, using primers that coded for both the native residue and the mutation. The mutant genes were first constructed as fragments, using flanking primers that corresponded to the NdeI and XhoI restriction sites on pET22(b)+. The fragments were purified by preparative agarose gel, then assembled into a contiguous gene using flanking primers that corresponded to the NdeI and XhoI sites of the pET22(b)+ vector. After a final purification by agarose gel, the assembled gene was cloned into an empty pET22(b)+ vector between restriction sites NdeI and XhoI using the Gibson method.

To improve production of 5-nitrotryptophan, recombination was performed in three stages. First, the mutations M18V, P19G, I69V, K96L, T292S, and H381A (relative to SEQ ID NO: 6) were randomly recombined in the parent TmTrpB M145T N167D (relative to SEQ ID NO: 6). The best variant from this library added the mutations P19G, I69V, K96L, and T292S (relative to SEQ ID NO: 6). This served as the parent polypeptide for the second round, in which the mutations P140L, M145T, N167D, and L213P (relative to SEQ ID NO: 6) were randomly recombined. The best variant from this library (Tm2F3; SEQ ID NO: 24) added the mutations P140L and L213P, retained the mutation N167D, and reverted the mutation M145T to the native residue (M). This served as the parent for the third round, in which the mutations E105G, I185F, and V187A were randomly recombined. The best variant from this library added the mutation I184F (see, e.g., SEQ ID NO: 26).

To improve production of 6-nitrotryptophan, recombination was performed in two stages. First, the mutations M139L, N166D, and L212P were randomly recombined in the parent Pf2B9 (SEQ ID NO: 10) further including I165F and Y301H. The best variant from this library (Pf0A9; SEQ ID NO: 20) added mutations M139L and N166D. This served as the parent polypeptide for the second round, in which the mutations E104G, I183F, and V186A were randomly recombined. The best variant from this library added the mutation E104G (SEQ ID NO:22).

Construction of random mutagenesis libraries. Random mutagenesis was achieved with error-prone PCR using Taq polymerase (New England Biolabs):

| Reagents mixed in a PCR tube | | Thermocycler program | | |
|---|---|---|---|---|
| Taq buffer (10×) | 10 μL | 95° C. | 40 s | |
| dNTP mix (200 μM) | 2 μL | 95° C. | 30 s | |
| forward primer[a] (100 μM) | 2 μL | 55° C. | 30 s | 30 cycles |
| reverse primer[b] (100 μM) | 2 μL | 68° C. | 80 s | |
| template DNA | 1 μL | 68° C. | 5 min | |
| $MnCl_2$ (1 mM) | 20/30/40 μL | 10° C. | ∞ | |
| Taq DNA Polymerase (added last) | 0.5 μL | | | |
| $H_2O$ | Add to 100 μL total volume | | | |

[a]Forward Primer corresponded to the NdeI restriction site for the pET22 (b) + vector.
[b]Reverse primer corresponded to the XhoI restriction site of the pET22 (b) + vector.

The PCR product was purified by preparative agarose gel, then cloned into an empty pET22 (b)+ vector between restriction sites of NdeI and XhoI using the Gibson method. 5 Libraries generated with 200, 300, and 400 μM MnCl2 were tested (one 96-well plate, each) to determine which library gave the optimal balance of high diversity and low rate of inactivation. The chosen library was then tested further.

Transformation of BL21 *E. coli* cells. In preparation, SOC medium, 50 L aliquots of electrocompetent BL21 *E. coli* cells, and electroporation cuvettes were chilled in ice. The plasmid (1 L) was added to the cells, which were then transferred to a sterile electroporation cuvette. An electric potential was applied with a Gene Pulser Xcell (2.5 kV, 25 μF, 200Ω). Then, SOC medium (750 μL) was immediately added and the cuvette was shaken at 37° C. and 230 rpm. After 45 min, aliquots of cell suspension were plated onto LBamp agar plates. The plates were incubated overnight at 37° C., then stored at 4° C. until further use.

Library expression and screening. BL21 E. cloni Express cells carrying parent and variant plasmids were grown in 96-well deep-well plates (300 μl/well TBamp) at 37° C. and 80% humidity. After shaking at 250 rpm overnight, 20 μL of the overnight cultures were transferred to new deep-well plates containing 630 μL/well TBamp, which were allowed to grow at 37° C. and 80% humidity. After shaking at 250 rpm for 3 h, the plates were chilled on ice for 30 min, then induced by the addition of IPTG in TBamp (1 mM final concentration). The cultures were shaken at 250 rpm and 20° C. After 20 hours, the cultures were subjected to centrifugation at 4,000×g for 10 min. The cell pellets were frozen at −30° C. for a minimum of 2 hours. For screening, cells were thawed at room temperature and then subjected to lysis by the addition of 400 μl/well of potassium phosphate buffer (50 mM, pH 8.0), with 1 mg/mL HEWL, 0.1 mg/mL DNase I, 40 μM PLP, and 2 mM $MgCl_2$. The plates were incubated for 1 h at 37° C., then transferred to a water bath equilibrated to 75° C. After 30 min, the plates were chilled in ice, then subjected to centrifugation at 5,000×g and 4° C. for 20 min.

The reactions were performed in 96-well deep-well plates. In general, each well was charged with the nitroindole substrate as a solution in DMSO (10 μL/well). Then, a solution of Ser in potassium phosphate buffer (200 mM, pH 8.0) was added. Finally, the enzymes were added as heat-treated lysate, such that the total volume in the wells was 200 μL. All libraries were screened with 2 μmol of nitroindole and 2 μmol of Ser, except for the first randommutagenesis library, which used 0.2 μmol 4-nitroindole and 2 μmol of Ser. The volume of heat-treated lysate was decreased in each successive round of evolution (80 μL to 20 μL), in order to apply greater selective pressure.

The plates were sealed with Teflon sealing mats, then immersed in a water bath equilibrated to 75° C. After ~12 hours, the plates were chilled in ice and subjected to brief centrifugation (5,000×g, 2 min) to settle the reaction contents to the bottom of the wells. Each well was charged with 700 μL of ethyl acetate and 500 μL of aq. 1 M HCl. The plates were again sealed with Teflon sealing mats, then shaken vigorously to dissolve all precipitates and partition the product and substrate between the aqueous and organic phases, respectively. The plates were again subjected to centrifugation (5,000×g, 2 min), then 200 μL of the aqueous phase were transferred to 96-well UV-vis assay plates. The activity of each well was determined by measuring the absorption at a given wavelength; the wavelength was determined by scanning one of the parent controls from 390 to 500 nm and choosing the wavelength at which the absorption was ~0.5.

For smaller libraries, such as for site-saturation mutagenesis, the reactions could also be analyzed by HPLC. In this case, the reactions were diluted with 300 μL of 83% cetonitrile/water (for 4-nitroindole reactions, 1 M aq. HCl was used in place of water). The plates were subjected to centrifugation at 5,000×g and 4° C. for 10 minutes, then the supernatants were transferred to a fresh assay plate. Each well was analyzed with a C-18 silica column (4.6×50 mm) using acetonitrile/water (0.1% acetic acid by volume): 5% to 95% acetonitrile over 2 minutes, 95% for 1 min; 1 mL/min. The yield was approximated by comparing the integrations of the nitrotryptophan signal to the nitroindole signal at 330 nm (no reference wavelength).

Small-scale reactions with heat-treated lysate. The enzyme was expressed as a 5-mL culture in TBamp according to the procedure in Section 5.1. The cell pellet was suspended in 400 μL potassium phosphate buffer (50 mM, pH 8) that contained 1 mg/mL HEWL, 0.1 mg/mL DNase I, and 200 μM PLP. BugBuster was added, then the suspension was shaken at 37° C. and 230 rpm. After 15 minutes, the suspension was chilled in ice, then subjected to centrifugation at 5,000×g and 4° C. (10 minutes). The supernatant was transferred to a 1.5-mL Eppendorf tube, then heated to 75° C. After 30 minutes, the suspensions were chilled in ice, then subjected to centrifugation at 20,000×g and 4° C. (10 minutes). The heat-treated lysate was used directly in the biocatalytic reactions.

A 2-mL HPLC vial was charged with nitroindole as a 200-mM solution in DMSO (10 μL, 2 μmol nitroindole). Next, Ser (2 μmol) was added as a solution in 180 μL of potassium phosphate buffer (200 mM, pH 8). Finally, 10 μL of heat-treated lysate was added, then the reaction was heated to 75° C. After 12 hours, the reaction was chilled in ice, then diluted with 800 μL of 1:1 $CH_3CN$/1 M aq. HCl. The reaction mixture was subjected to centrifugation at 20,000×g and 4° C. (10 minutes), then the supernatant was analyzed by HPLC with a C-18 silica column (1.8 μm, 2.1×50 mm) using acetonitrile/water (0.1% acetic acid by volume): 5% to 95% acetonitrile over 4 min; 1 mL/min. For 4-nitrotryptophan, the HPLC yield was determined using the method described in Section 5.9. For the other nitrotryptophans, the HPLC yield was estimated by comparing the integrations of the product and substrate peaks at 330 nm (no reference wavelength).

Small-scale reactions with purified protein. A 2-mL HPLC vial was charged with nitroindole as a 200-mM solution in DMSO (10 μL, 2 μmol nitroindole). Next, Ser (2 μmol) and PLP (5 equiv relative to enzyme) was added as a solution in 182 μL of potassium phosphate buffer (200 mM, pH 8). Finally, 8 μL of purified protein solution was added (concentration was adjusted depending on the desired catalyst loading).

Calibration for measuring HPLC yield of 4-nitrotryptophan. Using an authentic standard of 4-nitrotryptophan, mixtures were prepared that contained 4-nitroindole and 4-nitrotryptophan in different ratios (9:1, 3:1, 1:1, 1:3, and 1:9). Each mixture was prepared in duplicate, then all were analyzed by HPLC. The ratios of the product and substrate peaks at 254 nm (reference 360 nm, bandwidth 100 nm) and 330 nm (no reference wavelength) were correlated to the actual ratios by a linear relationship.

Turnover frequency of Ser deamination. The sample holder of a UV1800 spectrophotometer (Shimadzu) was heated to 75° C. For the reactions, enzyme and Ser in potassium phosphate buffer (200 mM, pH 8) were added to a quartz cuvette (1 cm path length), such that the total volume was 500 μL, and the final concentrations were 20 μM enzyme and 20 mM Ser. The potassium phosphate buffer was added first, then the cuvette was placed in the sample holder at 75° C. for at least 3 minutes, after which the baseline was measured (300 to 550 nm). Next, the enzyme was added, then the sample was again equilibrated to 75° C. for 3 minutes. After recording the UV-vis absorption spectrum (300 to 550 nm), Ser was added, then the absorption spectrum (300 to 550 nm) was measured every minute for 30 minutes. The change in absorption at 320 nm was correlated with the production of pyruvate using the extinction coefficient $\varepsilon=20\ M^{-1}cm^{-1}$. Three replicates of each measurement were performed.

| | Turnover frequency of Ser deamination ($min^{-1}$) | | | | |
|---|---|---|---|---|---|
| Enzyme | #1 | #2 | #3 | Average | Std. deviation |
| Pf2B9 | 11.8 | 11.9 | 13.0 | 12.2 | 0.5 |
| Pf5G8 | 2.2 | 1.7 | 2.2 | 2.0 | 0.2 |
| Pf5G8 E104G | 0.7 | 1.0 | 0.8 | 0.9 | 0.1 |
| Pf2A6 | 1.5 | 1.3 | 1.3 | 1.4 | 0.1 |

Turnover frequency of 4-nitrotryptophan production. Using the procedure described above reactions with 0.02 mol % of enzyme were run for 1 hour. The HPLC yield of 4-nitrotryptophan was then determined by HPLC using the calibration described above. Two replicates were performed of each experiment.

| | Turnover frequency of 4-nitroTrp ($min^{-1}$) | | | |
|---|---|---|---|---|
| Enzyme | #1 | #2 | Average | Std. deviation |
| Pf2B9 | 1.34 | 1.16 | 1.25 | 0.09 |
| Pf5G8 | 1.85 | 1.89 | 1.87 | 0.02 |
| Pf5G8 E104G | 3.25 | 3.41 | 3.33 | 0.08 |
| Pf2A6 | 6.79 | 6.86 | 6.82 | 0.03 |

Synthesis and characterization of tryptophan derivatives. Proton and carbon NMR spectra were recorded either on a Bruker 400 MHZ (100 MHz) spectrometer equipped with a cryogenic probe, or on a Varian 500 MHZ (125 MHZ) spectrometer. Fluorine NMR spectra were recorded on a Varian 500 MHZ (400 MHZ) spectrometer. Proton chemical shifts are reported in ppm (δ) relative to tetramethylsilane and calibrated using the residual solvent resonance (D20, δ 4.79 ppm, unless specified otherwise). Data are reported as follows: chemical shift (multiplicity [singlet (s), doublet (d), doublet of doublets (dd), doublet of doublets of doublets (ddd), triplet (t), triplet of doubles (td), multiplet (m)], coupling constants [Hz], integration). Carbon NMR spectra were recorded with complete proton decoupling. Carbon chemical shifts are reported in ppm relative to tetramethylsilane and calibrated using the residual solvent proton resonance as an absolute reference, unless specified otherwise. All NMR spectra were recorded at ambient temperature (about 25° C.) Preparative reversed-phase chromatography was performed on a Biotage Isolera One purification system, using C-18 silica as the stationary phase, with methanol as the strong solvent and water (0.1% HCl by weight) as the weak solvent. The gradient of the eluent (∇) is given as % strong solvent/column volume (CV). High-resolution mass spectrometry (HRMS) was conducted with an Agilent 6200 TOF, with samples ionized by electrospray ionization (ESI), or a JMS-600H (JEOL) instrument, with samples ionized by fast atom bombardment (FAB). All starting materials were purchased from commercial sources and used without further purification. Liquid chromatography/mass spectrometry (LCMS) was performed on an Agilent 1290 UPLC-LCMS equipped with a 2.1×50 mm C-18 silica column, using acetonitrile as the strong solvent and 0.1% (v/v) acetic acid/water as the weak solvent. The optical purity of the products was determined by derivatization with N-(5-fluoro-2,4-dinitrophenyl) alanamide (FDNPalanamide).

Screening catalyst panel against substrates. Reactions used the procedure described above. Product formation was approximated using HPLC by comparing the integration of product and substrate peaks at 277 nm. Catalyst loadings for each substrate are indicated in Table 2.

TABLE 2

Tryptophan analogs produced by catalyst panel.
Reactions used 0.02 mol % catalyst loading (maximum 5000 turnovers) and 1.1 equiv Ser relative to indole substrate. Catalyst loading was 0.1 mol % (maximum 1000 turnovers). Reaction gives alkylation at nitrogen.

| Entry | Substrate | R | Catalyst | Isolated Yield (%) |
|---|---|---|---|---|
| 1 | 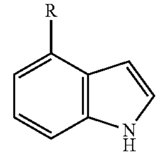 | $NO_2$ | Pf2A6 | 95[b] |
| 2 | | F | Tm2F3 | 97 |
| 3 | | Br | Tm2F3 | 72 |
| 4 | | CN | Tm2F3 I184F | 41 |
| 5 | 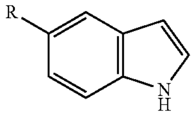 | $NO_2$ | Tm2F3 I184F | 88[b] |
| 6 | | CN | Tm2F3 | 79 |
| 7 | | $CONH_2$ | Tm2F3 | 77 |
| 8 | | $B(OH)_2$ | Pf0A9 | 37 |
| 9 | | I | Pf0A9 | 74[b] |
| 10 | | $CF_3$ | Pf2A6 | 19[b,c] |
| 11 | 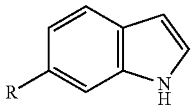 | $NO_2$ | Pf0A9 E104G | 91 |
| 12 | | Cl | Pf0A9 | 98 |
| 13 | | Br | Pf0A9 | 97 |
| 14 | | CN | Pf0A9 | 99 |
| 15 | | $B(OH)_2$ | Pf0A9 | 49 |
| 16 | 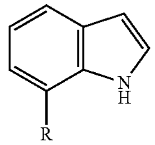 | $NO_2$ | Pf2A6 | 98 |
| 17 | | CN | Pf2A6 | 98 |
| 18 | | Cl | Pf0A9 | 99 |
| 19 | | I | Pf0A9 | 91 |
| 20 | | Br | Pf5G8 | 53 |

HPLC yields of tryptophan analogs with the catalyst panel.

| Substitution | Pf5G8 | Pf2A6 | Tm2F3 | Tm2F3 I184F | Pf0A9 | Pf0A9 E104G |
|---|---|---|---|---|---|---|
| 4-fluoro | 86% | 97% | 100% | 83% | 99% | 38% |
| 4-bromo | 57% | 29% | 69% | 40% | 30% | 0% |
| 4-cyano | 11% | 0% | 10% | 20% | 0% | 8% |
| 5-cyano | 30% | 3% | 81% | 69% | 8% | 3% |
| 5-aminocarbonyl | 55% | 0% | 79% | 79% | 64% | 0% |
| 5-borono | 31% | 0% | 41% | 31% | 44% | 0% |
| 5-iodo | 12% | 29% | 14% | 27% | 60% | 13% |
| 5-trifluoromethyl | 0% | 30% | 0% | 0% | 0% | 0% |
| 6-chloro | 100% | 53% | 100% | 100% | 100% | 47% |
| 6-bromo | 100% | 28% | 100% | 100% | 100% | 38% |
| 6-cyano | 21% | 14% | 6% | 5% | 100% | 73% |
| 6-borono | 3% | 0% | 0% | 2% | 63% | 0% |
| 7-cyano | 68% | 100% | 100% | 79% | 92% | 79% |
| 7-chloro | 56% | 100% | 83% | 80% | 100% | 80% |
| 7-bromo | 63% | 61% | 62% | 63% | 62% | 62% |
| 7-iodo | 87% | 91% | 90% | 63% | 100% | 58% |
| 5,6-dichloro | 100% | 11% | 73% | 55% | 83% | 48% |
| 5-bromo-7-fluoro | 70% | 9% | 89% | 91% | 81% | 83% |
| 5-chloro-7-iodo | 0% | 4% | 20% | 11% | 16% | 19% |

Preparative reactions for product characterization. General procedure: the indole analog (100 μmol) and Ser (110 μmol) were added to a 40-mL reaction vial, followed by DMSO (500 μL). PLP (5 equiv with respect to enzyme) was added as an aqueous solution (1.5 mM), then followed by enough potassium phosphate buffer (200 mM, pH 8) to make the final volume (with enzyme) 10 mL. The vial was sealed, then placed in a water bath that had been equilibrated to 75° C. After 1 min, the enzyme was added. The reaction was kept at 75° C. After 12 hours, the reaction mixture was frozen at −78° C., then the water was removed by lyophilization. The residual solid was washed twice as follows to remove the DMSO: toluene (6 mL) was added, then the suspension was heated to 75° C. After 2 minutes, the suspension was cooled in ice, then the toluene was removed.

The residual solid was suspended in 1:1 $CH_3CN$/1 M aq. HCl, then the volume was reduced in vacuo. This process was repeated once more. Once the organic solvent had been completely removed, the residual aqueous component was loaded onto a C-18 column (12 g) that had been equilibrated to 1% methanol/water (0.1% HCl by mass). The column was washed with 2 column volumes (CV) of this solvent mixture to remove salts and trace DMSO. Finally, the product was eluted with a gradient from 1% to 100% methanol over 10 CV. The fractions containing product were combined, then the organic solvent was removed in vacuo. The residual water was frozen and removed by lyophilization. The products were obtained as the hydrochloride salts.

Gram-scale preparation of 4-nitrotryptophan. The enzyme Pf2A6 was prepared in a 1-L TBamp expression culture according to the procedure described above. For lysis, the cell pellet (10.3 grams) was suspended in 41 mL of 50-mM potassium phosphate buffer (pH 8) that contained 2.18 mg PLP, 41.2 mg HEWL, and 4.12 mg DNase. BugBuster (4.12 mL, 10× concentration) was added, and then the suspension was shaken at 230 RPM and 37° C. After 15 minutes, the suspension was subjected to centrifugation at 4,500×g and 4° C. (5 minutes), and then immersed in a water bath at 75° C. After 30 minutes, the suspension was cooled in ice, then subjected to centrifugation at 15,000×g and 4° C. (15 minutes).

In a 500-mL Erlenmeyer flask, 4-nitroindole (973 mg, 6.00 mmol) and serine (694 mg, 6.60 mmol) were suspended in DMSO (6 mL) and 200-mM potassium phosphate buffer (84 mL, pH 8). Heat-treated lysate (30 mL) was added, then the reaction mixture was immersed in a water bath that was pre-heated to 75° C. After 24 hours, the reaction mixture was cooled in ice, whereupon most of the 4-nitrotryptophan precipitated. The precipitate was collected by filtration, then washed with water and ethyl acetate. To remove insoluble impurities, such as precipitated protein, the product was dissolved in 1:1 1 M aq. HCl/$CH_3CN$, then filtered again. The filtrate was concentrated in vacuo to afford 4-nitrotryptophan as the hydrochloride salt (yellow solid, 1.3 g, 73% yield).

Determination of optical purity. FDNP-alanamide was used as a solution in acetone (33 mM). In a 2-mL vial, the amino acid (0.50 μmol) was dissolved in 1 M aq. $NaHCO_3$ (100 μL). FDNP-alanamide (10 μL, 0.33 μmol) was added, then the vial was placed in an incubator at 37° C. and shaken at 230 RPM. After 2 h, the reaction mixture was allowed to cool to room temperature, then diluted with 1:1 CH CN/1 M aq. HCl (600 μL). The resulting solution was analyzed directly by LCMS (5% to 95% acetonitrile, monitored using the total ion count filtered for the expected mass). Each amino acid was derivatized with both racemic and enantiopure FDNP-alanamide for comparison. Absolute stereochemistry was inferred by analogy to L-tryptophan. All products were >99% ee, unless otherwise specified.

A number of embodiments of the invention have been described. Nevertheless, it will be understood that various modifications may be made without departing from the spirit and scope of the invention. Accordingly, other embodiments are within the scope of the following claims.

What is claimed is:

1. A recombinant tryptophan synthase β-subunit (TrpB) polypeptide comprising the sequence of any one of SEQ ID NOs: 14, 16, 18, 20, 22, 24, or 26.

2. The recombinant polypeptide of claim 1, comprising the sequence of SEQ ID NO: 14.

3. The recombinant polypeptide of claim 1, comprising the sequence of SEQ ID NO: 16.

4. The recombinant polypeptide of claim 1, comprising the sequence of SEQ ID NO: 18.

5. The recombinant polypeptide of claim 1, comprising the sequence of SEQ ID NO: 20.

6. The recombinant polypeptide of claim 1, comprising the sequence of SEQ ID NO: 22.

7. The recombinant polypeptide of claim 1, comprising the sequence of SEQ ID NO: 24.

8. The recombinant polypeptide of claim 1, comprising the sequence of SEQ ID NO: 26.

* * * * *